United States Patent
Campbell et al.

(10) Patent No.: US 7,625,337 B2
(45) Date of Patent: *Dec. 1, 2009

(54) CATHETER ASSEMBLY

(75) Inventors: Carey V. Campbell, Flagstaff, AZ (US); Edward H. Cully, Flagstaff, AZ (US); Sherif Eskaros, Elkton, MD (US); George N. Foutrakis, Oxford, PA (US); James William Mann, Elkton, MD (US); Peter J. Roeber, Wallingford, PA (US); Benjamin M. Trapp, Flagstaff, AZ (US); Michael J. Vonesh, Flagstaff, AZ (US)

(73) Assignee: Gore Enterprise Holdings, Inc., Newark, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/500,836

(22) Filed: Aug. 7, 2006

(65) Prior Publication Data

US 2007/0088323 A1    Apr. 19, 2007

Related U.S. Application Data

(63) Continuation-in-part of application No. 10/895,817, filed on Jul. 21, 2004, which is a continuation-in-part of application No. 10/402,083, filed on Mar. 28, 2003, which is a continuation-in-part of application No. 10/346,977, filed on Jan. 17, 2003, now abandoned.

(51) Int. Cl.
*A61B 1/12* (2006.01)
*A61M 29/00* (2006.01)

(52) U.S. Cl. .................... 600/156; 604/102.03

(58) Field of Classification Search ............... 604/524, 604/526, 527, 43, 510, 96.01, 97.01, 102.02, 604/102.03, 103.04, 103.09, 160, 164.03, 604/166.01, 264, 525, 921; 600/156, 104, 600/128, 124, 153, 116
See application file for complete search history.

(56) References Cited

U.S. PATENT DOCUMENTS

| 3,105,492 A | 10/1963 | Jeckel et al. |
| 3,953,566 A | 4/1976 | Gore .................. 264/288 |
| 4,187,390 A | 2/1980 | Gore .................. 174/102 R |
| 4,235,231 A * | 11/1980 | Schindler et al. ........ 604/6.09 |
| 4,552,554 A | 11/1985 | Gould et al. |

(Continued)

OTHER PUBLICATIONS

Compact English Oxford Dictionary: definition of "film" http://www.askoxford.com/concise_oed/film?view=uk.*

(Continued)

*Primary Examiner*—Kevin C Sirmons
*Assistant Examiner*—Catherine N Witczak
(74) *Attorney, Agent, or Firm*—Kevin J. Boland

(57) ABSTRACT

Novel catheter constructions comprising thin covering or wrapping materials such as polymer films. A catheter provided with a guidewire catheter lumen having a thin covering that is easily punctured by a guidewire at virtually any desired point along the catheter length. The thin covering may be integral with the catheter shaft, or may be a separate component that covers only the portion of the catheter shaft immediately adjacent the outer portion of the guidewire lumen, or may be a thin tubular construct that surrounds the entire catheter shaft. Moreover, polymer film can be used in combination with one or more elements to produce novel catheter constructions.

60 Claims, 34 Drawing Sheets

U.S. PATENT DOCUMENTS

| | | | |
|---|---|---|---|
| 4,601,713 A | 7/1986 | Fuqua | 604/280 |
| 4,762,129 A | 8/1988 | Bonzel | 128/334 |
| 4,877,661 A | 10/1989 | House et al. | 428/34.9 |
| 4,988,356 A | 1/1991 | Crittenden et al. | 606/192 |
| 5,024,234 A | 6/1991 | Leary et al. | |
| 5,030,210 A | 7/1991 | Alchas | 604/247 |
| 5,061,273 A | 10/1991 | Yock | 606/194 |
| 5,102,403 A | 4/1992 | Alt | 604/280 |
| 5,107,852 A | 4/1992 | Davidson et al. | 600/585 |
| 5,135,535 A | 8/1992 | Kramer | 606/194 |
| 5,171,222 A | 12/1992 | Euteneuer et al. | 604/102 |
| 5,195,978 A | 3/1993 | Schiffer | 604/161 |
| 5,205,822 A | 4/1993 | Johnson et al. | 604/96 |
| 5,273,042 A | 12/1993 | Lynch et al. | 600/434 |
| 5,324,269 A | 6/1994 | Miraki | 604/160 |
| 5,334,147 A | 8/1994 | Johnson | 604/96 |
| 5,334,153 A | 8/1994 | McIntyre et al. | 604/99.02 |
| 5,334,169 A * | 8/1994 | Brown et al. | 604/527 |
| 5,336,184 A | 8/1994 | Teirstein | 604/102 |
| 5,364,353 A | 11/1994 | Corfitsen et al. | 604/95.03 |
| 5,380,283 A | 1/1995 | Johnson | 604/96 |
| 5,380,290 A | 1/1995 | Makower et al. | |
| 5,389,087 A | 2/1995 | Miraki | 604/247 |
| 5,395,335 A | 3/1995 | Jang | 604/102 |
| 5,425,723 A | 6/1995 | Wang | 604/280 |
| 5,445,646 A | 8/1995 | Euteneuer et al. | 606/198 |
| 5,466,222 A | 11/1995 | Ressemann et al. | 604/103.09 |
| 5,472,423 A * | 12/1995 | Gronauer | 604/102.01 |
| 5,472,425 A | 12/1995 | Teirstein | 604/102 |
| 5,476,589 A | 12/1995 | Bacino | 210/500.36 |
| 5,489,271 A | 2/1996 | Andersen | 604/102 |
| 5,531,700 A | 7/1996 | Moore et al. | |
| 5,534,007 A | 7/1996 | St. Germain et al. | 606/108 |
| 5,573,520 A | 11/1996 | Schwartz et al. | |
| 5,591,194 A | 1/1997 | Berthiaume | 606/192 |
| 5,647,857 A | 7/1997 | Anderson et al. | 604/264 |
| 5,752,932 A | 5/1998 | Ellis et al. | 604/96 |
| 5,752,934 A | 5/1998 | Campbell et al. | 604/96.01 |
| 5,807,355 A | 9/1998 | Ramzipoor et al. | 604/282 |
| 5,846,259 A | 12/1998 | Berthiaume | 606/192 |
| 5,879,794 A | 3/1999 | Korleski | 428/317.1 |
| 5,919,164 A | 7/1999 | Andersen | 604/102 |
| 5,968,012 A | 10/1999 | Ren et al. | 604/96.01 |
| 5,972,441 A | 10/1999 | Campbell et al. | |
| 5,993,460 A | 11/1999 | Beitelia et al. | 606/108 |
| 6,016,848 A | 1/2000 | Egres, Jr. | 138/137 |
| 6,056,719 A | 5/2000 | Mickley | 604/96 |
| 6,059,813 A | 5/2000 | Vrba et al. | 606/198 |
| 6,095,990 A | 8/2000 | Parodi | 600/585 |
| 6,099,496 A | 8/2000 | Berthiaume et al. | 604/96 |
| 6,107,004 A | 8/2000 | Donadio, III | |
| 6,159,565 A | 12/2000 | Campbell et al. | 428/35.7 |
| 6,200,305 B1 | 3/2001 | Berthiaume et al. | 604/509 |
| 6,203,558 B1 | 3/2001 | Dusbabek et al. | 606/198 |
| 6,273,899 B1 | 8/2001 | Kramer | 606/194 |
| 6,299,595 B1 | 10/2001 | Dutta et al. | 604/96 |
| 6,398,799 B2 | 6/2002 | Kramer | 606/194 |
| 6,447,540 B1 | 9/2002 | Fontaine et al. | 623/1.12 |
| 6,783,522 B2 | 8/2004 | Fischell | 604/537 |
| 2002/0065550 A1 | 5/2002 | Smith | |
| 2002/0077654 A1 | 6/2002 | Javier et al. | |
| 2002/0082556 A1* | 6/2002 | Cioanta et al. | 604/113 |
| 2003/0050661 A1 | 3/2003 | Kramer | 606/194 |
| 2004/0122509 A1 | 6/2004 | Brodeur | |
| 2004/0193139 A1* | 9/2004 | Armstrong et al. | 604/523 |

OTHER PUBLICATIONS

MSN Encarta Definition of "catheter": http://encarta.msn.com/encnet/features/dictionary/DictionaryResults.aspx?refid=1861595493.

* cited by examiner

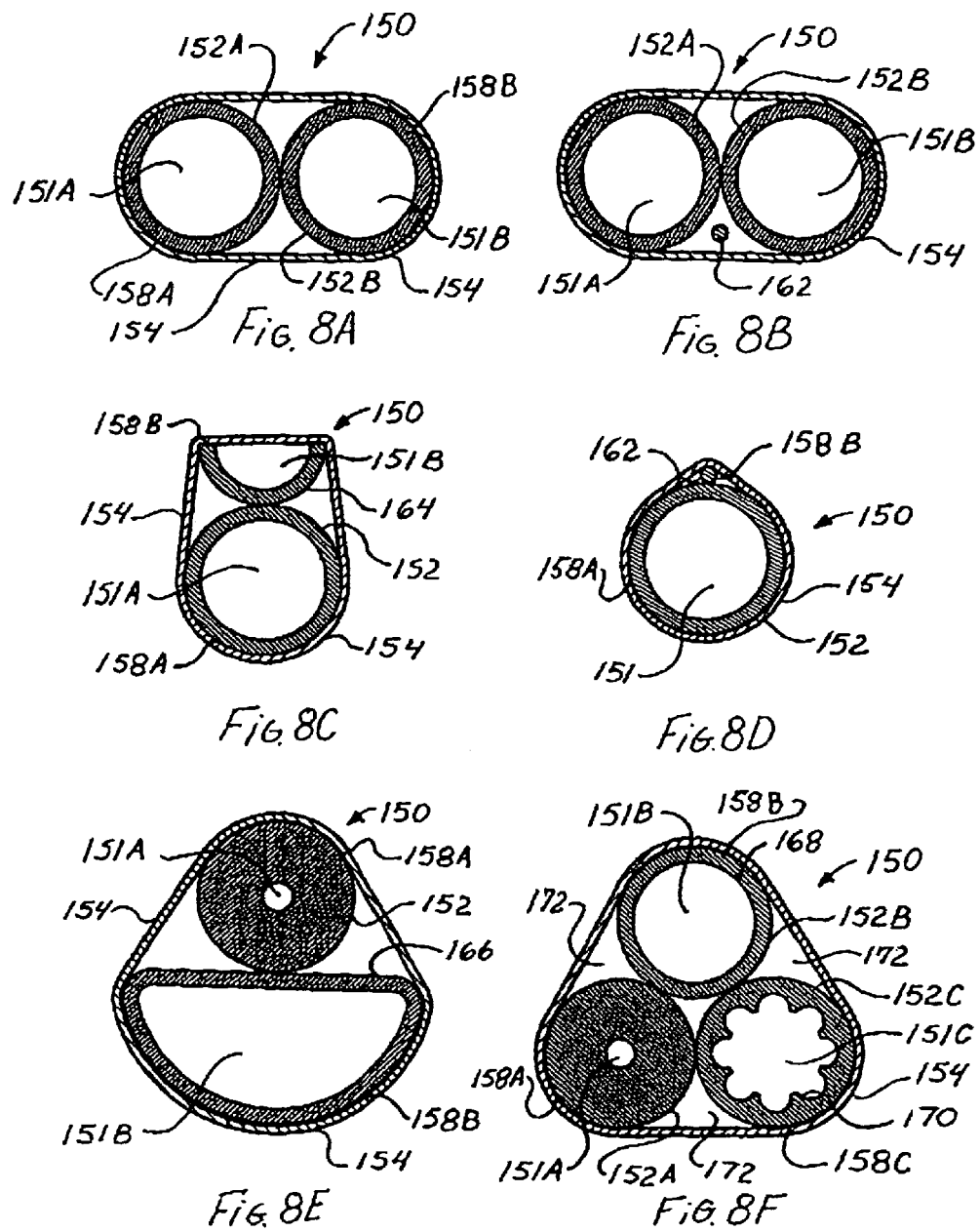

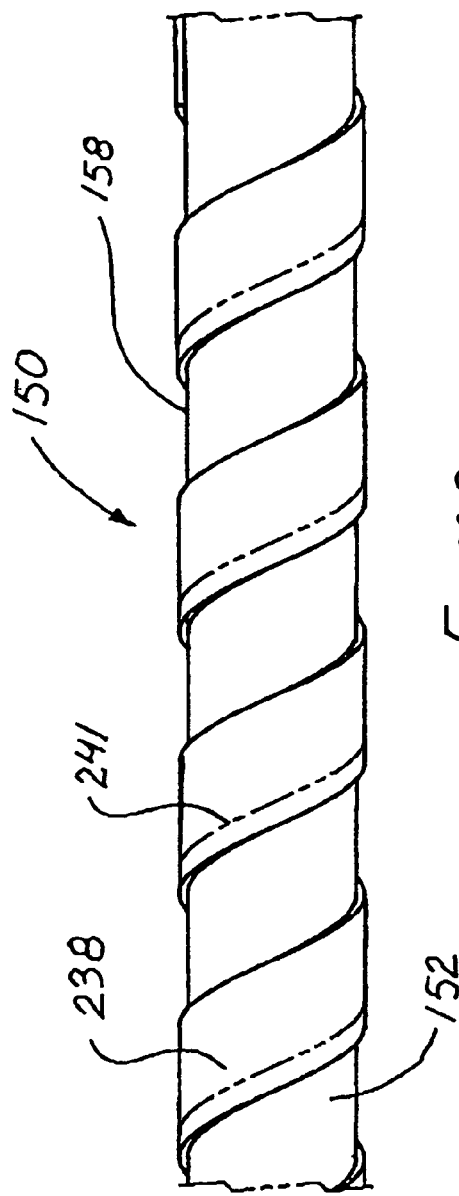
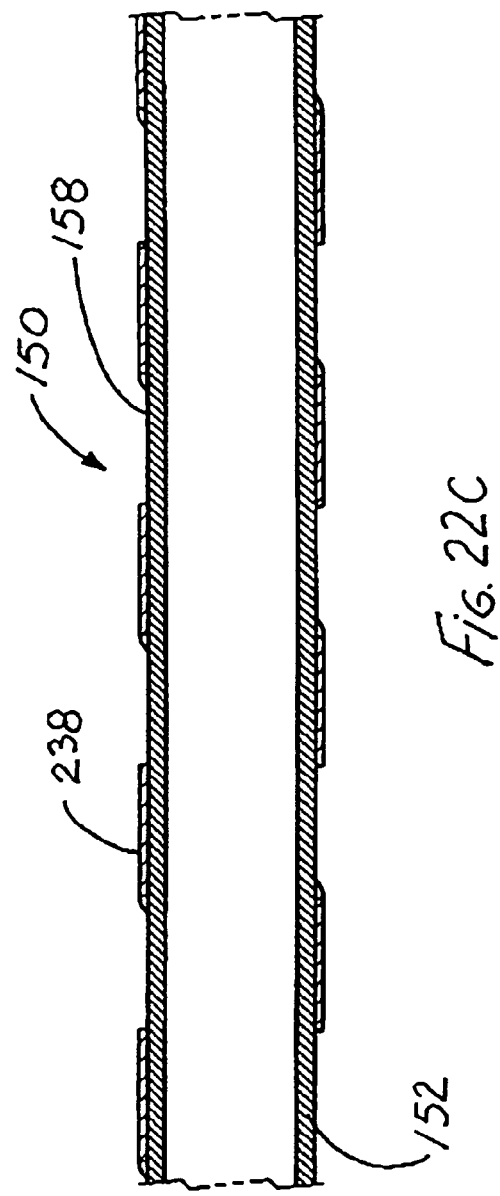

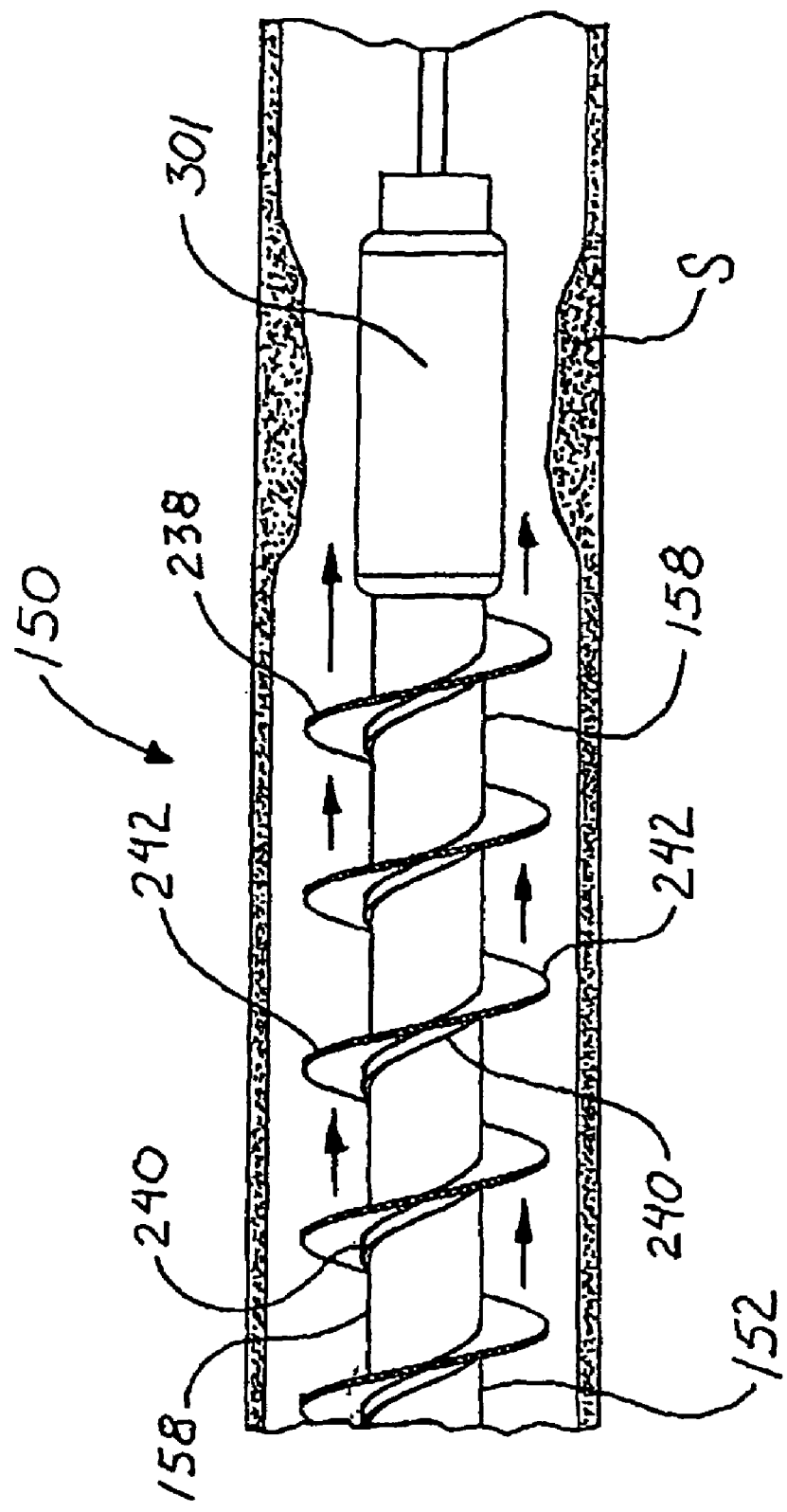

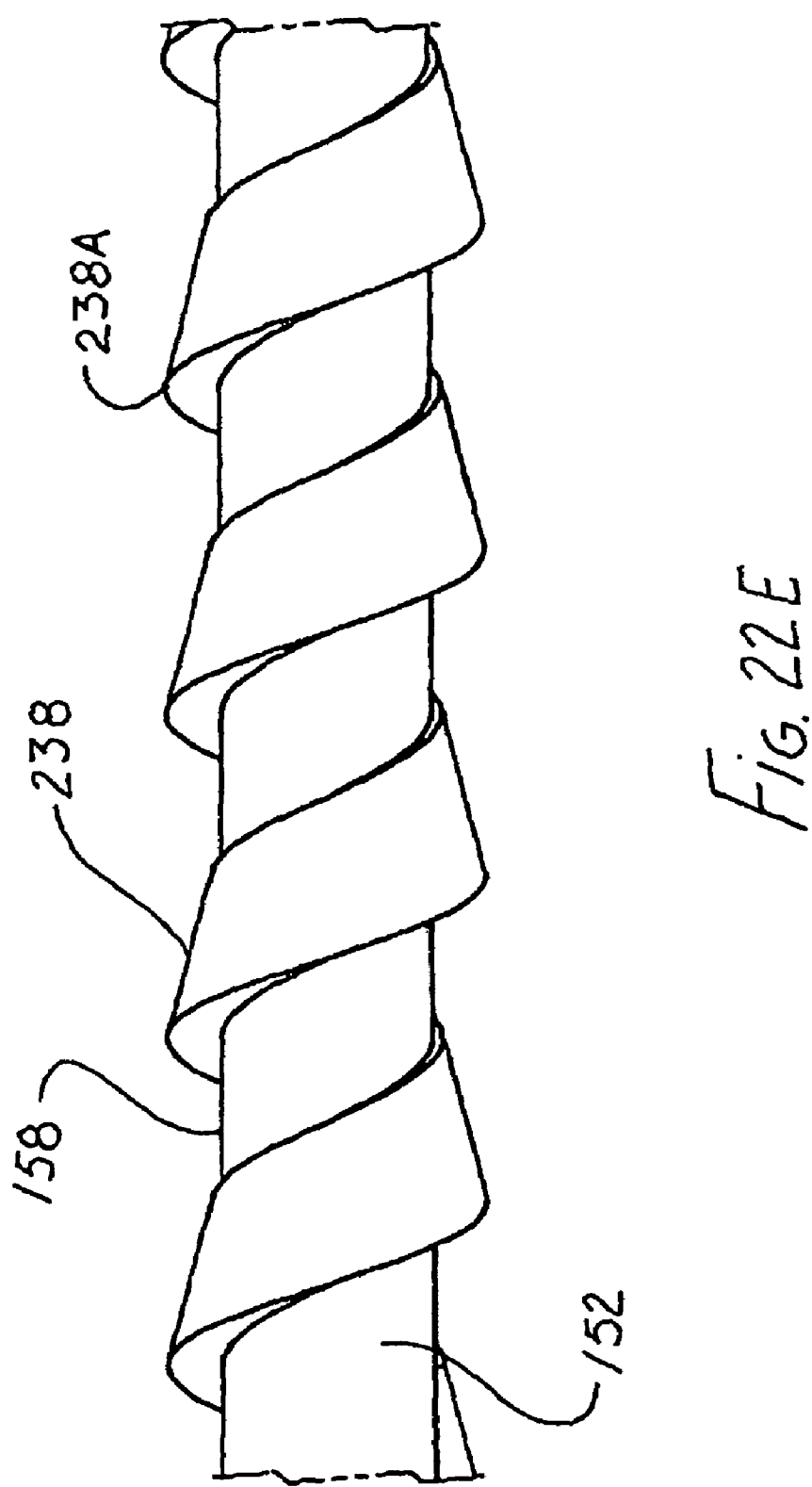

CATHETER ASSEMBLY

CROSS REFERENCE TO RELATED APPLICATIONS

This application is a continuation-in-part of U.S. patent application Ser. No. 10/895,817, filed Jul. 21, 2004, which is a continuation-in-part of U.S. patent application Ser. No. 10/402,083, filed Mar. 28, 2003, (entitled PUNCTURABLE CATHETER) which is a continuation-in-part of U.S. patent application Ser. No. 10/346,977 filed Jan. 17, 2003, now abandoned entitled ADJUSTABLE LENGTH CATHETER).

FIELD OF THE INVENTION

The present invention relates to the field of catheters. More particularly, the invention relates to catheters intended for the delivery to a patient of, for example, therapeutic agents or devices.

BACKGROUND OF THE INVENTION

A variety of different therapies can be delivered within the human body by catheter devices. Therapeutic devices such as dilation balloons, occlusion balloons, thrombectomy treatment devices, stents, and embolic filters, and therapeutic agents such as drugs and radiation sources, may be positioned at or near the distal end of the catheter for delivery to a desired site within the body. The proximal end of the catheter is considered to be the end that remains outside of the body, manipulated by the medical practitioner.

To aid in positioning of the distal end of the catheter within the body, typically the distal end of a guidewire is first navigated to the treatment area. After the guidewire has been positioned, the wire can then be used to guide the distal end of the catheter into place. Additionally, a guide catheter may be used to further facilitate the positioning of the guidewire and/or delivery catheter. The interaction between the guidewire and the catheter is critical, as the physician needs to easily track the distal end of the catheter along the path of the guidewire. A number of interaction issues can arise, including but not limited to, having to use more than one person, having to use a long wire, having the advancement of the catheter affect the position of the wire, having the catheter not able to track the wire through tortuous anatomy, having excessive friction between the catheter and the wire, and having a difference between the amount of axial motion applied to the proximal end of the catheter and the amount of axial movement at the distal end of the catheter.

In various attempts to address these issues, a number of catheter designs have been introduced that have defined the interaction between the guidewire and the catheter. Two of the primary applications of catheter systems are percutaneous transluminal coronary angioplasty (PTCA) and coronary stent delivery. Two main types of catheter designs, over-the-wire (OTW) and rapid-exchange (RX), dominate these applications. Each of these designs has its advantages and disadvantages. OTW catheters track over their entire length on a guidewire, which allows them to follow the wire easily and allows the direct transmission of longitudinal force over the guidewire. Additionally, these catheters allow for guidewires to be exchanged once the catheter has been advanced into position, which may be desirable when different guidewire attributes (e.g., tip curvature or radiopaque markers) are needed. However, these systems require the use of a long guidewire (e.g., 300 cm in length) and cannot be effectively operated by one person.

RX catheters typically use shorter guidewires (e.g., 180 cm in length) which allow the catheter to be operated by a single physician. The physician is able to hold the guide catheter and guidewire with one hand while using his other hand to advance or retract the catheter along the guidewire. However, because the entire length of the RX catheter does not slide over the guidewire, the direct transmission of longitudinal force along the path of the guidewire may be compromised, and wire exchange can not be performed once the proximal catheter guidewire port is advanced into the patient.

Furthermore, it is not uncommon for OTW and RX catheters (among others) to be constructed by a plastic (or polymer) extrusion process. Producing, for example, an OTW or RX catheter with a tight tolerance, with a dual lumen construction can be difficult and expensive via an extrusion process.

Among various further catheter designs intended for stent delivery is a system taught by U.S. Pat. No. 5,534,007 to St. Germain et al. This system includes a tubular exterior sleeve with an adjustable length section that, under axial compression, shortens via corrugations to cause another sleeve at the distal end of the catheter to be withdrawn in a proximal direction, releasing the stent. The overall length of the catheter remains the same during the axial compression of the exterior sleeve, and in particular, the length of the guidewire lumen is not adjustable.

U.S. Pat. Nos. 5,334,147 and 5,380,283 to Johnson teach the construction of a balloon catheter having a proximal portion that includes an aperture through the wall of the catheter into the guidewire lumen. The aperture is covered by a frangible wall (e.g., a thin-walled tube sealed to the catheter body in a position to cover the aperture portion). The frangible wall may be punctured by a guidewire, allowing the guidewire to exit the catheter guidewire lumen via the aperture.

U.S. Pat. No. 5,472,425 to Teirstein describes a catheter having a guidewire lumen covered by a rupturable membrane that extends along substantially the entire length of the catheter, whereby the membrane may be intentionally punctured at any desired location by the guidewire. The use and general construction of the catheter are related, although no materials or specific constructions for the rupturable membrane are taught.

U.S. Pat. No. 6,423,032 to Parodi describes methods and apparatus for removing emboli during an angioplasty, stenting, or surgical procedure comprising a catheter having an occlusion element, an aspiration lumen, and a blood outlet port in communication with the lumen, a guide wire having a balloon at its distal end, a venous return catheter with a blood inlet port, and tubing that couples the blood outlet port to the blood inlet port. Also described is apparatus for occluding the external carotid artery to prevent reversal of flow into the internal carotid artery. The pressure differential between the artery and the vein provides reverse flow through the artery, thereby flushing emboli.

U.S. Pat. No. 6,929,634 to Dorros et al. describes methods and apparatus for treatment of stroke. Specifically described is a catheter having a distal occlusive member capable of being disposed in the common carotid artery of the hemisphere of the cerebral occlusion. Retrograde flow may be provided through the catheter to effectively control cerebral flow characteristics. Under such controlled flow conditions, a thrombectomy device may be used to treat the occlusion, and any emboli generated are directed into the catheter.

SUMMARY OF THE INVENTION

The invention relates to novel catheter constructions comprising thin covering or wrapping materials such as polymer films. A first aspect relates to a catheter provided with a guidewire catheter lumen having a thin covering that is easily punctured by the back end (i.e., the proximal end) of a guidewire at virtually any desired point along the catheter length. The thin covering may be integral with the catheter shaft, or may be a separate component that covers only the portion of the catheter shaft immediately adjacent the outer portion of the guidewire lumen, or may be a thin tubular construct that surrounds the entire catheter shaft. The covering is preferably adequately translucent to allow for good visualization of the location of the back end of the guidewire in order to enable puncturing of the covering at the desired location along the length of the catheter shaft. The catheter shaft is preferably made of a material having a color that provides good visibility against an operating field, and more preferably is luminous or phosphorescent either entirely or in part. Materials suitable for the catheter shaft are polymeric materials well known in the art; the catheter shaft may optionally be provided with metallic stiffening components such as wires, wire braids or hypotubes along all or part of the catheter length.

In an aspect of the invention, the thin covering or wrapping material is made from a thin tape of porous expanded polytetrafluoroethylene (ePTFE) that can be helically wrapped about the exterior of a catheter shaft. Most preferably, the wrapping is accomplished in two opposing directions parallel to the length of the catheter shaft, resulting in a bias-ply construction. This thin covering offers good transparency and is easily punctured by the end of a guidewire, and yet is resistant to tearing at the puncture site.

Other materials may be used for the puncturable thin covering, including polyethylene terephthalate (PET). These materials may also offer good translucency, but may be less tear resistant than the helically wrapped ePTFE thin coverings.

The thin covering (either integral with the catheter shaft or a separate covering) may optionally be provided with a multiplicity of small, pre-formed openings through the thickness of the covering to allow for passage of the back end of a guidewire through any of these openings. The openings would preferably be arranged in a single line extending directly above the guidewire lumen.

The thin covering may optionally be in the form of a braid or helically-wound filaments that allow the guidewire to be passed through any of the multiplicity of openings or interstices that exist between adjacent filaments of the braid or winding. The braid or winding may be of either various polymeric or metallic materials. The braid or winding may be exposed around the entire exterior of the catheter shaft or alternatively may be exposed over only the side of the guidewire lumen closest to the exterior of the catheter shaft.

For many embodiments, the guidewire lumen is in the form of a slot made into the catheter shaft, with the slot provided with the thin covering. Preferably, the slot extends for most or even all of the length of the catheter shaft. It may optionally extend through a balloon or other device located at the distal end of the catheter. The slot is covered with a thin tubular covering that coaxially encloses the entire catheter shaft or alternatively a strip of thin tape-like covering material that covers the slot and is adhered to the surface of the catheter shaft immediately adjacent both sides of the slot. A multiplicity of pre-formed openings may be provided through the thin covering as noted above. Also as noted above, the slot covering material may take the form of a braid or winding of filaments. This braid or winding of filaments may optionally be covered with a thin polymeric tube except for the filaments immediately over the top of the slot which preferably remain exposed and allow for passage of the end of a guidewire through any interstice between adjacent filaments.

Other embodiments using the catheter shaft may be provided with a puncturable tubular form inserted into the slot. This tubular form may be made with filaments braided into the tubular form, or a tubular form made of helically wound filaments or from a thin polymeric material, with the tube having an inside diameter adequately large to accommodate a guidewire of the desired size. These tubes are fitted and secured into the slot formed into the catheter shaft, with the result that the outer surface of the braided or helically wound tube covers the exposed part of the slot and allows for the back end of a guidewire contained within the tube to be passed through any interstice between adjacent filaments of the braided or helically wound tube. When the tubular form is made from the thin polymeric material, the resulting tube inserted into the catheter shaft slot is puncturable at any desired location by the back end of a guidewire.

The ability of the catheter to be punctured by the back end of a guidewire at any desired location along the length of the puncturable section of the catheter allows the catheter assembly to be used effectively as desired in either OTW or RX mode.

In addition to being puncturable by the back end of the guidewire, the guidewire catheter lumen may optionally be made to be adjustable in length. The adjustable length catheter guidewire lumen is the conduit, or catheter, or tube, or space that contains the guidewire or provides a space for the passage of a guidewire therethrough. The space may be adjustable in length, as will be further described.

By adjustable length is meant that the length of the adjustable length guidewire catheter lumen may be changed by the application of easily applied manual axial force. In its axially extended or fully lengthened state, the adjustable length guidewire catheter lumen is at least 10% longer than when in the axially compressed, fully shortened state. More preferably, the adjustable length guidewire catheter lumen is adjustable by an amount of at least about 20%, or 30%, or 40%, or 50%, or 75%, or 100%, or 200%, or 400%, or 1000%, or 2000%.

The adjustable length guidewire catheter lumen is adjustable in length by virtue of being scrunchable. This means that this tubular component is easily shortened in length under axial force, without telescoping as by the successive sliding of overlapped concentric tubular sections. Various means of providing a scrunchable tube for use as the adjustable length guidewire catheter lumen include the provision of corrugations (i.e., wrinkles, or accordion pleats or folds), or by the use of a porous tube that compresses axially by reduction in total void space. These are further described below.

In a further aspect of the invention, polymer film is used in combination with one or more elements to produce novel catheter constructions. For example, polymer film can be wrapped about one or more catheter elements to produce useful catheters. Moreover, catheters can be formed by wrapping a suitable polymer film about a mandrel and removing the mandrel to obtain a catheter having at least one lumen therein. Moreover, polymer film can be provided in tubular form, which may be a heat shrinkable material such as a tube comprising polyethylene terephthalate (PET).

Suitable materials for the adjustable length lumen and the polymer film include ePTFE, polyethylene terephthalate (PET), polyamide, or other thermoplastic or thermoset polymers, or other such relatively inelastic materials. Alternatively, an elastomeric material may be used, which materials elongate by the application of an extending axial force. The term "elastomeric" is intended to describe a condition whereby a polymer displays stretch and recovery properties similar to an elastomer, although not necessarily to the same degree of stretch and/or recovery.

In a further aspect of the invention wire-based guidewires and catheter or micro-catheter systems are provided. Such systems comprise at least one longitudinally extending wire having a length and at least an outer surface with at least one cut therein, a proximal end, and a distal end. The wire-based device further comprises polymer film covering at least a portion of the outer surface of the at least one wire. The wire-based device further includes at least one therapeutic device and/or a diagnostic device, located at the distal end thereof. Such systems may comprise one or more balloon on wire devices as described further herein in more detail.

BRIEF DESCRIPTION OF THE DRAWINGS

FIG. 8A is a cross-section of a catheter construction according to the present invention.

FIG. 8B is a cross-section of a catheter construction according to the present invention.

FIG. 8C is a cross-section of a catheter construction according to the present invention.

FIG. 8D is a cross-section of a catheter construction according to the present invention.

FIG. 8E is a cross-section of a catheter construction according to the present invention.

FIG. 8F is a cross-section of a catheter construction according to the present invention.

FIG. 22B is a perspective view of a catheter according to the present invention.

FIG. 22C is a cross-section of a catheter according to the present invention.

FIG. 22D is a perspective view of a catheter according to the present invention being advanced into a vessel or artery.

FIG. 22E is a perspective view of a catheter according to the present invention.

DETAILED DESCRIPTION OF THE INVENTION

Figure 1A:
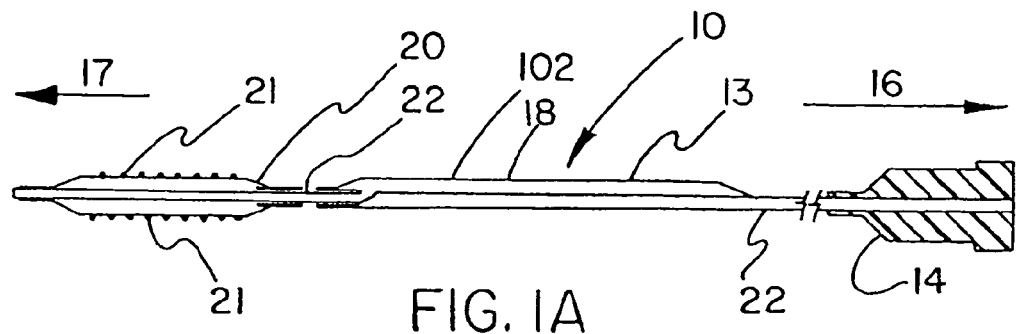
FIG. 1A shows a longitudinal cross section of a catheter having a puncturable guidewire lumen covering.

FIGS. 1A-1H describe a catheter 10 of the present invention provided with a thin, puncturable cover 102 over the guidewire lumen 18. Typically, catheter 10 may include devices such as a catheter balloon 20 and/or stent 21 at its distal end 17 and a hub 14 at the proximal end 16. As shown by FIGS. 1A-1H, the thin, puncturable cover 102, in this instance a thin-walled tubular sheath 13 (forming guidewire lumen 18) designed to be punctured by the back end of a guidewire 19 (or other suitable means), may be placed coaxially about the inflation lumen 22. The length of the thin tubular sheath 13 may extend over all or part of the length of catheter shaft.

After feeding guidewire 19 through the distal section of the guidewire lumen 18 and into the thin-walled tubular sheath 13, the physician may choose any desired location along the length of thin-walled tubular sheath 13 at which to puncture the thin, puncturable cover 102 with the guidewire 19. In this fashion the physician may select his preferred length of the guidewire lumen 18.

Figure 1B:
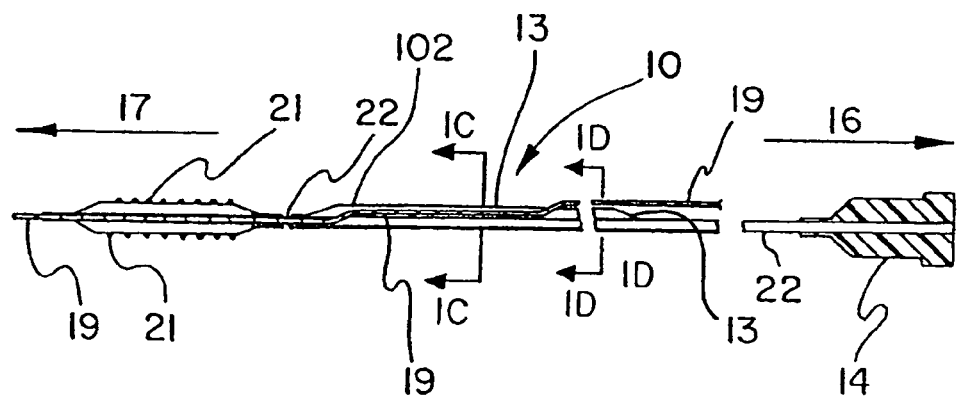
FIG. 1B shows a longitudinal cross section of the catheter of FIG. 1A in use with the catheter, the guidewire having punctured the puncturable guidewire lumen covering.
Figure 1C:
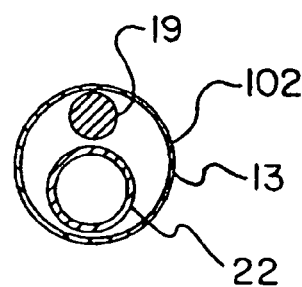
FIGS. 1C and 1D show transverse cross sections of the catheter of FIG. 1B with the guidewire within and without the puncturable section.
Figure 1D:
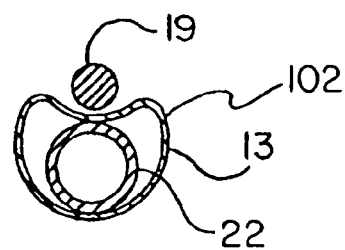

FIG. 1A shows a longitudinal cross section of a catheter 10 having a puncturable guidewire lumen covering 102, while FIG. 1B shows a longitudinal cross section of the catheter of FIG. 1A in use with the guidewire 19, the guidewire having punctured the puncturable covering 102. FIGS. 1C and 1D show, respectively, transverse cross sections of the catheter of FIG. 1B with the guidewire 19 within and outside of the puncturable section 102.

Figure 1E:
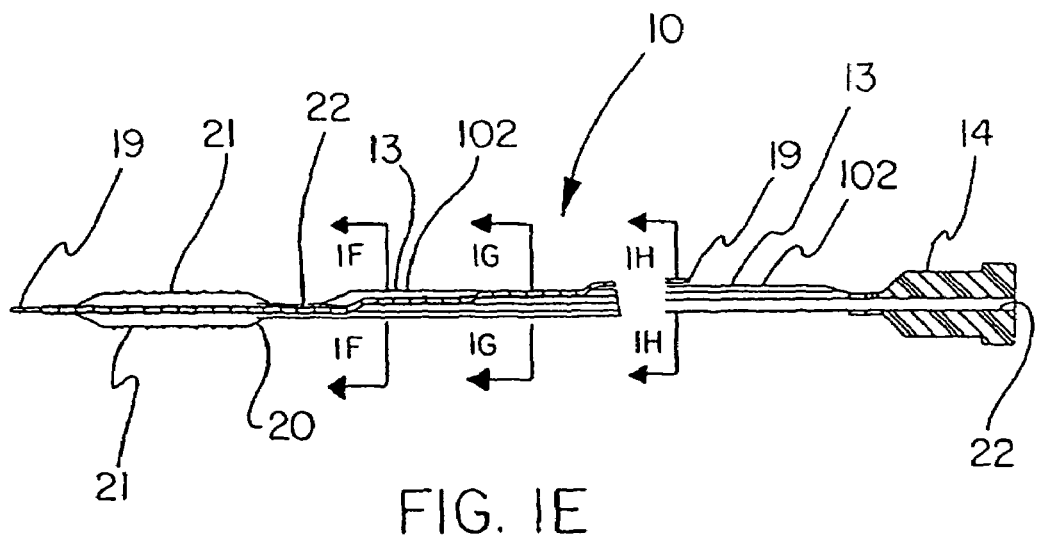
FIG. 1E shows a longitudinal cross section of a catheter that is a variation of the design shown in FIGS. 1A and 1B wherein the guidewire operates in a slot provided in the exterior wall of a lumen of the catheter.
Figures 1F, 1G:
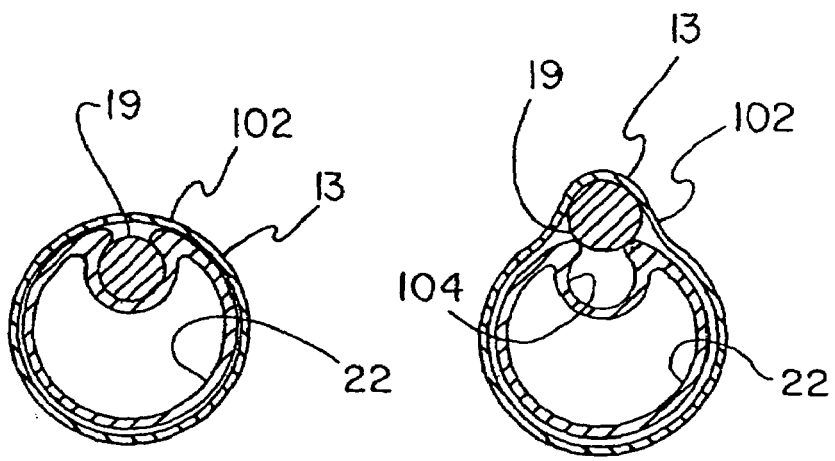
FIGS. 1F, 1G and 1H show transverse cross sections taken at three different locations along the length of the catheter shown in FIG. 1E.
Figure 1H:
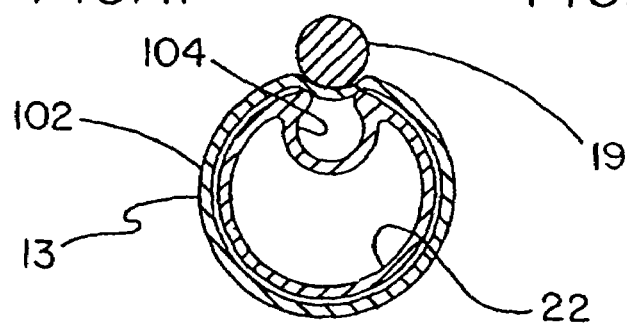

FIG. 1E shows a longitudinal cross section of a catheter that is a variation of the design shown in FIGS. 1A and 1B wherein the guidewire operates in a slot 104 provided in the exterior wall of a lumen of the catheter. It is apparent that the thin, puncturable cover 102 may be provided only over this slot portion and is not required to enclose the entire circumference of the inner catheter. FIGS. 1F, 1G and 1H show transverse cross sections taken at three different locations along the length of the catheter shown in FIG. 1E.

The puncturable guidewire lumen may be made in a variety of ways.

Figure 2A:
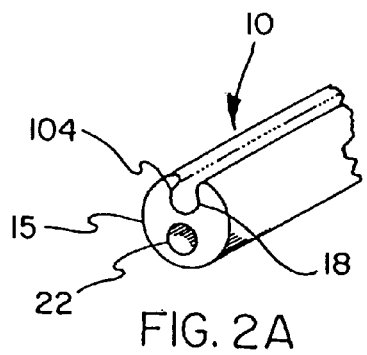
FIG. 2A shows a perspective view of a preferred slotted catheter shaft.

In a preferred embodiment, catheter 10 including inflation lumen 22 and guidewire lumen 18 is made using a catheter shaft 15 as shown in the perspective view of FIG. 2A wherein guidewire lumen 18 is in the form of a slot 104. The catheter shaft 15 may be made in this form by extrusion (using any known polymeric material suitable for the application), or may alternatively be extruded with fully enclosed lumens and then have the extruded material covering the guidewire lumen skived away. Preferred materials will be of a color offering good contrast with the operational field, and most preferably are fluorescent or phosphorescent.

Optionally, such a catheter shaft may be stiffened along all or part of its length as necessary by the inclusion of stiffening wires running parallel to the longitudinal axis of the catheter, or by adding a tubular metal reinforcing braid to the catheter shaft, or by inserting a length of metal hypotube, tubular braid or helically wound wire into the inflation lumen 22. These stiffening methods may be used in combination if desired. For simplicity, these well-known stiffening methods are not shown in the figures.

If it is desired to use a hypotube to stiffen only a portion of the length of the catheter shaft, it may be desirable to cut a helically-oriented slot through the wall of the end of the hypo tube that will be located within the length of the catheter shaft to reduce the abrupt stiffness transition of the stiffened section to the unstiffened section.

Figure 2B:
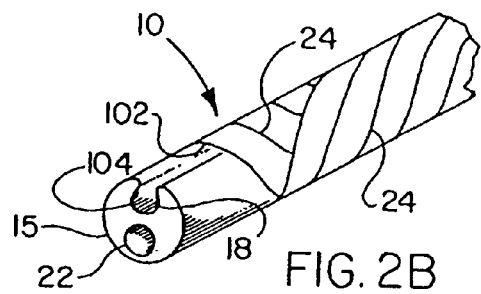
FIG. 2B is a perspective view of the preferred slotted catheter shaft of FIG. 2A provided with a helical wrap of a polymeric tape that forms a puncturable thin cover over the slot.

As shown by the perspective view of FIG. 2B, the slotted catheter shaft 15 is provided with a helically-wrapped covering of tape 24. Preferably, the wrapping is applied in two layers wherein adjacent wrappings have overlapping edges and the second layer is applied over the first with an opposite pitch, meaning that the two wrappings are applied beginning from opposite ends of the catheter shaft 15. The use of the two layers of tape 24 wrapped from opposing directions results in a strong covering that is resistant to tearing following puncture by the guidewire back end.

While a variety of thin, flexible polymer materials such as polyethylene, polypropylene, polyamide, polyethylene terephthalate, etc. may be used for the tape 24. Porous polymers, optionally provided with a thin, non-porous coating, may be advantageously used because of their excellent flexibility. Tape 24 is most preferably made from a thin porous expanded PTFE (ePTFE) film that has been provided with a porous or non-porous coating of a thermoplastic such as a thermoplastic fluoropolymer, preferably fluorinated ethylene propylene (FEP). ePTFE films are generally made as taught by U.S. Pat. Nos. 3,953,566 and 4,187,390 to Gore. Most preferred ePTFE films for the present application are taught by U.S. Pat. No. 5,476,589 to Bacino. The construction of thin, helically-wrapped tubes from ePTFE films and thermoplastic-coated ePTFE films, and the method of providing the coating onto the ePTFE films, are taught by U.S. Pat. No. 6,159,565 to Campbell et al.

An example of a helically-wrapped catheter shaft as shown by FIG. 2B was made using an FEP-coated ePTFE tape. The tape had a width of about 6 mm and a thickness of about 0.005 mm. The ePTFE had mean fibril length of about 50 microns and a bulk density of about 0.5 g/cc. The ePTFE film was provided with a non-porous coating of FEP on one side. After the coated film was cut into a narrow tape, the tape was helically wrapped onto a stainless steel mandrel of diameter larger that the outside diameter of the chosen catheter shaft. The first layer of the wrapping was applied with the FEP coated side of the tape facing away from the mandrel and the second layer was wrapped in the opposite direction from the first with the coating facing toward the mandrel and first layer. The wrapped mandrel was then heated for about 8 minutes in a convection oven set at 320° C. to melt-bond the helically-wrapped layers of the tube together. Following removal from the oven and cooling to about room temperature, the helically-wrapped tube was removed from the mandrel and fitted over a length of the desired catheter shaft 15 that was shorter than the length of the helically-wrapped tube. The opposite ends of the helically wrapped tube were gripped using pliers and tension was applied to cause the helically-wrapped tube to elongate and reduce in diameter, thereby tightly conforming to the outer surface of the catheter shaft. The ends of the helically-wrapped tube were adhered to the outer surface of the catheter shaft using a cyanoacrylate adhesive. The ends of the covered catheter shaft 15 were then transversely cut to the desired length with a sharp blade. If desired, the hub component typically fitted to the proximal end of the catheter shaft may be fitted over the helical wrap.

The thickness of the thin tubular tape covering 102 was determined to be about 0.012 mm by measuring the diameter of the catheter shaft at 90 degrees to the orientation of the slot 104 using a laser micrometer both before and after the application of the helically-wrapped covering.

The covered catheter 10 that resulted from this process retained the good flexibility of the precursor catheter shaft 15 prior to covering. When a guidewire 19 was inserted into the guidewire lumen 18, the thin cover 102 exhibited good transparency, meaning that the back end of the guidewire 19 was visible to the unaided eye as it passed through the length of the guidewire lumen 18. It was not difficult to stop the progression of the guidewire back end at a desired point along the length of the guidewire lumen, and by bending the catheter with the guidewire slot oriented to the outside of the bend, the covering 102 was readily punctured by the back end of the guidewire 19. When a large portion of the length of the guidewire was pulled through the puncture site, the puncture site exhibited no sign of tearing or of appreciable enlargement of the puncture.

Figure 2C:
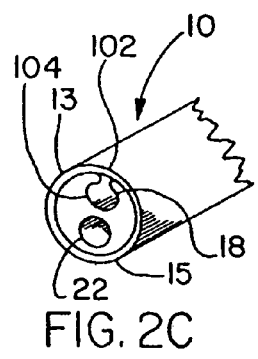
FIG. 2C is a perspective view of the preferred slotted catheter shaft of FIG. 2A provided with a puncturable thin cover in the form of a thin tubular sheath.

FIG. 2C is a perspective view of a catheter 10 including a tubular sheath 13 for use as the thin puncturable cover 102 over slot 104. The sheath may be in the form of a thin extruded tube of, for example, PET. It may be applied similarly to the above-described helically-wrapped tube using a tubular sheath 13 of slightly larger inside diameter than the outside diameter of the catheter shaft 15 to be covered. The outer surface of the catheter shaft 15 may be provided with a thin coating of a suitable adhesive if desired, after which the thin tubular sheath 13 is fitted over the catheter shaft 15 and tensioned to cause it to elongate and reduce in diameter to conform to the outer surface of the catheter shaft 15. Sheath 13 may also be made from a shrink tubing that is heated after being fitted about the outer surface of the catheter shaft 15 to cause it to conform thereto.

Figure 2D:
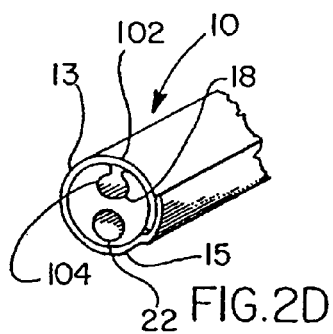
FIG. 2D is a perspective view of the catheter shaft of FIG. 2C wherein the thin tubular sheath is formed by a cigarette wrap.

FIG. 2D is a perspective view of the catheter 10 of FIG. 2C wherein the thin tubular sheath is formed by a cigarette wrap, wherein the braid-covered catheter shaft is additionally covered by an adequately long strip of thin polymeric material that has a width equal to or slightly greater than the circumference of the braid covered catheter shaft. This strip is wrapped around the catheter shaft as shown and adhered by thermal bonding or by the use of a suitable adhesive.

Figure 2E:
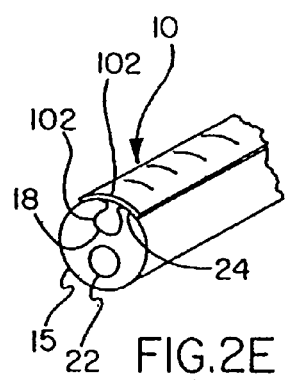
FIG. 2E is a perspective view of the preferred slotted catheter shaft of FIG. 2A provided with a puncturable thin cover in the form of a strip or tape of a polymeric material adhered over the surface of the catheter shaft immediately adjacent to both sides of the slot.
Figure 2G:
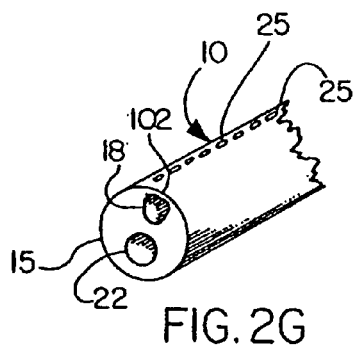
FIG. 2G is a perspective view of an alternative embodiment wherein the thin cover over the guidewire lumen is provided with a multiplicity of pre-formed openings which allow passage of the back end of a guidewire through any opening chosen by the user.
Figure 2F:
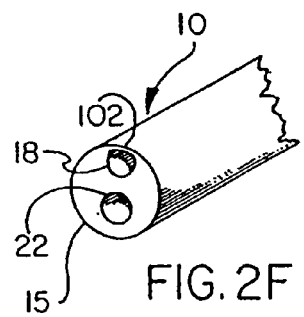
FIG. 2F is a perspective view of an alternative embodiment wherein the puncturable guidewire lumen covering is integral with the catheter shaft.

Another alternative for the puncturable thin cover 102 is shown in the perspective view of FIG. 2E wherein a thin tape 24 is adhered to the outer surface of the catheter shaft 15 adjacent to the edges of slot 104. In another embodiment, the guidewire lumen 18 may be extruded or otherwise formed to have an integral, thin, puncturable covering 102 as shown by the perspective view of FIG. 2F. FIG. 2G is a perspective view of the catheter 10 of FIG. 2F wherein pre-formed openings 25 are formed through the thin puncturable cover 102 to allow passage of the back end of a guidewire through any pre-formed opening 25 chosen by the user. It is apparent that these pre-formed openings 25 may be used with many of the various described embodiments.

Figure 3A:
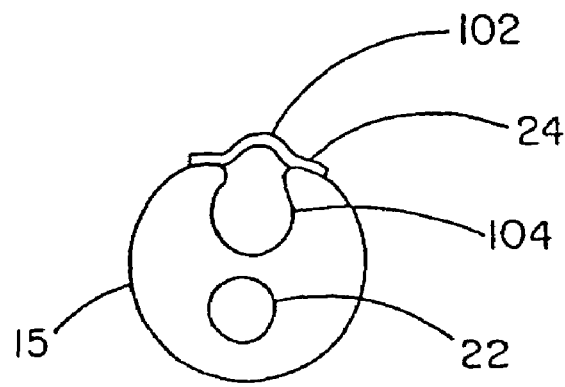
FIGS. 3A-3C are transverse cross sectional views showing variations of the embodiment described by FIG. 2E
Figure 3B:
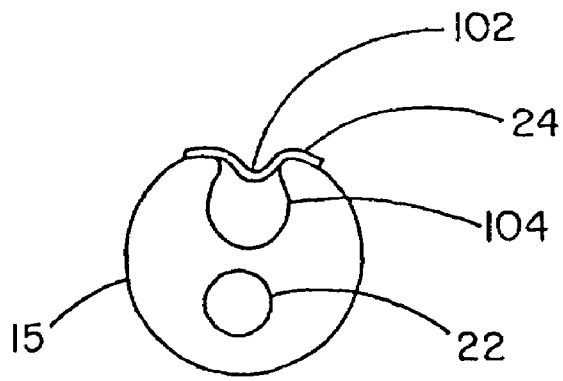
Figure 3C:
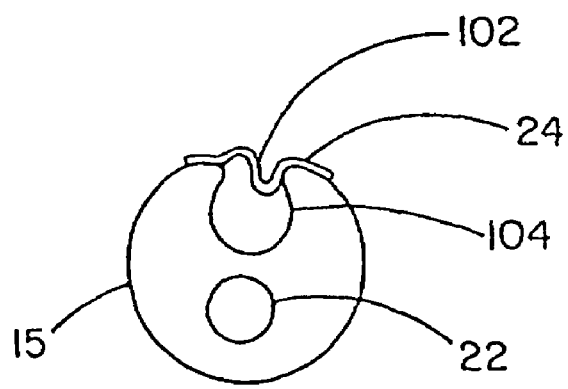

FIGS. 3A-3C show transverse cross sectional views that represent a variation on the embodiment of FIG. 2E. As shown by FIG. 3A, tape cover 24 may be provided so as to increase the space available in the guidewire slot 104 by applying the tape so that it bridges the slot with additional tape width, resulting in the raised aspect shown by this thin puncturable cover 102. This can allow for the use of a larger guidewire if desired. When slot 104 is unoccupied by a guidewire, the thin and flexible tape 24 may take on a non-uniform appearance, giving the guidewire lumen and thin puncturable cover 102 an irregular cross section as shown by FIGS. 3B and 3C. It is apparent that the appearance of each of these three transverse cross-sections may exist at different locations along the length of the same catheter.

The puncturable cover 102 may also be made using threads, wires or other filaments. For example, threads may be wound around a slotted catheter shaft 15 in various desired patterns to form a covering over a guidewire lumen 18 that effectively contains a guidewire 19 but allows the back end of the guidewire to be passed through any of the multiplicity of spaces between adjacent threads of the wrapped covering. The threads may, for example, be provided as a helically-wrapped pattern, a braided pattern or a knit (e.g. warp knit) pattern. By orienting the threads in close proximity to one another, the guide wire will preferentially stay within a lumen of which the thread defines a portion of the wall. However, the end of the wire can be maneuvered to exit this lumen between the threads. By using a wound thread, the structure is never damaged allowing the catheter to be reused multiple times. By controlling the spacing between adjacent threads, the ease of which the end of the wire exits the lumen may be altered. Preferentially, small diameter threads can be used, for example, with diameters from 0.012 to 0.5 mm. Any variety of thread materials may be used, included common thermoplastic (e.g., polyamide, polypropylene, polyester, etc), thermosets, fluoroplastics (e.g., ePTFE) or various metal wires including stainless steels and nitinol.

Figure 4A:
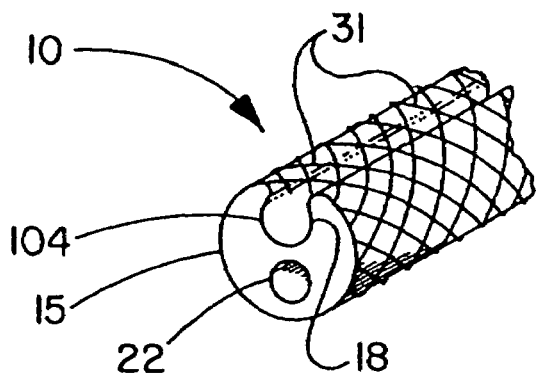
FIG. 4A is a perspective view of the preferred slotted catheter shaft of FIG. 2A provided with a puncturable thin cover in the form of a braid.

As shown by the perspective view of FIG. 4A, a catheter shaft 15 is over-braided with filaments 31. The braid may have numerous configurations including, but not limited to, number of filaments, pick count and pitch angle. As well, filaments 31 may be of various cross sections such as round, square or rectangular.

Figure 4B:
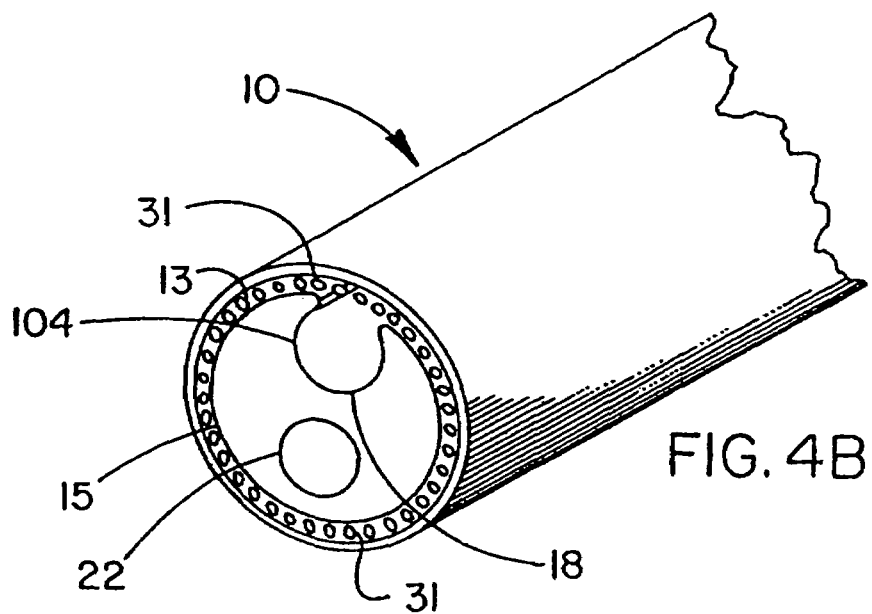
FIG. 4B is a perspective view of the braid-covered catheter shaft of FIG. 3A further provided with a thin exterior tubular sheath over the braid.
Figure 4C:
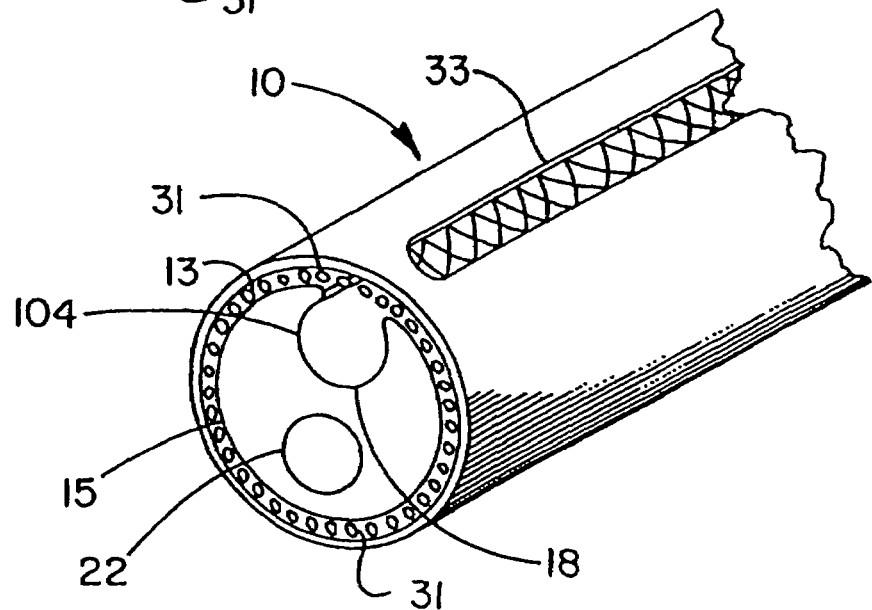
FIG. 4C is a perspective view of the braid-and-sheath covered catheter shaft of FIG. 3B wherein the portion of the sheath covering the catheter slot has been removed.

FIG. 4B shows a preferred embodiment wherein catheter 10 of FIG. 4A is provided with an outer sheath 13 applied over catheter shaft 15 and braid 31 and attached by any of various methods such as heat or adhesive. Following the addition of sheath 13, an appropriately-sized mandrel is inserted into the guidewire lumen 18. The catheter is mounted in a laser (e.g., a 20 watt $CO^2$ laser, Applied Laser Technology, Beaverton Oreg.) with the laser beam directed to slot 104. The laser is used to ablate the polymer material of sheath 13 covering slot 104 along the desired length of the catheter 10, resulting in cutaway slot 33 through sheath 13 exposing slot 104 beneath braid 31. The laser power parameters are such that the polymer material of sheath 13 is ablated yet metallic braid filaments 31 are left undamaged. The indwelling mandrel effectively blocks the laser energy from damaging the opposite side of the catheter shaft 15. The resultant catheter 10 is left with a braided underlying chassis and an outer polymer sheath 13 in which a "strip" of braid is exposed directly above slot 104, whereby guidewire lumen 18 lies immediately below the exposed strip 33 of braid 31. A clinician may then use the back end of a guide wire to part the braid filaments at any suitable user-defined position along this strip 33, thus exiting the guidewire from catheter 10 through the selected interstice of braid 31.

Figure 4D:
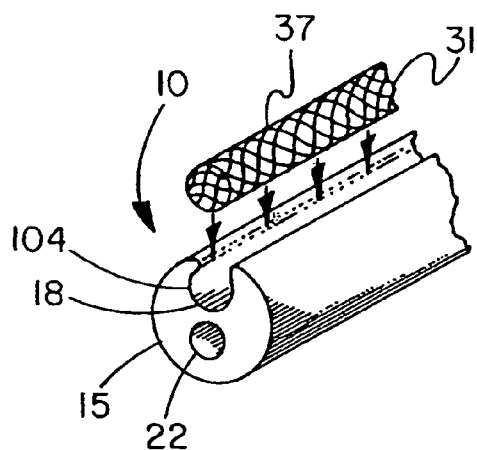
FIG. 4D is a perspective view of catheter shaft with an alternative braid-covered slot wherein a braided tube is fitted and secured into the slot.

FIG. 4D describes an alternative embodiment whereby a braided tube 37 is procured, this tube having an outside diameter corresponding to the inside diameter of slot 104 of catheter shaft 15. The braided tube 37 is made to have a suitable inside diameter to provide adequate clearance for passage therethrough of an intended guidewire. Braided tube is fitted into slot 104 by interference, or by joining with an adhesive. In use, as with the previously described braided construct, the guidewire may be passed through any desired interstice of the braid 31 to exit catheter 10.

Figure 4E:
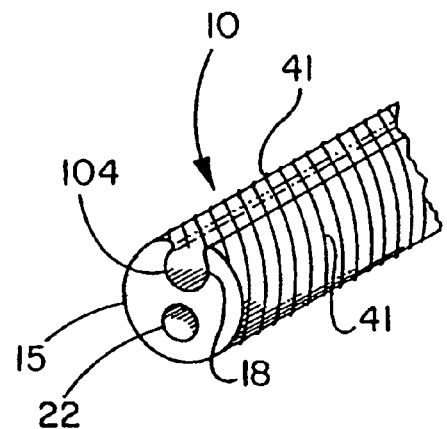
FIG. 4E is a variation of FIG. 4A wherein the braided tubular cover is replaced with a helically wound tubular cover.
Figure 4F:
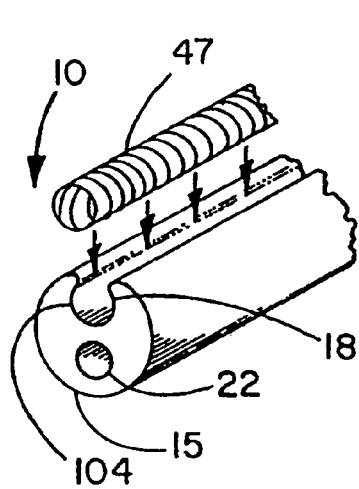
FIG. 4F is a variation of FIG. 4D wherein the braided tube is replaced with a helically wound tube.

FIG. 4E describes a variation of FIG. 4A wherein braid 31 is replaced by helically wound filament 41, which may be of polymeric or metallic material. FIG. 4F shows an alternative to FIG. 4D wherein braided tube 37 is replaced by helically wound tube 47. Again, the helically wound tube may be of polymeric or metallic material. The embodiments of FIGS. 4E and 4F are desirable in that the space between adjacent helical windings will widen when the catheter shaft is bent with the exposed winding on the outside of the bend, making it easier to pass the back end of a guidewire through any desired space between adjacent helical windings.

Figure 4G:
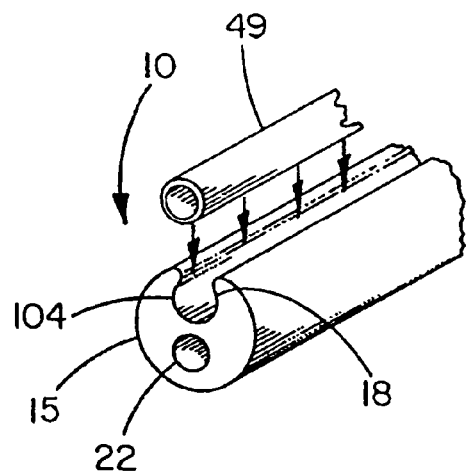
FIG. 4G is a variation of FIGS. 4D and 4F wherein the tubular cover is made from a thin polymeric material.

FIG. 4G is a perspective view of an alternative embodiment to those shown by FIGS. 4D and 4F wherein tube 49 inserted into slot 104 is made from a thin polymeric material. This tube is preferably made by helically wrapping a thermoplastic-coated ePTFE film about a mandrel of suitable size, bonding the wrapping together to result in a cohesive tube, inserting the tube and mandrel into slot 104 and finally removing the mandrel. Alternatively if desired, the mandrel may be removed from within the tube prior to insertion of the tube 49 into slot 104.

Figure 5:
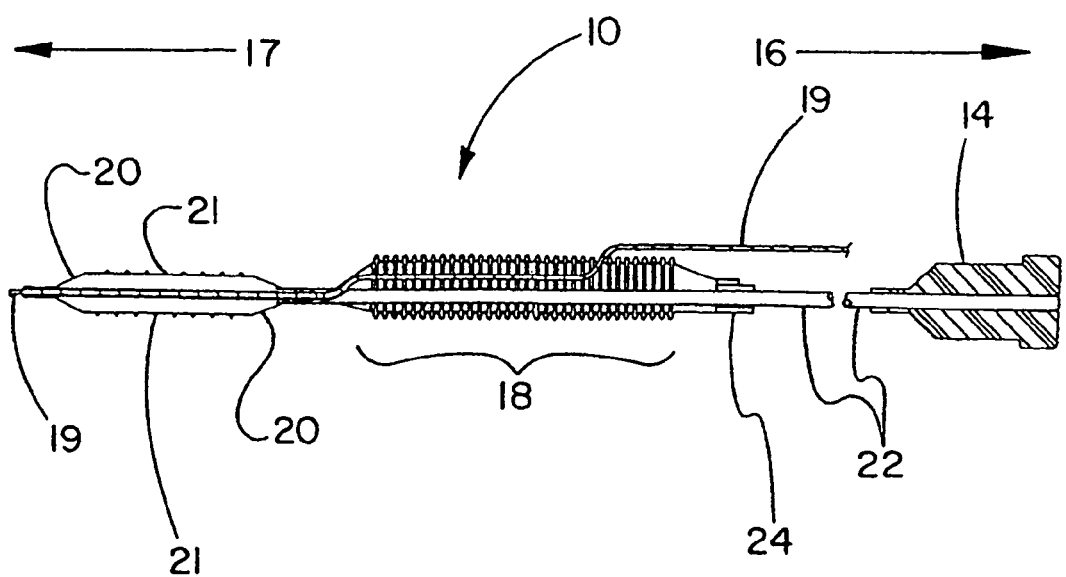
FIG. 5 shows a longitudinal cross section of a basic embodiment of the catheter of the present invention, without a y-fitting but including a hub on the proximal end of the inflation lumen, a puncturable adjustable length guidewire catheter lumen (shown in its axially compressed or shortened state) located distal to the hub and a tubular slider for controlling the proximal end of the adjustable length lumen.

FIG. 5 shows a longitudinal cross section of an alternative embodiment of catheter 10, including a hub 14 on the proximal end 16 of the inflation lumen 22. In this embodiment, catheter 10 is provided with a puncturable adjustable length guidewire lumen 18 that is in the form of a thin tubular sheath 13 puncturable by guidewire 19 as shown. A tubular slider 24 is used in place of a conventional y-fitting, distal to hub 14 for attachment and control of the proximal end of the adjustable length guidewire catheter lumen 18. Adjustable length guidewire catheter lumen 18 is shown in its axially compressed or shortened state. Tubular slider 24 is provided with only a small clearance between the inner diameter of slider 24 and the outer diameter of the inflation lumen 22. Adjustable length guidewire catheter lumen 18 may be made from a variety of thin, flexible polymer materials such as polyethylene, polypropylene, polyamide, polyethylene terephthalate, etc. Porous polymers, optionally provided with a thin, non-porous coating, may be advantageously used because of their excellent flexibility. Adjustable length guidewire catheter lumen 18 is preferably made from a porous expanded PTFE (ePTFE) film that has been provided with a porous or non-porous coating of a thermoplastic fluoropolymer as described previously.

The thin-walled tube is preferably made from an FEP-coated ePTFE film that has been cut into a tape (width, e.g., 12.7 mm) and helically wrapped on a mandrel with the FEP coating placed on the exterior of the wrapping. The helically wrapped tube is then placed into an oven for a suitable time (e.g., 8 minutes in an oven set at a temperature of 320° C.) to thermally bond the overlapped edges of the helical wrapping together, thereby forming a coherent tube. After removal from the oven and cooling, the resulting tube is removed from the mandrel and may be used as the adjustable length lumen component in the catheter of the present invention. The ends of this tube may be joined to the adjacent components by overlapping the tube end over the adjacent component and adhering the overlapped areas with an adhesive such as a cyanoacrylate (e.g., Loctite 401, Rocky Hill, Conn.) or an ultraviolet adhesive (e.g., Loctite 3311). Alternatively, the tube may be everted to orient the FEP-coating toward the lumen, and an adequate heat source may be used to melt-bond the FEP coating to catheter components such as metal hypotubes.

For use as the puncturable, adjustable length lumen tubular component of a catheter, the ePTFE tube may be provided with corrugations (e.g., accordion pleats or folds) with various methods such as those taught by U.S. Pat. No. 3,105,492 to Jeckel and U.S. Pat. No. 6,016,848 to Egres, Jr. Alternatively, it is not required to provide the thin-walled tube with preformed corrugations as, during axial compression from the fully extended length to the shortened, fully compressed length, the tube will wrinkle and corrugate in a non-uniform but entirely suitable manner for use as the adjustable length lumen portion 18 of catheter 10. In another alternative, an elastomer may be used for the adjustable length portion 18 that would be in its relaxed state prior to loading over the guidewire and would extend into a tensioned condition when the distal end of the catheter is advanced.

Longitudinally extruded and expanded tubes of PTFE, that is, seamless ePTFE tubes, may be used in thinwall form as the puncturable, adjustable length guidewire catheter lumen. Under axial compression, the interconnecting fibrils of the node-and-fibril microstructure of ePTFE will progressively bend and fold. This allows the tubular material to axially compress in a substantially uniform fashion, retaining the longitudinal uniformity of the tube wall (macroscopically), without corrugations. This bending of the fibrils within the microstructure of the wall of the ePTFE tube during axial compression is described in U.S. Pat. No. 4,877,661 to House et al. Longer mean fibril length tubes are preferred to maximize the compressible length, e.g., ePTFE tubes of about 50 micron or greater mean fibril length.

A catheter having a puncturable, adjustable length guidewire lumen was constructed using a very thin walled (e.g., 0.03 mm) sheath material. The sheath material is required to be thin enough to corrugate in small folds, allowing the length of the sheath to be reduced to less than 50% of its original length by compressing into the small amplitude folds. A 0.01 mm thick ePTFE film provided with a non-porous FEP coating on one side was chosen for the sheath material. This film was slit to a 6.4 mm width, thereby forming a tape.

An ePTFE tube, having an inner diameter of about 1.6 mm and a wall thickness of about 0.13 mm, was fitted over a 1.6 mm diameter stainless steel mandrel having a length of about 180 cm. The 6.4 mm wide tape was then helically wrapped about the outer surface of the ePTFE tube with a 50% overlap, resulting in a helically-wrapped tube covered with two layers of tape. The resulting assembly was then placed into an air convection oven set at 320° C. for 8 minutes, after which it was removed from the oven and allowed to cool in an ambient environment.

After cooling, the helically-wrapped tube was removed from the mandrel by withdrawing the mandrel from the tube. The end of the extruded tube that had not been helically-wrapped was clamped in a vise. The end of the helical wrapping closest to the vise was simultaneously pinched on opposite sides of the tube using the thumb and forefingers of both hands, and the helical-wrapping was stripped from the underlying ePTFE tube by everting the helically-wrapped tube while pulling it away from the vise.

This thin-walled tube had an approximate wall thickness of 0.03 mm (measured using Mitutoyo Snap Gauge, Model #1 D-C112EBS) and an inner diameter of approximately 1.7 mm (measured using a certified minus pin gauge with a tolerance of 0.01 mm). When this tube was loaded on a 1.2 mm diameter mandrel, it was able to be easily compressed to about 5% of its original length using light digital pressure.

Continuing assembly of the catheter, this sheath was then coaxially mounted over a conventional Percutaneous Transluminal Coronary Angioplasty (PTCA) catheter with a maximum outer diameter proximal of the balloon of less than approximately 0.040" (1.02 mm). The PTCA catheter used was a rapid exchange type, having a proximal guidewire exit port at a location significantly distal of its hub. Prior to mounting the sheath, a 9 Fr (3.0 mm) inner diameter hemostasis y-arm valve (P/N 80348, Qosina, Edgewood, N.Y.) was slid onto the catheter from the catheter's distal end (hemostasis valve oriented away from the back end of the catheter). Next, a female luer (P/N 65206. Qosina, Edgewood, N.Y.) was slid onto the catheter and the luer connection of these two components was engaged. A 2.0 mm inside diameter by 2.1 mm outside diameter 304 stainless steel tube (Microgroup, Medway, Mass.) was then swaged down to approximately 1.4 mm inside diameter by 1.6 mm outside diameter, and then trimmed to a length of approximately 19 mm.

This tube was slid coaxially over the catheter and bonded to the distal end of the female luer with an approximate 6 mm overlap using cyanoacrylate adhesive (Loctite 401, Loctite Corp., Rocky Hill, Conn.). Next, the helically-wrapped sheath described above was slid over the distal tip of the catheter and its proximal end attached by sliding it over the exposed end of the hypotube. These overlapped surfaces were bonded using the cyanoacrylate adhesive, after which 2.3 mm inside diameter polyolefin 2-to-1 shrink ratio shrink tubing was fitted over the junction and heated to conform to the surface of the junction. The distal end of the sheath was then trimmed to a length of approximately 135 cm, equal to the desired working length of the catheter (i.e. length from the distal tip of the catheter to the distal end of the strain relief on the catheter's hub). The distal end of the sheath was then attached at a location approximately 2 mm distal of the proximal guidewire port in the wall of the PTCA catheter. This attachment was made using the cyanoacrylate adhesive between the sheath and catheter, and then over-wrapping this attachment point with cyanoacrylate adhesive and 0.13 mm diameter ePTFE suture (CV-8, WL Gore and Associates, Flagstaff, Ariz.).

To complete the catheter a hemostasis y-fitting was slid distally on the catheter until it was just proximal of the proximal hole of the original PTCA catheter. This compressed the sheath to approximately 15% of its original approximately 135 mm length. A guidewire was then fed into the distal tip of the catheter and carefully threaded through the catheter, including the sheath component, and out from the proximal end of the catheter through the side arm of the y-fitting.

With the guidewire inserted, the user was able to hold the guidewire and hemostasis y-fitting in a fixed position while advancing the distal tip of the catheter relative to the guidewire. Compared to a standard catheter with a proximal guidewire side port fixed distally of the proximal hub, this inventive catheter significantly improved the ability of the section of the catheter, distal to the hemostasis y-fitting, to track the guidewire and allow push forces applied to the proximal portion of the catheter shaft to be transferred directly to the distal tip of the catheter.

Figure 6:
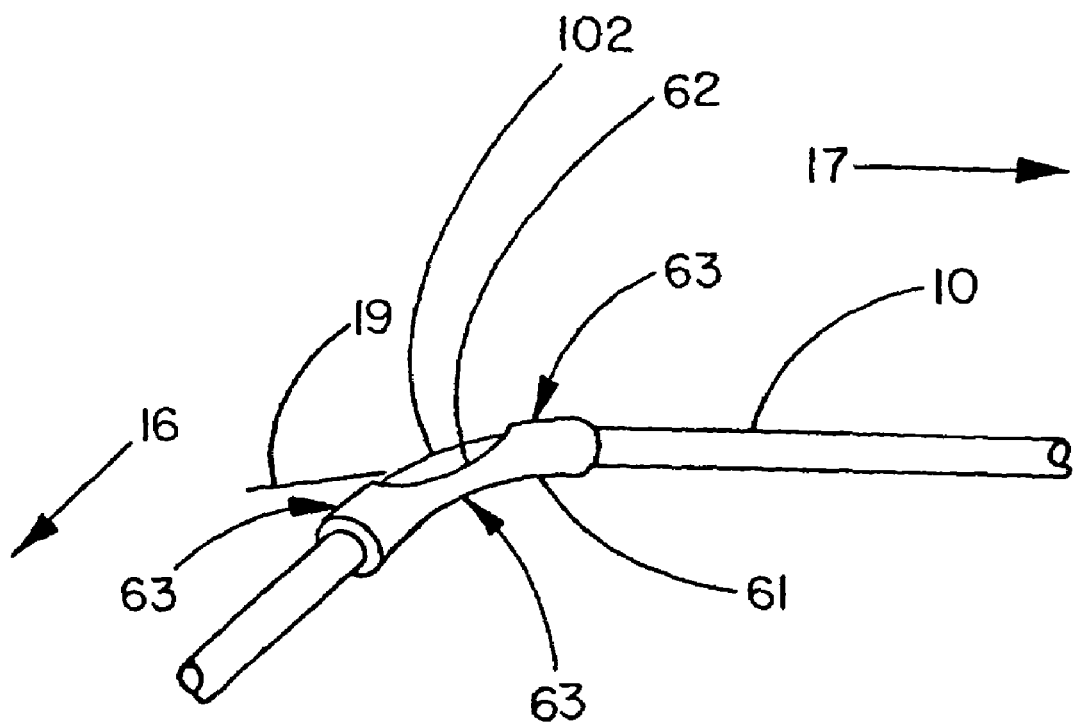
FIG. 6 is a perspective view of a tool useful for bending of the catheter shaft during puncturing of the thin puncturable cover by the back end of a guidewire.

FIG. 6 is a perspective view of catheter 10 in use with a puncturing tool 63 that enables puncturing of the cover 102 by the back end of guidewire 19. While such a tool is deemed unnecessary for many applications, for others it may prove advantageous. As shown, tool 63 is simply a short length of tubing that may be either polymeric tubing or metallic tubing. It is most easily made by bending the short length of tubing (before it is fitted about a catheter) and cutting away a portion of the wall along one side of the tube in the region of the middle of the length of the tube, resulting in opening 62. In use, tool 61 is fitted coaxially about catheter 10 and moved along the length of catheter 10 to the location at which it is desired to puncture cover 102 with the back end of guidewire 19. The tool 61 is oriented so that the opening 62 exposes cover 102 on the side of the catheter where the guidewire is or will be contained. When a guidewire 19 is inserted into the catheter 10 to the location at which it is desired to puncture the catheter, with this location exposed at opening 62 in tool 61, both the catheter 10 and tool 61 are bent as shown by FIG. 6. This bending results in puncturing of cover 102 by the back end of guidewire 19. The bending of catheter 10 is the result of force applied at three points 63, with the middle point being on the inside of the bend along the middle of the length of the bend and the two outer points being on the outside of the bend at the two opposite ends of the bend. It is apparent that the tool may take any suitable form that provides this three point contact during bending wherein the act of bending enables or results in puncturing of cover 102 at the desired location by the back end of guidewire 19. Following puncture, the tool is moved out of the way by sliding it coaxially along the length of the guidewire.

In still a further aspect of the invention, a polymer film wrapping process can be used to construct, modify or enhance the properties of catheters in a variety of ways. Suitable polymer films include, for example, flexible polymer materials such as polyethylene, including ultra-high molecular weight polyethylene, polypropylene, polyamide, polyethylene terephthalate, fluorinated ethylene propylene (FEP), perfluoro alkoxy resin (PFA), polyurethane, polyester, polyimide, etc. Porous polymers, optionally provided with a thin, non-porous coating, may be advantageously used because of their excellent flexibility. The polymer film is most preferably made from a thin, porous expanded PTFE (ePTFE) film that has been provided with a porous or non-porous coating of a thermoplastic such as a thermoplastic fluoropolymer, preferably fluorinated ethylene propylene (FEP). EPTFE films are generally made as taught by U.S. Pat. Nos. 3,953,566 and 4,187,390 to Gore and U.S. Pat. No. 5,476,589 to Bacino. It may be desirable to modify the polymer film material by providing various fillers to the film. In the case of porous polymers such as ePTFE film, fillers can be imbibed into the porosity of the film by known methods, such as taught by U.S. Pat. No. 5,879,794, to Korleski. Suitable fillers include, for example, fillers in particulate and/or fiber form and can be ceramics, metals, metalloids, carbon, and combinations thereof. Particularly useful fillers include, for example, radiopaque materials, such as certain metals (e.g. gold) and carbon. The fillers can be used in combination with desired adhesive materials when imbibed into the porosity of the polymer film. It may also be desirable to metalize the film on at least a portion thereof. Moreover, ePTFE/FEP laminate films are taught in U.S. Pat. No. 6,159,565, to Campbell et al. In an aspect of the invention, the polymer film is provided in a helically-wrapped fashion. In a further aspect of the invention, polymer films which exhibit longitudinal shrinkage (e.g., by heat or chemical activation) may be particularly attractive for use in certain aspects of the invention. Further suitable polymer films can be polymer tubes which may be heat shrinkable materials. One such material is PET shrink tubing, which can be provided in very thin (e.g., 0.5 mil) thicknesses. ePTFE is another example of polymer film (or tubing) that may exhibit shrinkage upon either chemical or heat activation.

It may be desirable to provide a suitable adhesive material to at least a portion of at least one side of the polymer film. Any number of adhesives may be useful according to this aspect of the invention; including thermoplastic adhesives, thermoset adhesives, pressure sensitive adhesives, heat activated adhesives, chemically activated adhesives, and UV-curable adhesives, depending upon the particular embodiment and desired results. The adhesives can be provided in liquid or solid form. In an aspect of the invention, adhesives include, for example, polyamides, polyacrylamides, polyesters, polyolefins (e.g., polyethylene), polyurethanes, and the like.

Figure 7A:
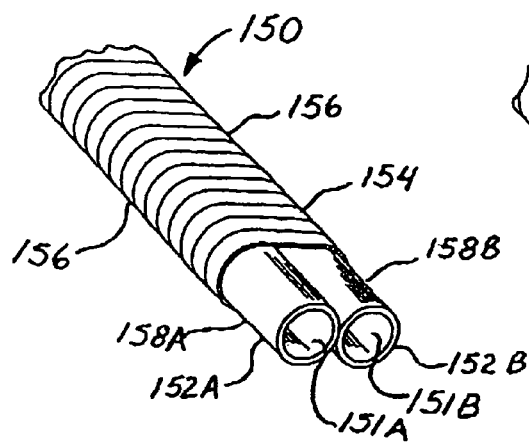
FIG. 7A is a perspective view of a catheter construction according to the present invention, utilizing a polymer film wrap.

Turning to the figures, shown for example in partial isometric FIG. 7A is a general catheter 150 having two longitudinally extending tubular elements 152A and 152B joined together, in an essentially parallel fashion, by an exterior polymer film wrap 154. The tubular elements 152A and 152B can each be provided with lumens (151A, 151B) extending for a portion of, or for the entire length of, the tubular element. This configuration allows two or more simple elements to be joined together to form a more complex assembly such as the double lumen catheter shown in FIG. 7A. Thus by the use of polymer film wrap, a double lumen catheter is formed without the complexity and cost of a typical double lumen extrusion die. Shown in FIG. 7A is polymer film 154 wrapped in an overlapping helical pattern 156. The film 154 is shown in contact with an exterior or outer surface 158A and 158B of the tubular elements 152A and 152B. The polymer film can be provided over a portion of each element, or the polymer film can be provided over the entire length of either or both elements. Tubular elements 152A and 152B can be any longitudinally extending element and each may optionally have at least one lumen extending for at least a portion therethrough. The term "essentially parallel" as applied to more than one longitudinally extending element, includes a "side-by-side" relationship (as shown in FIGS. 7A-7D) as well as configurations that have longitudinally extending elements in a helical or "twisted" relationship. Although any suitable polymer film can be used (such as films comprising the polymers mentioned above) in combination with any suitable adhesive (such as those mentioned above) if an adhesive is desired, ePTFE provided with a coating of FEP is particularly useful. The ePTFE (or other polymer film) can be cut into a tape and wrapped about the elements as shown to secure the elements together. The FEP coating can be either facing toward the elements, away from the elements, or provided on both sides of the ePTFE film. Polymer film wrapping may be particularly desirable when joining together two or more dissimilar materials. For example, when joining together a first tubular element comprising PTFE or polyimide to a second tubular element comprising polyamide (such as PEBAX), the elements may be extremely difficult to join together. A further example includes a first element comprising PTFE and a second element comprising metal. Further variations will be appreciated by the skilled artisan. By providing a polymer film wrap about the outer surfaces of each element, it is possible to obtain a more secure catheter construction. Moreover, parallel elements 152A and 152B can be fused, bonded or adhered together by known means, in addition to being wrapped together with polymer film 154. In an aspect of the invention, parallel elements 152A and 152B can be polymer materials (for example, polyamide, such as PEBAX) which can be heat fused together, preferably after the polymer film 154 is wrapped about the elements. This same heating step could be sufficient to activate the adhesive (if used), or to cause the adhesive to flow, or to cause the polymer film to shrink. Such a heating step can be used in the embodiments described later herein where it may be desirable to heat fuse together two or more polymer elements. Further, although tubular elements 152A and 152B are shown as having substantially the same inner and outer diameters, and as having substantially circular cross sections, it should be understood that the elements can be provided in a variety of sizes and shapes. For example, one element could have a much smaller outer diameter, inner diameter, or both, as compared to the second element. In such a construction the one element could be constructed to have a lumen sized to accept a guidewire in a sliding relationship, while the second element could be sized to have a lumen of sufficient cross section to function as an inflation lumen that terminates at one end into the interior of an inflatable member (which may have a stent mounted thereon) located on the distal end of the catheter. Or, the second element could be sized to have a lumen of sufficient cross-section to allow for advancement and delivery of devices such as self-expanding stents, embolic filters, etc. Moreover, the first element could be relatively shorter in length than the second element, thus producing the well known rapid-exchange type catheter. Further exemplary variations will be recognized by the skilled artisan.

Figure 7B:
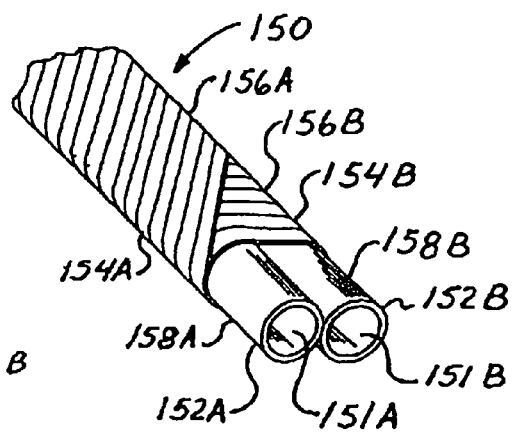
FIG. 7B is a perspective view of a catheter construction according to the present invention utilizing a polymer film wrap.

Shown in partial isometric FIG. 7B is an alternate general catheter 150 wherein two tubular elements 152A and 152B are joined together, in an essentially parallel arrangement, by a series of exterior film wraps. Shown are first and second film wrap layers 154A and 154B respectively, each having an overlapping helical pattern 156A and 156B. As shown in FIG. 7B, the helical pattern of the first film wrap is mirrored or oriented 90° to the helical pattern of the second film wrap. Catheters of the present invention can incorporate one, two, three, four, five, six, seven, eight, nine, ten or more individual layers of film wrappings. Each individual layer of a film wrap can be of the same, a similar, or different pattern and/or be of the same, a similar, or different film material.

Figures 7C, 7D:
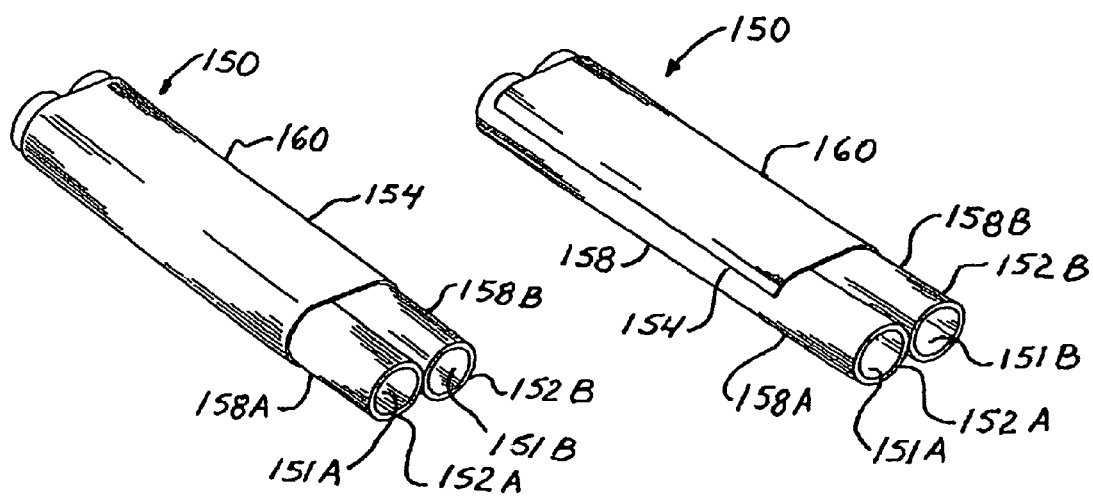
FIG. 7C is a perspective view of a catheter construction according to the present invention utilizing a polymer film wrap.
FIG. 7D is a catheter construction according to the present invention wherein polymer film is contacting the outer surfaces of two longitudinally extending elements.

Shown in partial isometric FIG. 7C is an alternative embodiment of the present invention. Shown is a general catheter 150 having two tubular elements 152A and 152B joined together, in an essentially parallel arrangement, by an exterior film wrap 154 having a longitudinal or "cigarette" pattern 160. The film wrap 154 is shown in contact with an exterior or outer surfaces 158A and 158B of each of tubular elements 152A and 152B and fully encircles (is wrapped about) the two tubular elements. The film wrap 154 can extend for a portion of the length of each element, or the film wrap can be provided over the entire length of either or both elements. Shown in partial isometric FIG. 7D is a similar configuration of a general catheter 150 of the present invention having a polymer film 160 contacting an outer surface 158A and 158B of each element 152A and 152B, but not wrapped about (i.e. fully encircling) the two tubular elements. Again, the polymer film can extend for a portion of the length of each element, or the film can be provided over the entire length of either or both elements.

Numerous shapes, sizes and quantities of tubular elements can be easily joined together by polymer film wrapping to form catheters of the present invention. Shown, for example, in FIG. 8A is a cross-sectional view of a catheter of the present invention having a construction similar to that shown in FIG. 7A or 7C.

Specifically, FIG. 8A is a general catheter 150, formed from two tubular elements 152A and 152B (having lumens 151A and 151B) joined together, in an essentially parallel arrangement, by an exterior film wrap 154. The film wrap is in contact with the exterior surfaces 158A and 158B of the tubular elements.

The term "tubular element" includes any longitudinally extending structure with or without a through lumen. Thus, tubular elements include but are not limited to tubes with lumens, solid rods, hollow or solid wires (e.g., guidewires), hollow or solid stylets, metal tubes (e.g., hypotubes), polymer tubes, pull cords or tethers, fibers, filaments, electrical conductors, radiopaque elements, radioactive elements and radiographic elements. Tubular elements can be of any material and can have any cross-sectional shape including but not limited to profiles that are circular, oval, triangular, square, polygon shaped or randomly shaped.

Shown in FIG. 8B is a general catheter 150, formed from two tubular elements 152A and 152B (having lumens 151A and 151B) joined together by an exterior polymer film wrap 154. Positioned within the void space between the tubular elements is a solid tubular element 162. Tubular element 162 can be for example a guidewire or a stiffening stylet. Tubular element 162 can be free to translate longitudinally within the void space lumen or may be fixed to the catheter assembly by adhesives or by frictional interference. Polymer film 154 may be puncturable by the end of the guidewire to allow a physician to choose a suitable guidewire exit port at virtually any point along the length of the catheter, if desired.

Moreover, polymer film wrapping can be used to form catheters having similar profiles as those shown in FIGS. 2B through 2F. For example, shown in FIG. 8C is a general catheter 150 formed from a first tubular element 152 having lumen 151A, a second "skived" tubular element 164 having lumen 151B and a polymer film wrap 154. The polymer film wrap 154 is in contact with an exterior surface 158A and 158B of both tubular elements 152 and 164 respectively. Tubular elements having essentially unsupported or collapsible profiles (such as element 164) can be supported, for example, by a mandrel during polymer film wrapping or during subsequent processing. Lumen 151b can be a guidewire lumen, wherein polymer film wrap 154 can be easily punctured by a guidewire end, as discussed above, to allow a physician to choose a guidewire exit port along the length of the catheter.

A further aspect of the present invention is depicted in FIG. 8D. Shown is a general catheter 150 formed from a first, hollow tubular element 152 having lumen 151, a second tubular element 162 and a polymer film wrap 154. The polymer film wrap 154 is in contact with exterior surfaces 158A and 158B of both tubular elements 152 and 162. Tubular element 162 can be free to translate longitudinally within the void space lumen (e.g., to function as a guide wire) or may be fixed to the catheter assembly by adhesives or by frictional interference (e.g., to function as a stiffening stylet). Polymer film wrap 154 may be puncturable by the end of a guidewire to allow a physician to choose a suitable guidewire exit port along the length of the catheter.

Shown in FIG. 8E is a cross-sectional profile of a general catheter 150 of the present invention formed from a first tubular element 152 having lumen 151A, a second "D-shaped" tubular element 166 having lumen 151B and polymer film wrap 154. The polymer film wrap 154 is in contact with exterior surfaces 158A and 158B of both tubular elements 152 and 166.

Shown in FIG. 8F is a cross-sectional profile of a general catheter 150 of the present invention formed from first, second and third tubular elements 152A, 152B, and 152C (having lumens 151A, 151B, and 151C) and polymer film wrap 154. The polymer film wrap 154 is in contact with exterior surfaces 158A, 158B, and 158C of all three tubular elements 152A, 152B, and 152C. Also shown in FIG. 8F is a circular or smooth luminal surface 168, a "non-smooth", fluted luminal surface 170 and three void spaces 172. A void space 172 can be optionally used as a fluid communication path or guidewire lumen along at least a portion of a length of a general catheter 150.

Figure 9A:
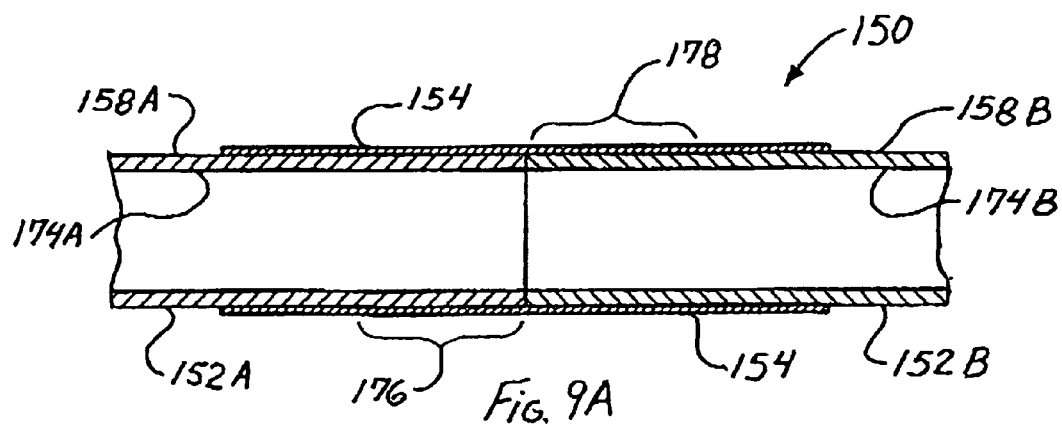
FIG. 9A is a cross-section of a catheter construction according to the present invention.

In a further aspect, an exterior polymer film wrap can be used to secure, provide strain relief or join tubular elements together to form various catheter constructions. Shown for example in partial cross-sectional view FIG. 9A is a first longitudinally extending tubular element 152A having a through lumen 174A, an exterior outer surface 158A and a distal region 176. Also shown is a second longitudinally extending tubular element 152B having a through lumen 174B, an exterior outer surface 158B and a proximal region 178. The distal region 176 of the first tubular element 152A is in contact with or joined to the proximal region 178 of the second tubular element 152B in an abutting relationship wherein the lumen 174A is in fluid communication with the lumen 174B. An external polymer film at least partially covers and is in contact with the outer surfaces 158A and 158B of both tubular elements 152A and 152B along the joined region. The polymer film 154 can provide a strain relief to enhance the flexural and fatigue properties of the joined tubular elements. Further, it can be designed to increase burst strength or tensile strength without significantly changing flexibility of the catheter. Moreover, the two tubular elements can be adhered together using adhesives, fuse bonding, melt bonding, or other suitable means in addition to providing the polymer film. The polymer film layer 154 may also serve as a "fail-safe," should an underlying bond fail. Polymer film can be selected so that the polymer film tensile strength is many times that of the catheter components or the bond zone strength. The polymer film is preferably wrapped about the two tubular members, using one of the techniques described above. Moreover, either or both of the tubular elements can be provided with further lumens, which can also be in fluid communication with a corresponding lumen in the other tubular element. For example, each of the first tubular element 152A and the second tubular element 152B can be provided with a first through lumen and a second through lumen. The first through lumen of each element can be in fluid communication with each other and the second through lumen of each element can be in fluid communication with each other. The first through lumens can be sized to accept a guidewire in a sliding relationship and the second through lumens can be sized to deliver inflation fluid to an expandable member located on the distal end of the catheter, or to deliver any number of devices, medications, etc., to a treatment site.

Figure 9B:
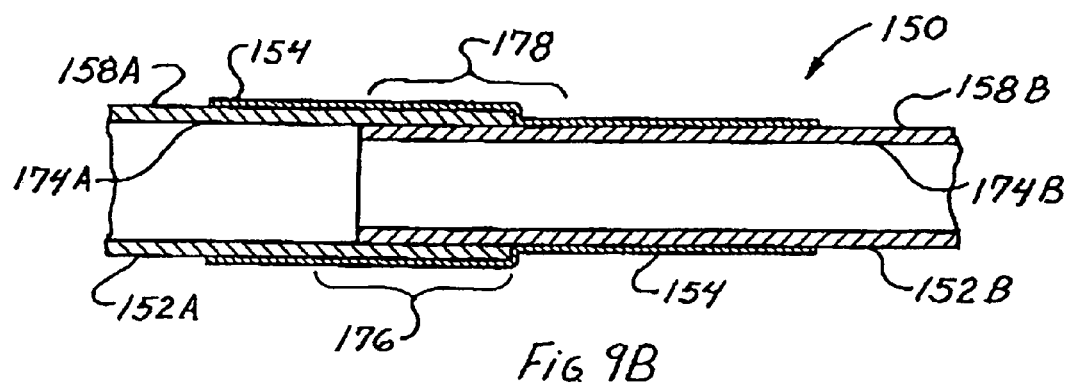
FIG. 9B is a cross-section of a catheter construction according to the present invention.

In an alternate configuration, tubular elements can be similarly joined together in an overlapping relationship. Shown in partial cross-sectional view, FIG. 9B is a first longitudinally extending tubular element 152A having a through lumen 174A, an exterior outer surface 158A and a distal region 176. Also shown is a second longitudinally extending tubular element 152B having a through lumen 174B, an exterior outer surface 158B and a proximal region 178. The distal region 176 of the first tubular element 152A overlaps the proximal region 178 of the second tubular element 152B. An external polymer film 154 at least partially covers and is in contact with the outer surfaces 158A and 158B of both tubular elements 152A and 152B along the joined region. The polymer film layer 154 can provide a strain relief to enhance the flexural and fatigue properties of the overlapping tubular elements. Further, it can be designed to increase burst strength or tensile strength without significantly changing flexibility of the catheter. Moreover, the two tubular elements can be adhered together using adhesives, melt bonding, or other suitable means in addition to providing the polymer film. The polymer film layer 154 may also serve as a "fail-safe," should an underlying bond fail. Polymer film can be selected so that the polymer film tensile strength is many times that of the catheter components or the bond zone strength. The polymer film is preferably wrapped about the two tubular members, using one of the techniques described above.

Figure 9C:
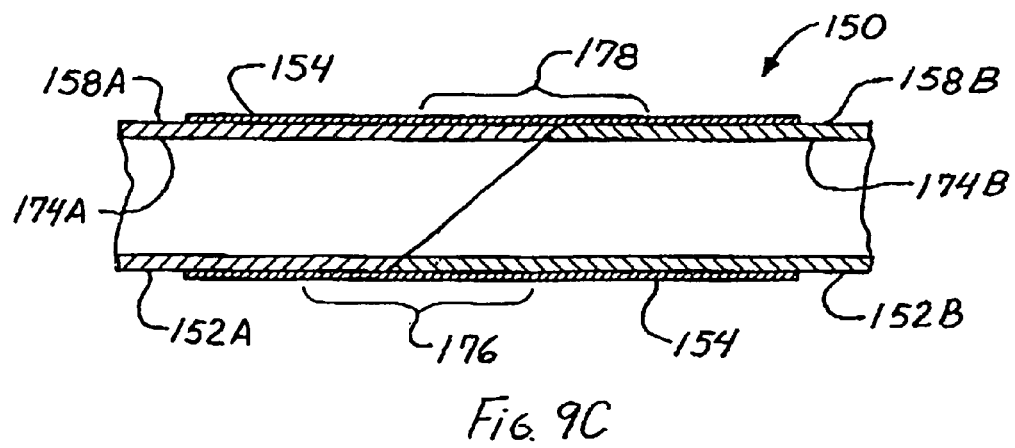
FIG. 9C is a cross-section of a catheter construction according to the present invention.

Shown in FIG. 9C are two tubular elements joined in a skived or lap joint configuration. Shown is a first longitudinally extending tubular element 152A having a through lumen 174A, an exterior outer surface 158A and a distal region 176. Also shown is a second longitudinally extending tubular element 152B having a through lumen 174B, an exterior outer surface 158B and a proximal region 178. The distal region 176 of the first tubular element 152A is in contact with or joined to the proximal region 178 of the second tubular element 152B. An external polymer film at least partially covers and is in contact with the outer surfaces 158A and 158B of both tubular elements 152A and 152B within the joined region. The polymer film 154 provides a strain relief to enhance the flexural and fatigue properties along the lap joint. Moreover, the two tubular elements can be adhered together using adhesives, fuse bonding, melt bonding, or other suitable means in addition to providing the polymer film. The polymer film is preferably wrapped about the two tubular members, using one of the techniques described above.

Figure 10:
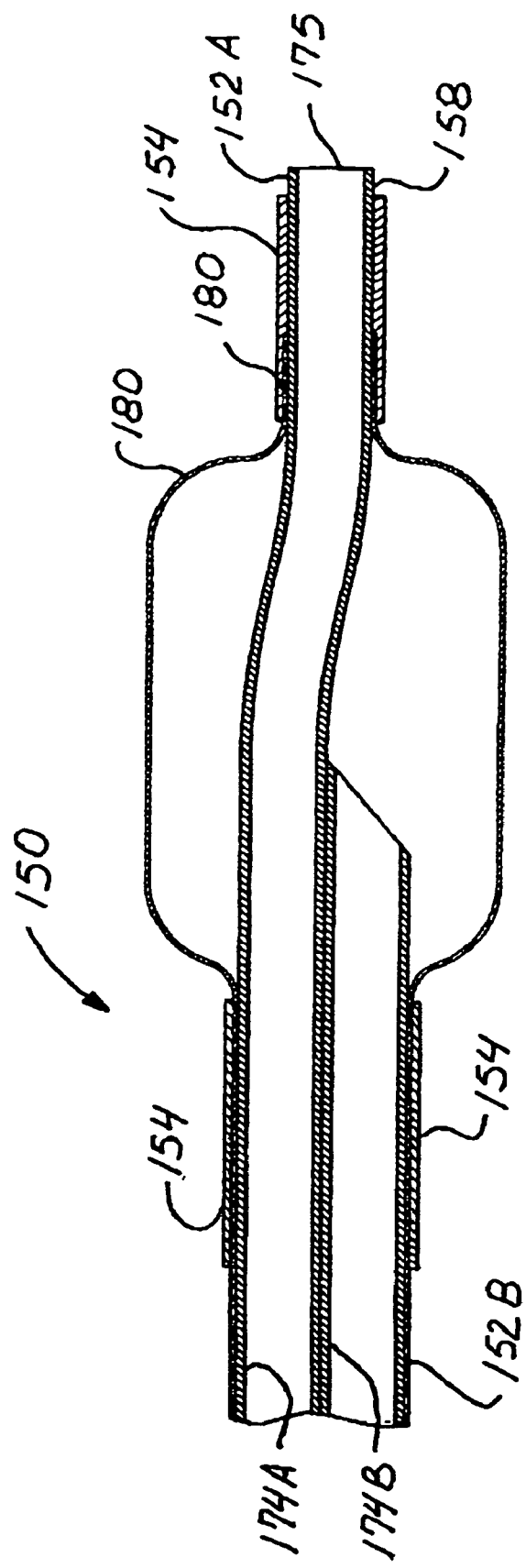
FIG. 10 is a cross-section of a catheter construction according to the present invention.

A film wrapped external layer can be used to secure individual components onto a tubular member to form catheters of the present invention. Shown for example in partial cross-sectional view, FIG. 10 shows a first longitudinally extending tubular element 152A having an outer surface 158 and a lumen 174A. A balloon or second element 180 is in contact with the outer surface 158 of the distal section of the first tubular element 152A. A polymer film 154 is shown in contact with the outer surface 158 of the distal section of the first tubular element 152A and in contact with the outer surface of the distal section of balloon 180. Also shown is a third element or longitudinally extending tube 152B having a lumen 174B. Polymer film 154 is shown in contact with the outer surface of the proximal section of the balloon 180. Preferably polymer film 154 is wrapped about the outer surface of the proximal section of the balloon 180. Polymer film 154 can also be in contact with the outer surfaces of first tubular element 152A and third element 152B at sections proximal to balloon 180. Polymer film 154 can also extend from the balloon 180 to the proximal end of the catheter 150, or to any point proximal to the balloon 180. The lumen 174A of first longitudinally extending tubular element 152A is configured as a guidewire lumen having a distal guidewire exit port 175 and the lumen 174B of the third element 152B is configured as an inflation lumen with its distal end terminating in the interior of the balloon 180. Moreover, first tubular element 152A can be the length of the catheter and have a proximal guidewire exit port (not shown), as well as any number of guidewire exit ports located distal to the proximal end of the catheter and proximal to the proximal end of balloon 180. Of course, first tubular element 152A may also terminate at a point distal to the proximal end of the catheter, thus being configured as the well known rapid exchange type catheter. The balloon 180 can be any suitable construction. For example, the balloon 180 can be formed by film wrapping that, in addition to forming a balloon, is used to secure two or more tubular elements together in a fashion depicted in FIGS. 7A-D and 8A-F. Moreover, the distal end of inner surfaces of the balloon 180 can be sealed to the outer surface 158 of first tubular element 152A, and the inner surfaces of the proximal end of balloon 180 can be sealed to the outer surfaces of the first tubular element 152A and third element 152B by any suitable means, such as by adhesives, fuse bonding, heat bonding, etc. Polymer film 154 can then be provided to (preferably wrapped about) at least one of the distal end and the proximal end of the balloon 180, to, for example, further secure the balloon 180 to the catheter.

Figure 11:
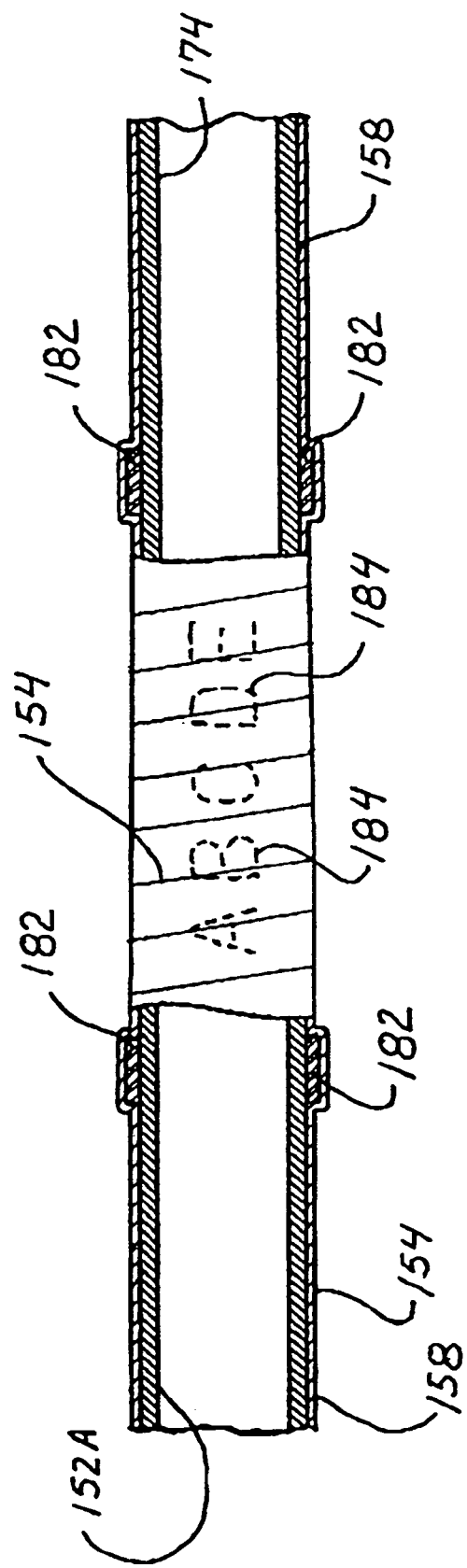
FIG. 11 is a partial cross-section and perspective view of a catheter according to the present invention.

In addition to securing multiple tubular elements or balloons, polymer film can be used to secure or cover various secondary components to form catheters of the present invention. These secondary components or elements include but are not limited to radiopaque elements, visualization elements (such as indicia), radioactive elements, chemical eluting elements, electrical components, valves, seals, occluders, filters, membranes, members used to alter or enhance mechanical properties, historic indicators of use, temperature or sterilization, fluid fittings and interconnect hubs. Shown for example in partial cross-sectional view, FIG. 11 shows a first longitudinally extending tube 152A having an outer surface 158 and a lumen 174. A second element, in this case radiopaque marker bands 182, are in contact with the outer surface 158 of the first tubular element 152A. A polymer film 154 is shown in contact with the outer surface 158 of the first tubular element 152A covering the second elements 182. Also shown is a visualization marking or label 184 that is in contact with the outer surface of the first tubular element 152A. The visualization marking or label (i.e; indicia) 184 is covered by a polymer film 154 that is in contact with the marking 184 and the outer surface 158 of the first tubular member. Transparent or opaque polymer films can be used to secure or cover various secondary components. Other secondary elements can be covered or secured by film layers by constructions similar to those depicted in FIGS. 10 and 11.

Figure 12:
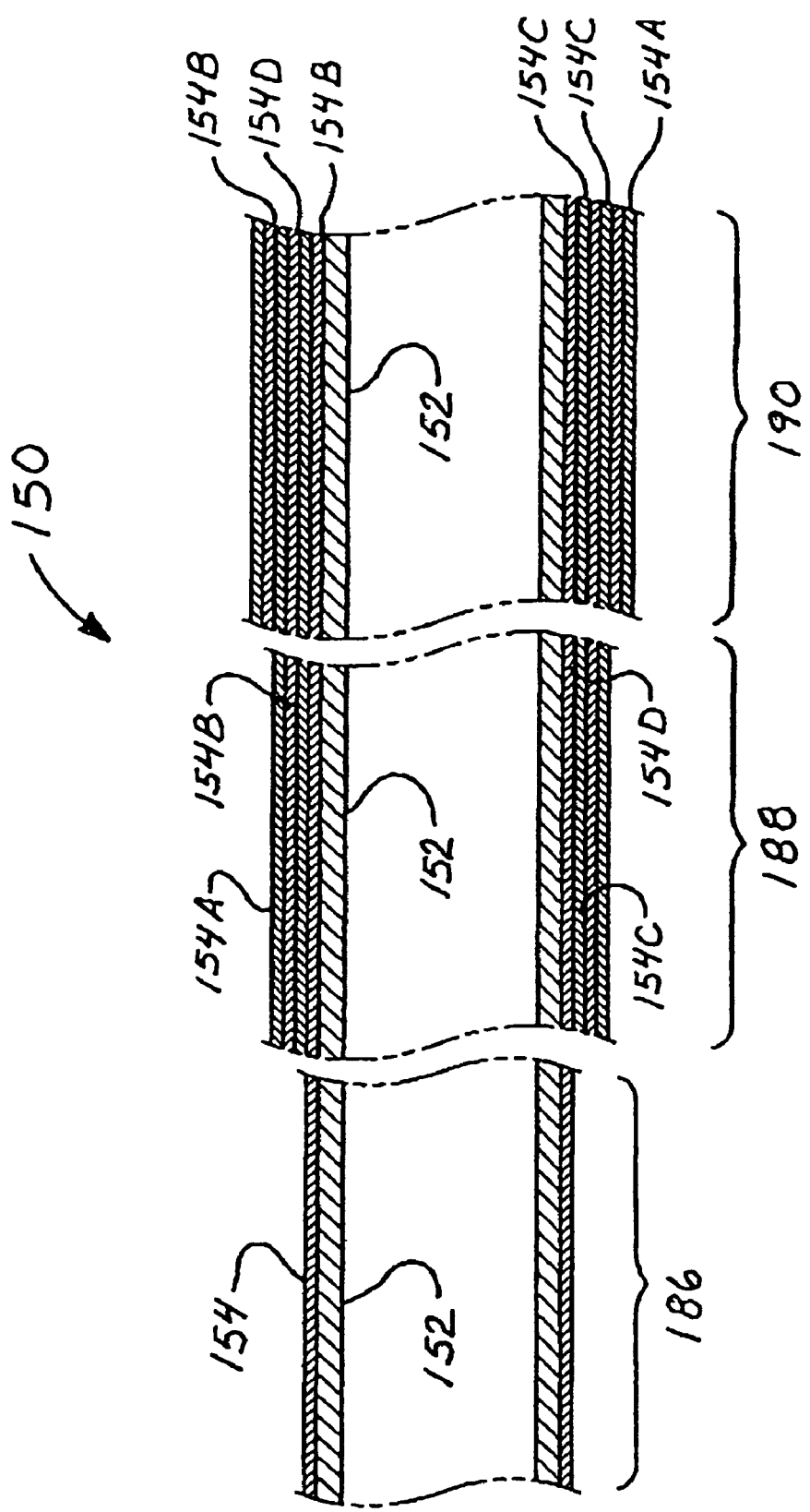
FIG. 12 is a cross-section of a catheter according to the present invention.

Film wrapping processes can be used to construct an entire catheter tube or be used to modify the properties of a catheter tube from a proximal point to a distal point on the tube. The same polymer materials discussed above are suitable for this aspect of the invention as well. Shown for example in partial cross-sectional view in FIG. 12 are three cross-sectional regions 186, 188 and 190 of a single general catheter 150. The three regions can have different physical properties due to the different film wraps applied to each region. Shown in cross-sectional region 186 is an elongated tubular element 152 having a single film layer 154 wrapped about the tubular element. Similarly shown in cross-sectional region 188 is an elongated tubular element 152 having four individual film layers 154A, 154B, 154C and 154D wrapped about the tubular element. Also shown in cross-sectional region 190 is an elongated tubular element 152 having six individual film layers 154A, 154B, 154C, 154D, 154E and 154F wrapped about the tubular element. Each region can be tailored, by altering the individual film layers, to have desired mechanical characteristics such as flexibility, column or compression strength, tensile strength, crush resistance, burst strength, wall thickness, torsional strength, lubricity, etc. These different mechanical properties can be controlled by varying the number of film layers, by varying the film wrap pattern or by varying individual film properties such as film material, film thickness, film strength or film orientation. A general catheter according to this aspect of the invention can have, for example, a relatively stiff proximal region transitioning to an intermediately stiff transition region that transitions to a relatively flexible distal region. Furthermore, polymer film can be wrapped about a catheter in discreet locations to be located near both ends of an implantable device, such as an expandable stent, to constrain the device and/or prevent longitudinal expansion of, for example, the stent. Moreover, the polymer film could be wrapped in a layered manner to provide a smooth transition from the outer surface of the catheter to the stent on either side of the stent. Catheter tubes according to this aspect of the invention can be constructed entirely from film wrappings or can be formed by wrapping film about any elongated tubular structure, such as a polymer extrusion, hypotube, etc.

Figure 13:
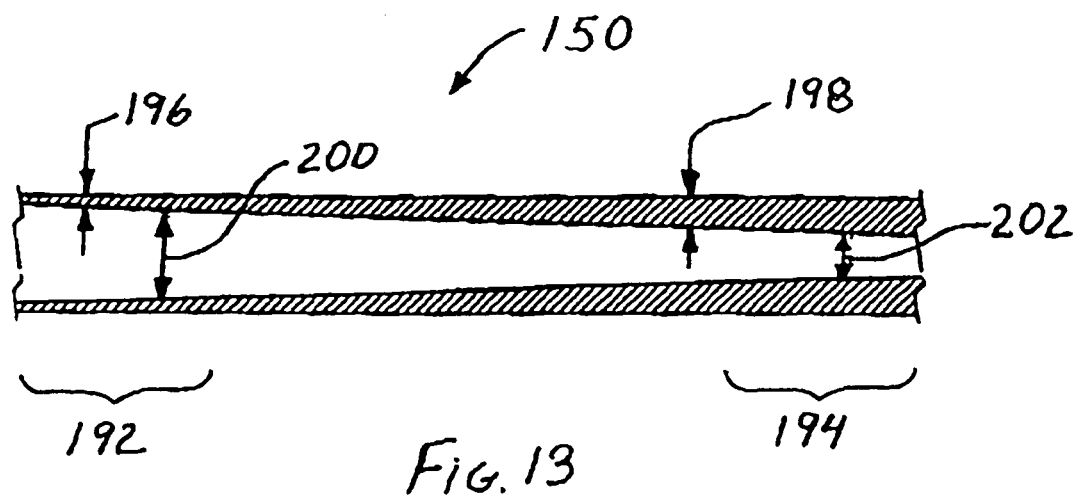
FIG. 13 is a cross-section of a catheter according to the present invention.

Catheters can be constructed having physical attributes that vary by distinct regions or can display a progressive or continuous gradient in physical properties. Shown for example in partial cross-section view FIG. 13 is a general catheter 150 having a first end region 192 and a second end region 194. The first end region 192 has a wall thickness 196 that is less than the wall thickness 198 of the second end region 194. In addition, the first end region 192 has a inner dimension 200 that is greater than the inner dimension 202 of the second end region 194. Such dimensions can be altered by progressively varying the number of film layers, by progressively varying the film wrap pattern or by progressively varying individual film properties (such as thickness) along the length of the catheter. In an alternate embodiment, catheters of the present invention can have variable properties by discrete or "step" variance in the film application. Furthermore, catheters can be formed having essentially constant inner diameters (IDs), outer diameters (ODs), and/or wall thickness, but longitudinal properties can be varied by using different film materials over the length of the catheter.

Figure 14:
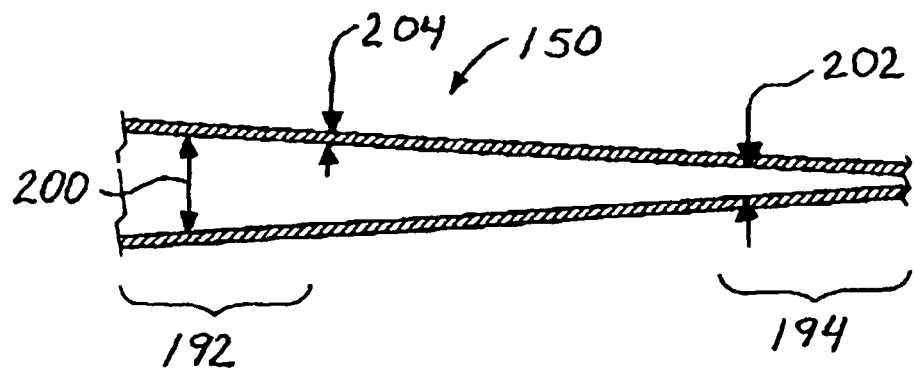
FIG. 14 is a cross-section of a catheter according to the present invention.

Film wrapping processes are ideally suited for forming tubular elements with "non-linear" profiles such as tapers, flares, an "egg in a snake" bulge, square to round (profile 1 to profile 2) shapes, large to small diameters or any other, "generally non-extrudable" profile. Shown for example in partial cross-sectional FIG. 14 is a general catheter 150 of the present invention having a first end region 192 and a second end region 194. The first end region 192 has a inner dimension 200 that is greater than the inner dimension 202 of the second end region 194. The general catheter has a wall thickness 204 that is essentially uniform along the longitudinal length.

Catheter profiles, such as the tapered profiles shown in FIGS. 13 and 14 can be constructed by film wrapping over a tapered or non-linear mandrel. Preferably, the film is an expanded fluoropolymer (e.g., ePTFE) that has a thermoplastic coating (e.g., FEP) applied to an external surface of the film. The film can be wrapped about the mandrel with the thermoplastic coating facing outwards. The thermoplastic coating can be melted to adhere the film wrap together on the outside surface, leaving an inner, lubricious surface on the inner surface of the catheter component. The catheter component can then be removed from the mandrel. One skilled in the art will now understand the various catheter configurations which can be constructed using this film wrapping procedure. One advantage to using this procedure is the ability to easily construct tubular elements with incredibly tight wall thickness tolerances, as compared to forming tubular elements by an extrusion process. Polymer films—particularly ePTFE films—can be produced in extremely thin films with very little thickness variance across the film. Thus, by wrapping such a film about a mandrel, tubes with tightly controlled wall thicknesses can be easily produced. Moreover, tube concentricity can also be easily and tightly controlled using such a film wrap process.

Figure 15A:
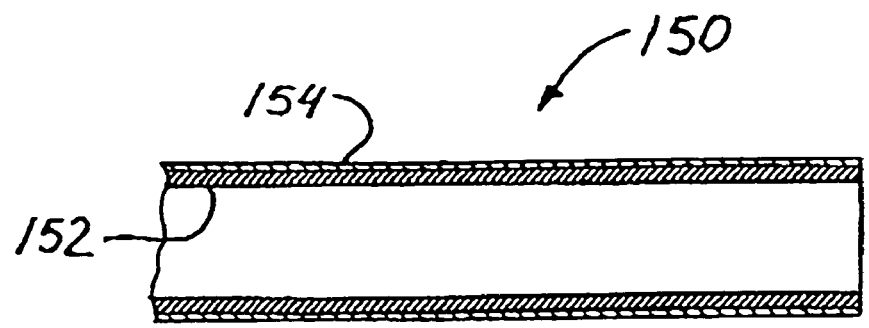
FIG. 15 is a cross-section of a catheter according to the present invention.
Figure 15B:
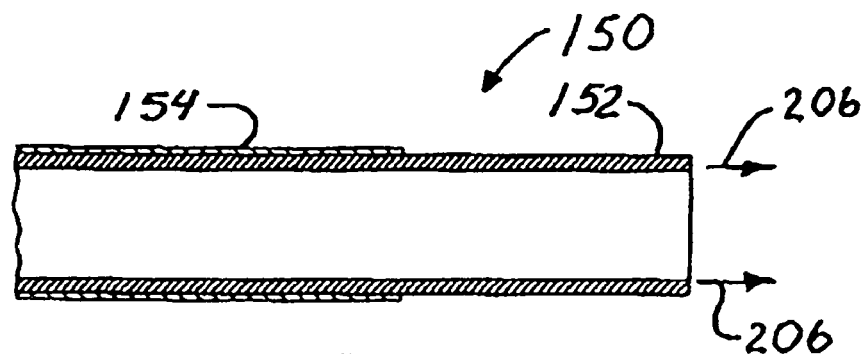
Figure 15C:
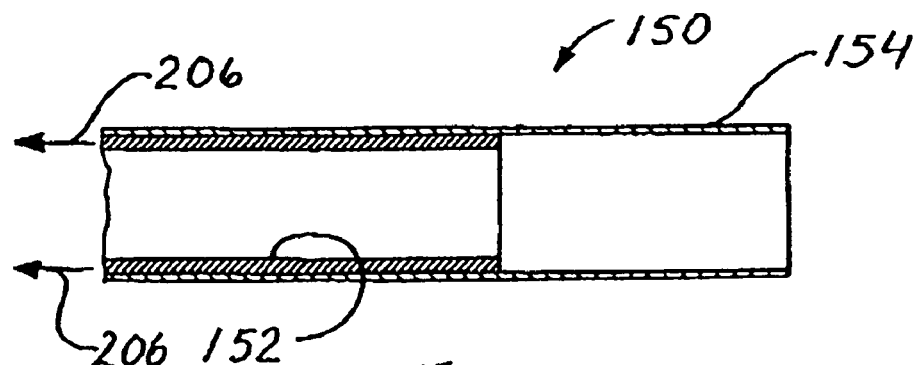

Film wrapping processes can also be used to form tubular members that have a longitudinal sliding relationship. For example as shown in partial cross-sectional view FIG. 15A is a general catheter 150 of the present invention having a longitudinally extending tubular element 152 with a film wrapped external layer 154. In an aspect of the invention, the film 154 is an expanded fluoropolymer (e.g., ePTFE) and has a thermoplastic coating (for example FEP) applied to an external surface of the film. Thus the film can be wrapped over the tubular element 152 with the thermoplastic coating facing outwards. The thermoplastic coating can be melted to adhere the film wrap together on the outside surface leaving an inner lubricious surface (the expanded fluoropolymer) that does not adhere to the longitudinally extending tubular element 152. Since the film covering 154 is not adhered to the tubular element 152 the two components can be free to move longitudinally relative to each other. In addition a sealed or "zero-clearance" fit between the tube and the film can be produced by the film wrap. Shown in FIGS. 15B and 15C are examples of such a sliding fit between a base tube 152 and an external film wrap 154. Shown are longitudinal relative motions 206 between the base tube 152 and the external film wrap 154.

Figure 16A:
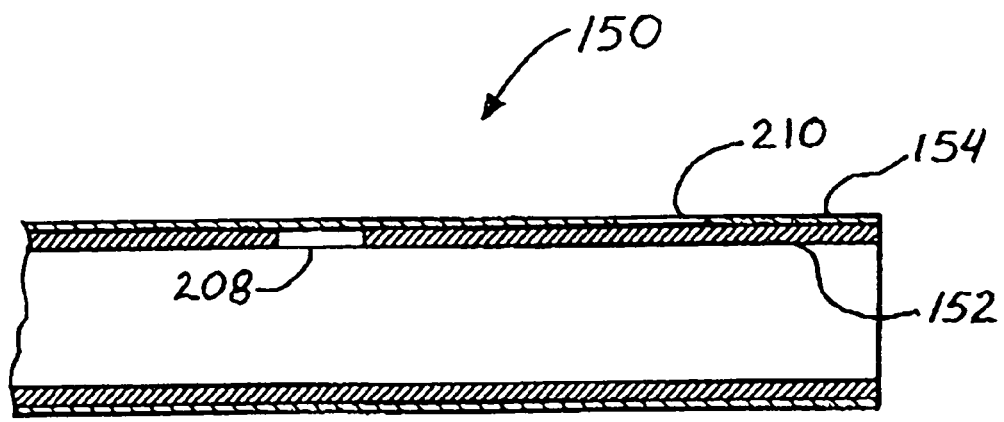
FIG. 16 is a cross-section of a catheter according to the present invention.

In a preferred embodiment, a general catheter of the present invention has a longitudinally sliding fit between a base tube and an external film layer that forms a sliding "gate-valve". Shown in partial cross-sectional view FIG. 16A is a general catheter of the present invention 150 having a longitudinally extending tubular element 152 covered by a film layer 154. The longitudinally extending tubular element 152 has a first port 208 and the film layer 154 has a second port 210. The ports are shown in a longitudinally separated position, so that the valve is "closed".

Figure 16B:
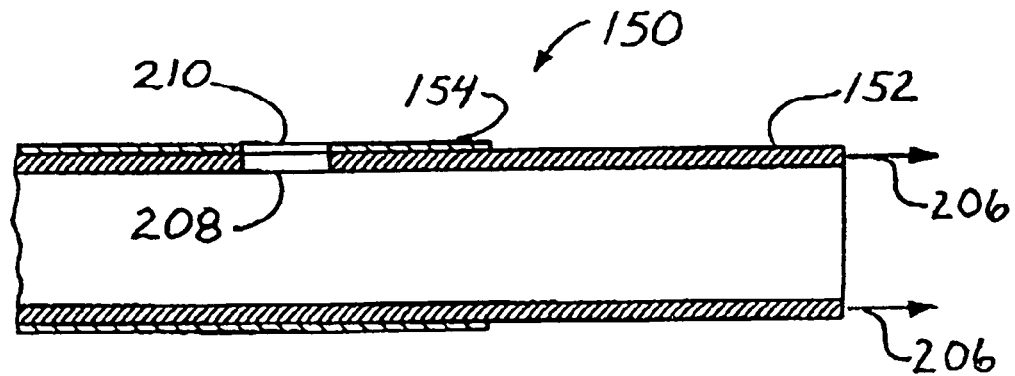

Shown in partial cross-sectional view FIG. 16B is a general catheter of the present invention 150 having a longitudinally extending tubular element 152 covered by a film layer 154. The longitudinally extending tubular element 152 has a first port 208 and the film layer 154 has a second port 210. When the tubular element 152 is longitudinally translated 206, the ports 208 and 210 become aligned as shown, so that the valve is "opened". Of course, each of the tubular element 152 and the film layer 154 can be provided with more than one port.

Figure 17:
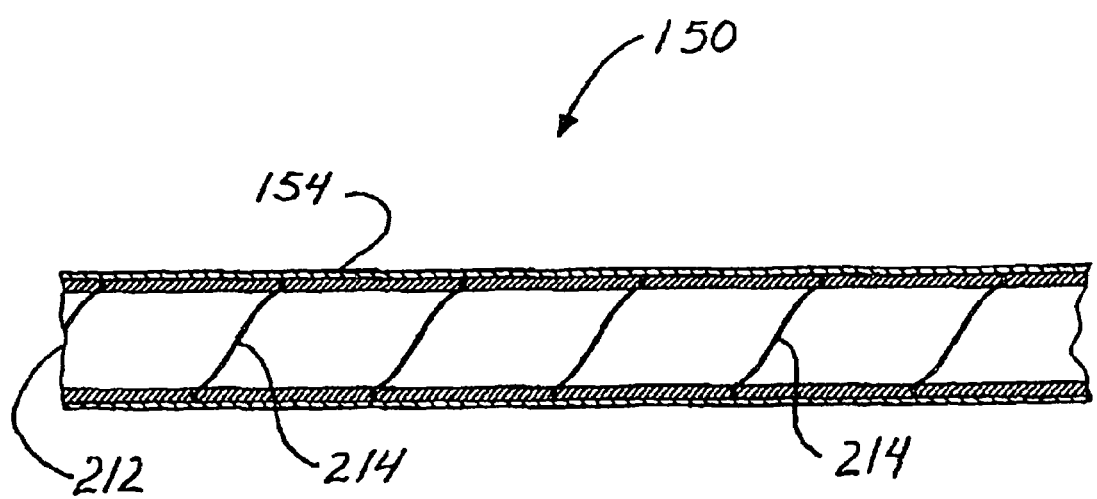
FIG. 17 is a cross-section of a catheter according to the present invention.
Figure 18A:
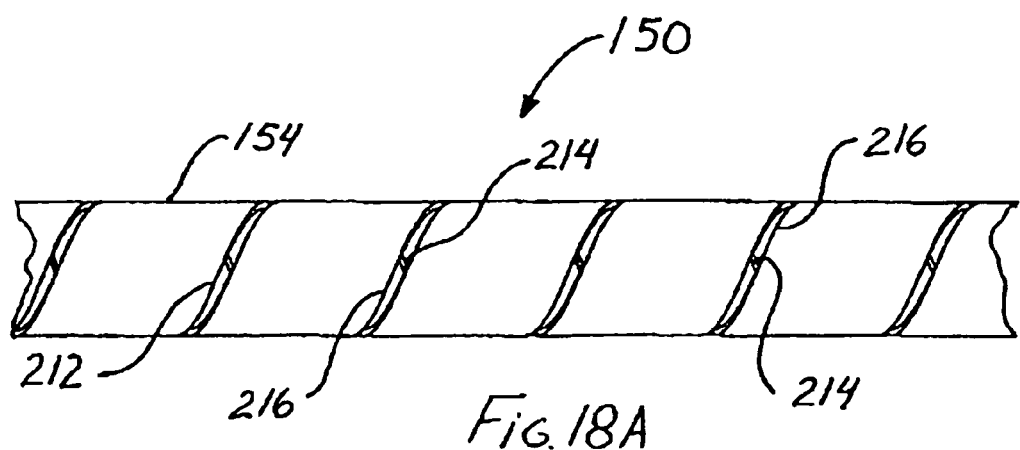
FIG. 18A is a perspective view of a catheter construction according to the present invention.
Figure 18B:
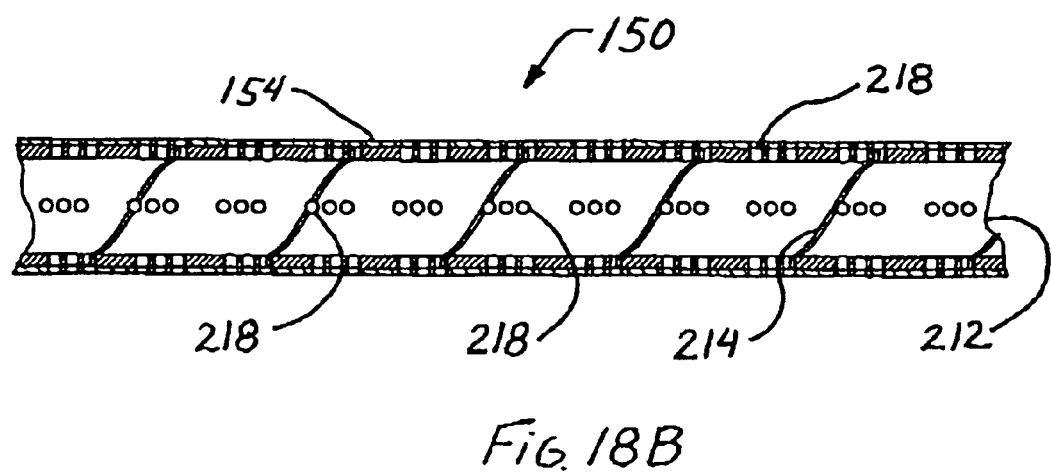
FIG. 18B is a perspective view of a catheter construction according to the present invention.

FIG. 17 is a partial cross-sectional view of a general catheter 150 of the present invention having a spiral cut tube (such as a polymer tube, metal tube such as a hypotube, etc.) 212 wrapped with a film layer 154. The gaps or cuts 214 in the tube are essentially sealed by the film wrap 154. The desired flexibility of the tube is maintained and by the addition of the film wrap 154, a sealed fluid lumen is formed within the tube. Such constructions are suitable for forming ports or "hydro-jets" into the tube. Shown in partial isometric view, FIG. 18A is a tube 212 having a spiral cut 214. The tube is covered with a film layer 154 that has gaps 216 between the adjacent film edges. The gaps 216 in the film layer in effect form fluid ports or hydro-jets that coincide with selected gaps in the cut tube. In an alternate embodiment shown in partial cross-sectional view FIG. 18B the tube 212 is fully covered by a film wrapped layer 154 similar to that shown in FIG. 17. The film layer can have cut holes or ports 218 that align with selected gaps 214 of the tube, or holes 218 can be cut through the tube to form a port or hydro-jet. Moreover, the tube can be provided with a spiral cut with changing pitch across all, or a part of, the length of the tube, thus providing a flexibility transition region in the tube. Of course, desirable flexible tubing can be obtained by other means than providing a spiral cut tube. In this regard any tubular element having at least one fenestration through its wall may be used. Suitable fenestrations can be obtained by, for example, etching, cutting, drilling, etc. Any desirable number of fenestrations can be provided. For example, strategically placed cuts could be located at any number of locations along the length and/or around the circumference of the tube. The cuts in the tubing could be strategically arranged to provide for varying flexibility across the length of any number of tubular bodies. Just as discussed above, the cuts in the tube would be suitable for forming ports for "hydro-jets". Furthermore, rather than using a cut tube, a spiral metal ribbon could be wrapped with a film layer 154.

With regard to film wrapping of fenestrated tubing, it is believed that an ePTFE/adhesive laminate film may be particularly useful. For example, as discussed above, it may desirable to provide an adhesive to the outer surface, the inner surface, or both, of the ePTFE film to provide for enhanced properties. In such a case, it is believed that the ePTFE is particularly attractive, since the ePTFE may act as a stable scaffold (i.e., the film tends to shrink only a small amount) for the adhesive. For example, when wrapping a metal hypotube with an ePTFE/FEP system, the FEP could act as an adhesive, the system could be heated to cause the FEP to flow; however, the FEP will tend to stay in the ePTFE structure and not infiltrate into the fenestrations in the hypotube. Further embodiments could include wrapping a cut PEBAX tube with an ePTFE film and an adhesive with a lower melting temperature—or indeed a UV curable adhesive. Other variations of this embodiment will now be apparent to the skilled artisan.

Figure 19A:
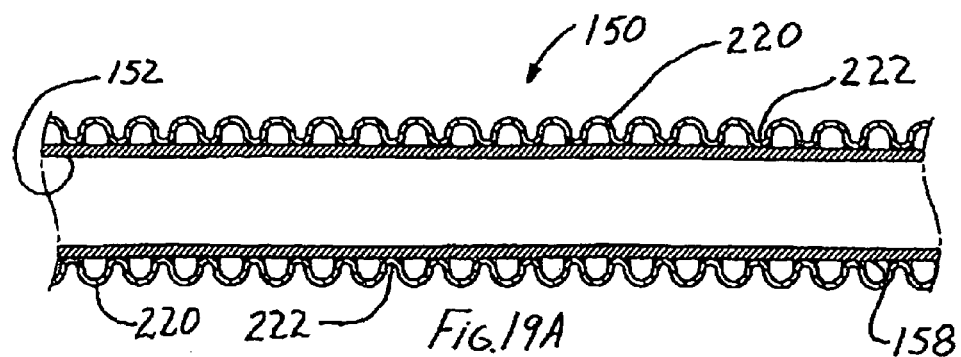
FIG. 19A is a cross-section of a catheter according to the present invention.
Figure 19B:
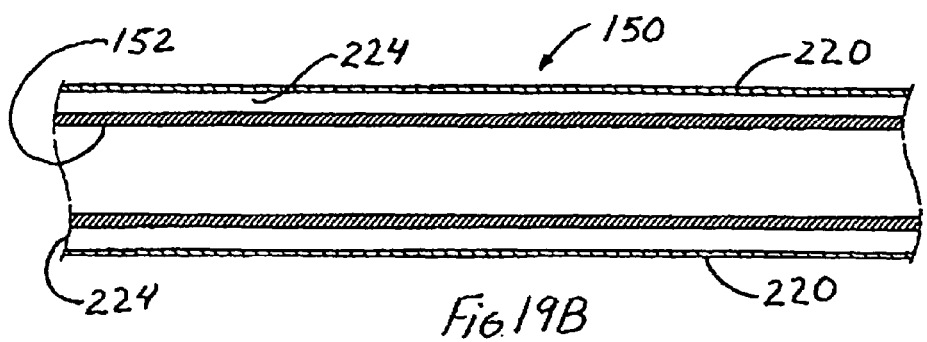
FIG. 19B is a cross-section of a catheter according to the present invention.

Film coverings of the present invention do not necessarily have to be adhered or fixed onto a base tubular element. In some preferred embodiments, catheters of the present invention can have film coverings that are non-adhered or separate from the underlying base tubular element. Shown for example in partial cross-sectional view FIG. 19A is a general catheter 150 of the present invention having a longitudinally extending tubular element 152 (which can have at least one lumen extending for at least a portion of its length, or can be a solid structure, such as a guidewire) covered with a "relaxed" non-distending film 220. The non-distending film covering 220 is shown having generally sinusoidal folds 222. The non-distendable film covering 220 can have any suitable relaxed or non-expanded shape having for example folds, corrugations or pleats which can be oriented circumferentially or longitudinally. The non-distending film covering 220 is shown in contact with portions of external surface 158 of the tubular element 152. The film covering 220 is not adhered to the depicted portion of the longitudinally extending tubular element 152. As shown in partial cross-sectional view FIG. 19B, when an inflation fluid or gas is injected into the interstitial space 224, the non-distending film covering 220 unfolds and expands to form a fluid communication path between the film covering 220 and the longitudinally extending tubular element 152. Inflation fluid or gas can be injected into the interstitial space 224, for example, via a port located on or near the proximal end of the catheter, or when tubular element 152 has a lumen, the tubular element 152 can be provided with perforations, apertures, etc., through the tube wall and the fluid or gas can be injected into the lumen through the perforations, apertures, etc., to unfold and expand the film covering.

Figure 20A:
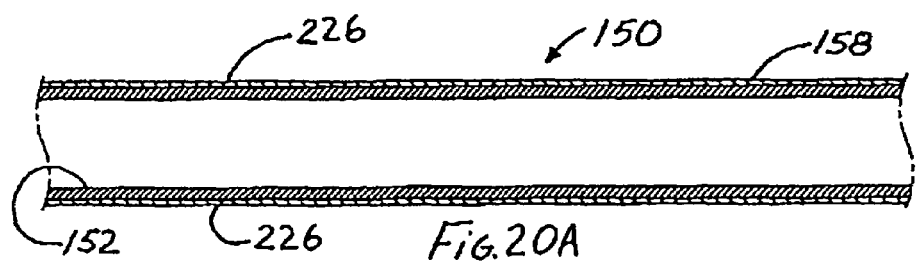
FIG. 20A is a cross-section of a catheter according to the present invention.
Figure 20B:
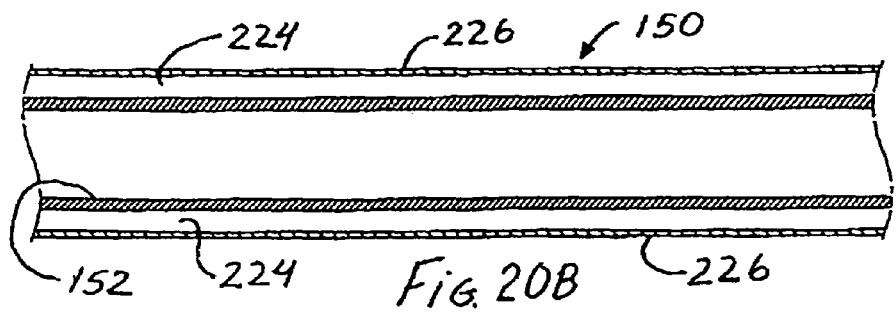
FIG. 20B is a cross-section of a catheter according to the present invention.

In a similar configuration, stretchable, elastic or distending film coverings can be applied and selectively non-adhered to a longitudinally extending tubular element. Shown for example in partial cross-sectional view FIG. 20A is a general catheter 150 of the present invention having a longitudinally extending tubular element 152 (which can have at least one lumen extending for at least a portion of its length, or can be a solid structure, such as a guidewire) covered with an elastic, stretchable film 226. The stretchable film covering 226 is shown in contact with (but non-adhered-to) an external surface 158 of the tubular element 152. As shown in partial cross-sectional view in FIG. 20B, when an inflation fluid or gas is injected into the interstitial space 224 (as discussed above), the film covering 226 stretches and expands to form a fluid communication path between the film covering 226 and the longitudinally extending tubular element 152. A film can be rendered "stretchable", for example, by applying an elastic material to the film while in a compressed state or by applying a film wrap having an expandable pattern similar to a "Chinese Finger Grip" configuration.

Figure 21:
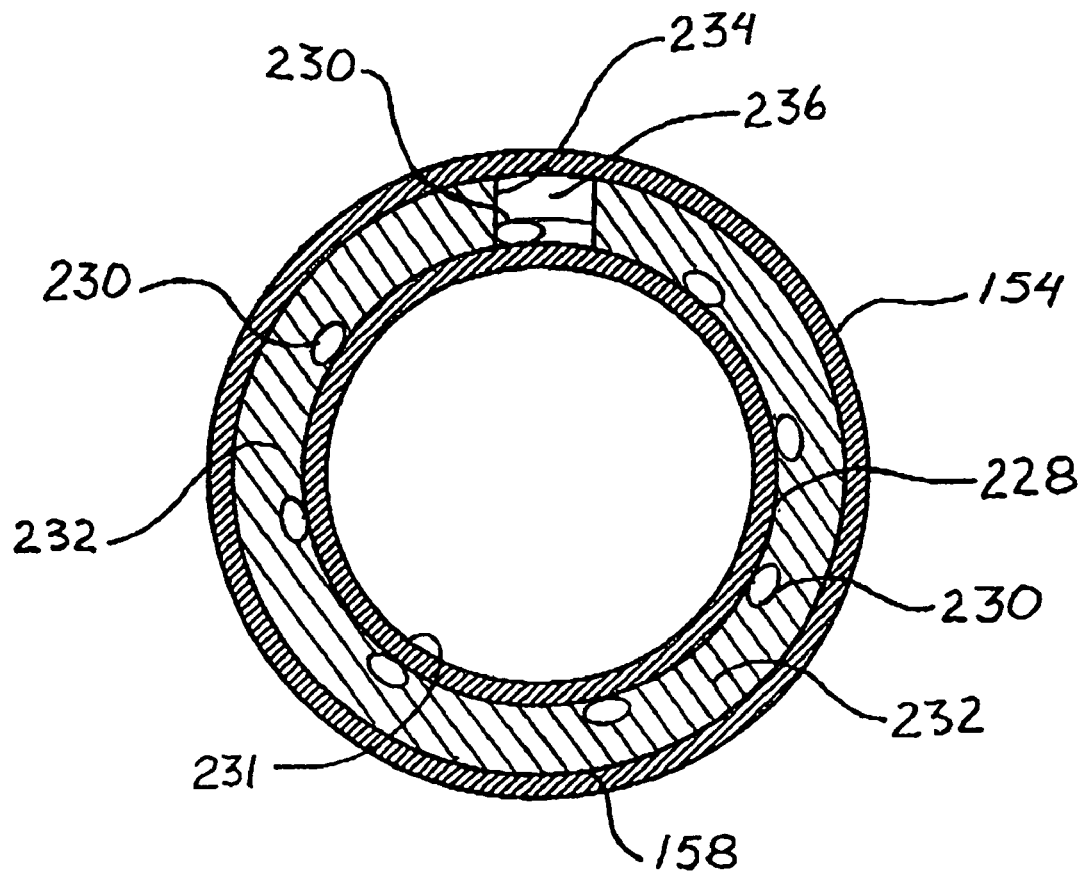
FIG. 21 is a cross-section of a catheter according to the present invention.

Alternate uses of film wrappings on catheters include the sealing of secondary lumens or channels. Shown for example in cross-sectional view FIG. 21 is a typical catheter section modified according to an aspect of the present invention. Shown is optional inner lubricious (e.g., PTFE) liner 228 defining a generally centrally located lumen 231, which can extend for at least a portion of the length of the catheter body or for the entire length of the catheter body. The PTFE liner 228 can be formed, for example, as an extruded tube of PTFE, or from PTFE tape (e.g., ePTFE tape) which has been formed into tubular shape by wrapping the tape about a mandrel, as discussed above. Also shown is an optional circumferentially and longitudinally extending wire support braid 230 embedded into a thermoplastic layer 232. In an aspect of the invention thermoplastic layer 232 is provided without the wire support braid. A laser (such as a 20 watt $CO^2$ laser, Applied Laser Technology, Beaverton, Oreg.) can be used to selectively cut a longitudinal (or spirally) extending channel 234 of virtually any desired shape in the thermoplastic layer 232. The channel can extend for at least a portion of the length of the catheter body or for the entire length of the catheter body. The laser power can be adjusted to remove the thermoplastic 232 but not the PTFE inner liner 228 or the optional wire support braid 230. Film 154 can then be applied to the exterior surface 158 of the catheter, forming a fluid communication path 236 or lumen in the existing wall of the catheter. The film 154 can be provided to cover the channel and only portions of the thermoplastic layer near the channel so as to form a fluid communication path 236 in the catheter, or the film 154 can be wrapped about the circumference of the catheter, thus forming a fluid communication path 236 in the catheter.

Figure 21A:
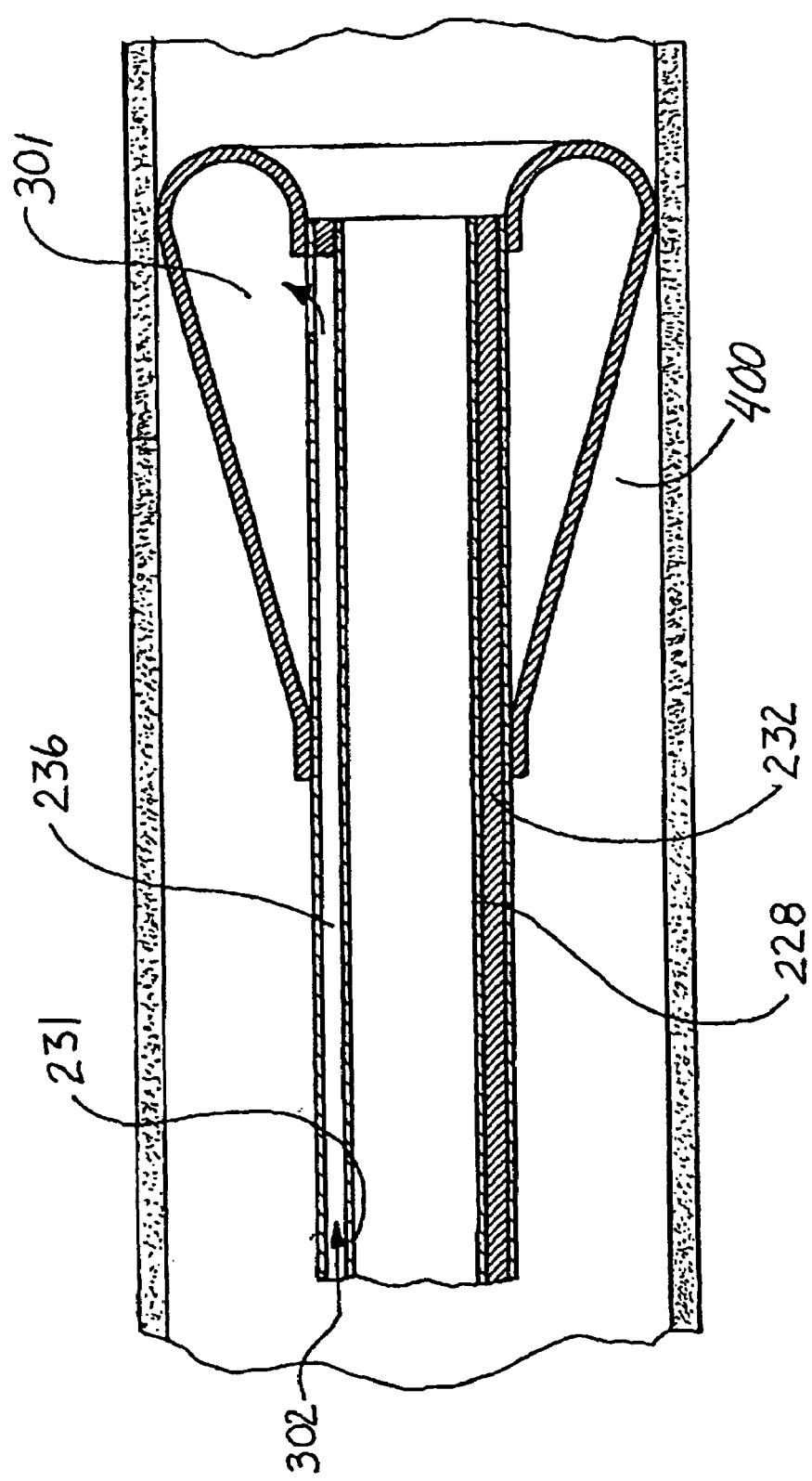
FIG. 21A is a cross-section of a catheter according to the present invention.

In a further aspect of the invention, demonstrated in FIG. 21A, the catheter can have a proximal end and a distal end, with a generally centrally located lumen 231 extending from its proximal end to its distal end. The longitudinally (or spirally) extending channel 236 extends from the catheter proximal end (or near its proximal end) to its distal end (or near its distal end) where it can be in fluid communication with the interior of an inflatable member 301 located on the distal end of the catheter. Inflation fluid can be delivered to, and removed from, the interior of inflatable member 301 through channel 231 as shown by arrows 302. Inflatable member 301 can be, for example, an occlusion balloon designed to occlude blood flow in a target vessel or artery 400, while still allowing blood to flow through the generally centrally located lumen 231 of the catheter. Generally centrally located lumen 231 can also be used to advance a guidewire (or other desirable device such as a dilatation catheter, thrombectomy removal device, treatment catheter, embolic filter, medication, etc.) through the catheter to aid in guiding the catheter to a treatment site. Use of the wire support braid 230 may allow for construction of a catheter of this type with extremely small profiles, due to the extra support provided by the wire braid in combination with the ability to form, for example, a fluid delivery lumen (i.e. the channel) of extremely small cross section. Thus, the catheter of this aspect of the invention may be particularly attractive for use in treatments in the cerebral vasculature of a patient. Furthermore, the catheter according to this aspect of the invention could be constructed so that a dilatation balloon is located on the distal end of the catheter. Fluid communication path can be in fluid communication with the interior of the dilatation balloon, thus allowing for the delivery and removal of inflation fluid to the dilatation balloon. Generally centrally located lumen 231 could be sized to accept in a sliding relationship a guidewire. Of course, an expandable stent could be mounted on the dilatation balloon.

Figure 22A:
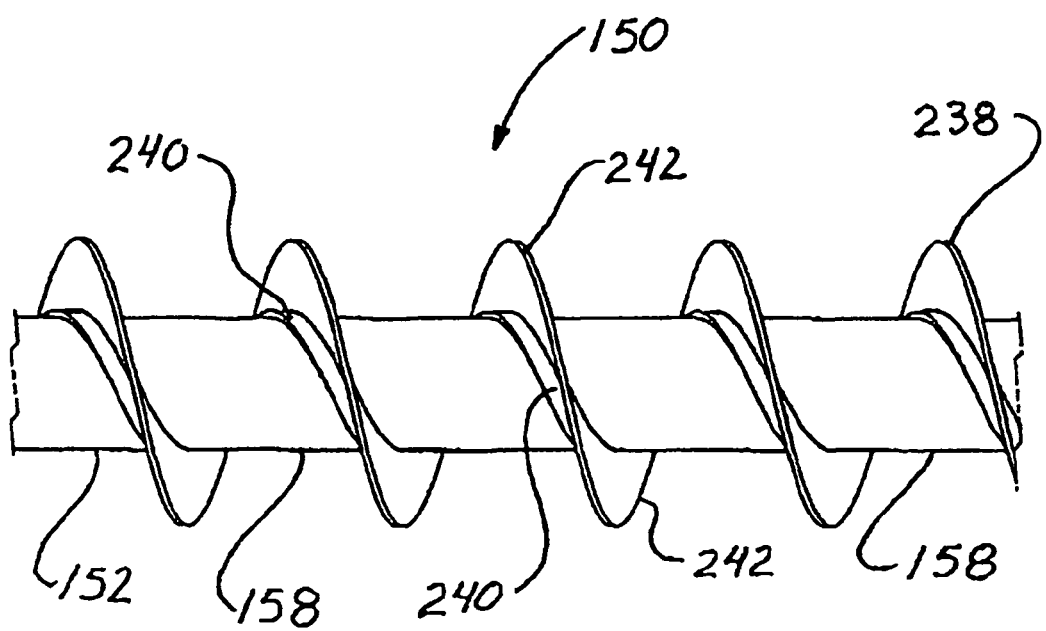
FIG. 22A is a perspective view of a catheter according to the present invention.

Film wrapping processes can also be used to alter or create new surface profiles on tubular elements. Shown for example in partial isometric view, FIG. 22A is a catheter section 150 comprising a longitudinally extending tubular element (which may contain a lumen extending for at least a portion of its length) 152 having a selectively adhered film covering 238 that is in contact with the exterior surface 158 of the tubular element 152. The film 238 has portions that are adhered 240 to the tubular element 152 and portions that are not adhered 242, forming a continuous spiral array of "fish scales". Such fish scales can be used to impart directional friction (e.g., within a blood vessel or artery) so that a catheter of the present invention resists longitudinal motion in one direction yet slides easily in the opposite direction. Fish scales or "sails" can also be used to "catch" a fluid flow (e.g., blood flow) and allow a catheter to be carried along with the fluid flow, or at least aid in advancing the catheter. Films can be selectively coated with an adhesive or thermoplastic, for example, on one edge to form scales or other surface modifications according to the present invention. Films fully coated with an adhesive or thermoplastic can be wrapped over a temporary intermediate layer of a high temperature material that prevents portions of the film from adhering to itself.

FIGS. 22B and 22C show in partial isometric and in partial cross-section respectively a catheter section 150 according to this aspect of the invention. As shown in FIGS. 22B and 22C, the film 238 is shown laying against the exterior surface 158 of the tubular element 152. Ghost lines 241 in FIG. 22B indicate the portions of the film that are adhered to the exterior Surface 158 of the tubular element 152. Moreover, FIG. 22D demonstrates use of a catheter according to this aspect of the invention as, for example, a dilatation balloon catheter. As seen in FIG. 22D, catheter 150 is shown being advanced to place expandable member 301 across a stenosis S. The arrows indicate the direction of blood flow within a patient's blood vessel or artery. As shown, selectively adhered film covering 238 is now in contact with the exterior surface 158 of the tubular element 152 at only those portions where the film 238 has been adhered 240 to the tubular element 152, thus forming a continuous spiral array of "fish scales". As should now be apparent, the continuous spiral array of fish scales, which also resemble an auger formation, can assist, and perhaps indeed direct, the catheter 150 to advance distally in a chosen blood vessel or artery. Moreover, it should be apparent that by providing a rotational force to the catheter 150, further ease of advancement is obtainable. Furthermore, by applying rotational force, it may be possible to help increase the blood flow in patient's artery or vessel. It should be noted that the film forming the spiral array of fish scales need not be provided as a continuous strip of film. As should now be appreciated, the selectively adhered film covering may also have benefits when the catheter is fixed, relative to the direction of blood flow. As shown in FIG. 22D, if blood flow is in the direction of the arrows, the film may act to disrupt or obstruct blood flow in a vessel. If blood flow is in a direction opposite the arrows, the blood flow may push the film against the outer surface 158 of the catheter 150; thus the film will not significantly interfere with blood flow in this direction.

In an alternative embodiment, suitable "fish scales" or "sails" could be obtained by using polymer film having a variable stiffness or thickness across the width of the film. For example, a suitable polymer film could be cut into tape form wherein one side of the tape is thicker than the other side of the tape. As shown in FIG. 22E, the polymer film tape 238 could then be located on the exterior surface 158 of a tubular element 152, with the thicker side of the tape 238a closer to the proximal end of the tubular element 152. Like the other embodiments, the tape could be arranged in a continuous manner about the tubular element, or in any desired discontinuous manner. The thicker sides of the tape could serve the same function as the "fish scales" and "sails" discussed above. The surface of polymer film tape 238 in contact with the exterior surface 158 of the tubular element 152 can be, if desired, either completely adhered to the exterior surface or adhered in only selected portions of the film area in contact with the exterior surface 158.

Still further aspects of the invention include wire-based guidewires, catheters and micro-catheters having profiles suitable for advancement into a patient's cerebral vasculature. Such wire-based devices can comprise at least one longitudinally extending wire having a length and at least an outer surface with at least one cut therein, a proximal end, and a distal end. The wire-based device further comprises polymer film covering at least a portion of the outer surface of the at least one wire, and a therapeutic and/or diagnostic device, located at the distal end of the wire-based device.

In an aspect of the invention, the polymer film is provided as a polymer film wrap. In a further aspect of the invention, the polymer film can be provided as a tubular shrink wrap. With regard to the polymer film wrap, in an aspect of the invention, the polymer film wrap is provided as a helical wrap, as discussed above. Moreover, in an aspect of the invention, the polymer film wrap comprises ePTFE, as discussed above. In a further aspect of the invention, the therapeutic device can be selected from the group consisting of expandable balloons (e.g., either dilatation balloons or occlusion balloons), stents, stent-grafts, energy-emitting devices, and fiber-optic devices. In an aspect of the invention, the stents and or stent-grafts can be self-expanding. Moreover, in a further aspect of the invention, the stent or stent-graft can be mounted over an expandable balloon.

The at least one longitudinally extending wire can comprise, for example, metal wire, polymer or metal tubing (such as stainless steel hypo tube), etc. The wire can further include an inner surface defining at least one lumen extending for at least a portion of the wire length. The at least one lumen can extend from the proximal end to a point proximal to the distal end or to the distal end of the wire. Furthermore, it may be desirable to provide at least a portion of the inner surface of the wire with a polymer covering (e.g., a polymer film covering).

In an aspect of the invention, an expandable balloon is located near the distal end of the wire and the wire lumen extends from the proximal end to near the distal end of the wire and is in fluid communication with the interior of the expandable balloon.

When the wire comprises a hypo tube, it may be desirable for the at least one cut to extend from the outer surface to the inner surface of the hypo tube (i.e., completely through the wall of the tube). Moreover, the at least one cut may be a spirally extending cut extending for any desirable length of the hypo tube. In an aspect of the invention, the spirally extending cut can extend from the proximal end to the distal end of the hypo tube. Moreover, the pitch of the spiral cut can be varied from one point to another along the length of the tube to vary the flexibility of the tube over a desired length.

Moreover, in an aspect of the invention, the at least one cut, for example the spirally extending cut forms a spirally extending channel in the wire surface. The spirally extending channel can extend for any desired length of the wire and can be of varied pitch (or a constant pitch) from one point to another. In an aspect of the invention, the spirally extending channel can extend from the proximal end of the wire to near (or completely to) the distal end of the wire. The channel can then be covered with polymer film, thus forming a spirally extending lumen in the wire. The wire of this aspect of the invention can be a solid wire, or it can comprise a generally centrally extending lumen defined by an inner surface of the wire (e.g., the wire can be a hypotube). When the wire comprises a centrally extending lumen defined by an inner surface of the wire, the spirally extending cut does not extend through the inner surface of the wire. The spirally extending lumen can be in communication with the interior of an expandable balloon located near the distal end of the wire. Thus inflation fluid can be delivered to the balloon interior via the lumen.

It is also possible to provide at least one radiopaque material to the device. The radiopaque material can be any suitable material and can be located at any desired point along the length of the device.

When a self-expanding stent or stent-graft is provided, the stent or stent-graft may be held in a compressed state by a sheath (or other suitable constraining device) located over the stent or stent-graft. In such an embodiment, the device may further comprise a deployment line extending from a port at the proximal end of the device through the lumen, exiting the lumen at a point proximal to the sheath through a port formed through the wire, and connected to the sheath. The self-expanding stent or stent-graft may then be deployed by the physician once located at the desired treatment site. Moreover, in such an embodiment it may be desirable to further provide an expandable balloon at or near the distal end of the wire, the balloon having an interior, wherein the interior is in fluid communication with the lumen.

The device may further comprise a stiffening device, which may be located in the at least one lumen. In an aspect of the invention, the stiffening device is capable of being moved proximally and distally in the at least one lumen. Suitable stiffening devices include, for example, stylets, wires, tubes, braids, and combinations thereof. The stiffening device may be solid or hollow. Moreover, the stiffening device can have a variable stiffness along at least a portion of its length. Further, the stiffening device may comprise any suitable material, such as, metal, metalloids, and polymers.

It should be noted that the inner surface or the outer surface of the wire can be pretreated (i.e., chemically etched, etc.) prior to providing the polymer film or covering to the surface.

It should be understood that due to the combination of the polymer film and wire it is possible to construct wire based devices having extremely small profiles, the device being sufficiently flexible, yet including the necessary pushability and maneuverability to be advanced deep into a patient's cerebral vasculature. Moreover, the wire catheter can also serve as a guidewire wherein a further device can be advanced over the wire catheter to provide at least one additional therapeutic device to a treatment site.

Several exemplary embodiments (and uses therefore) of the above-described wire-based device will now be discussed. Each of the below embodiments can comprise any of the features of the above-described wire-based device.

Figure 23:
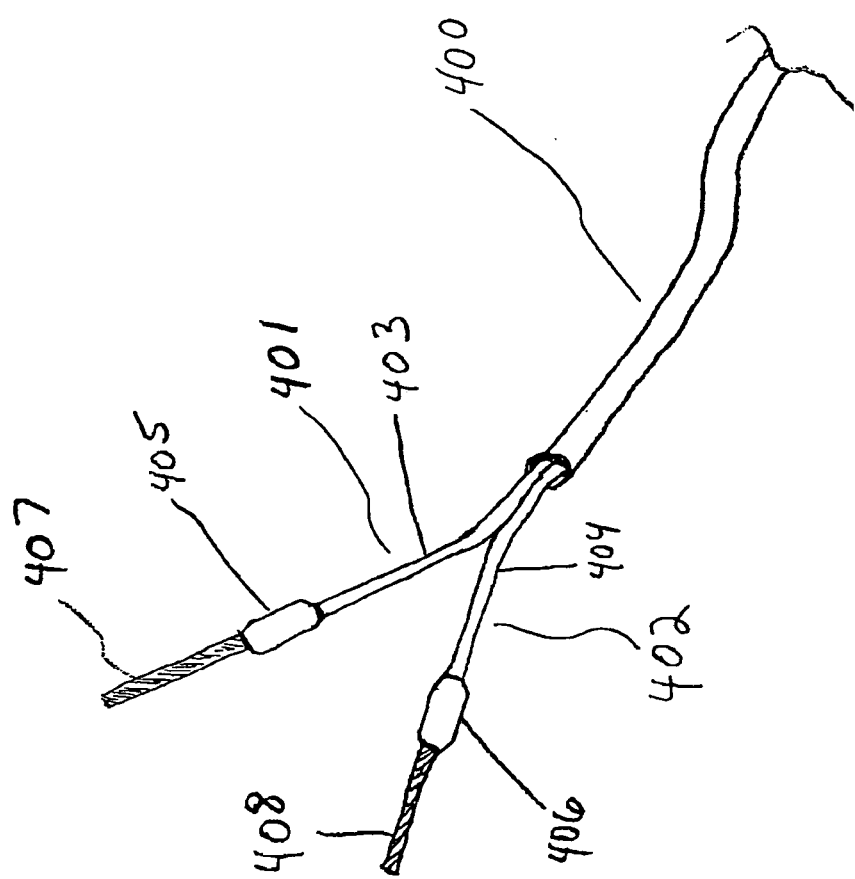
FIG. 23 is a perspective view of a catheter construction according to the present invention utilizing two small profile wire based devices.

Turning to FIG. 23, one exemplary embodiment utilizing two wire-based devices discussed above and according to the invention is shown. Shown is elongated tube 400 having a generally centrally located lumen wherein two wire-based devices 401 and 402 are slideably located. Each wire-based device comprises a balloon-on-a-wire device having an elongated wire having a length, an outer surface having at least one cut therein, polymer film 403 and 404 covering at least a portion of the outer surface, a proximal end and a distal end, and a first expandable balloon 405 and 406 near each wire distal end. Expandable balloons 405 and 406 can be either dilatation balloons or occlusion balloons. Moreover, expandable stents may be mounted over the balloons as desired. Each wire-based device further comprises atraumatic tip 407 and 408, such as a coil. Each wire-based device further includes an inflation lumen extending for at least a portion of the length of the elongated wire and in communication with the interior of the expandable balloon located at the wire distal end. The wire-based devices are in a sliding relationship with each other and with the centrally located lumen of the elongated tube 400.

The embodiment shown in FIG. 23 is particularly useful for treating bifurcations where the elongated tube 400 can be advanced to a point proximal to the target bifurcation and then each wire-based device 402 and 403 advanced into the desired treatment vessel distal to the bifurcation. For example, the distal end of the elongated tube 400 can be advanced into a patient's common carotid artery, just proximal to the bifurcation leading to the internal carotid artery and the external carotid artery. Wire-based device 402 can then be advanced into the internal carotid artery and wire-based device 403 can then be advanced into the external carotid artery. Artery occlusion, dilatation, and/or stent placement can then be carried out. Moreover, the elongated tube can be sized to be advanced distally into the patient's internal carotid artery to treat locations distal thereto. Thus, this embodiment allows the practitioner to keep both wire-based device (or one wire-based device) in the elongated tube 400 until the target region is reached, thus eliminating the possibility of the wires getting crossed (a problem if the wire-based devices are advanced separately, or without an elongated tube).

Elongated tube 400 can further comprise an expandable member, such as an expandable balloon, located at the distal end of the elongated tube 400. An inflation lumen extending for a portion of or the entire length of the tube and in communication with the balloon interior can also be provided.

Elongated tube 400 can include an at least partial coating of a lubricious material on at least one of the tube outer surface or lumen surface. Such a coating can extend for a portion of or the entire length of the tube. The elongated tube 400 can comprise any suitable material, such as metals and plastics. In an aspect of the invention the tube 400 is a plastic extrusion. In a further aspect of the invention, the elongated tube can comprise polymer wrapped film. The elongated tube 400 preferably has a length that is less than the length of at least one of the balloon-on-a-wire devices, more preferably a length less than both of the balloon-on-a-wire devices. In a further aspect of the invention the elongated tube 400 comprises an adjustable length. The tube length can be made adjustable by providing at least a portion of the tube with a scrunchable section, as defined above.

The elongated tube 400 preferably has an outer diameter of about 1.25 mm.

Moreover, the embodiment shown in FIG. 23 can further comprise a catheter having a lumen extending for at least a portion of the length of the catheter, and preferably, for the entire length of the catheter. The elongated tube 400 can be locatable within the catheter lumen, in a sliding relationship. The catheter can have an inflatable member at its distal end.

Figure 24:
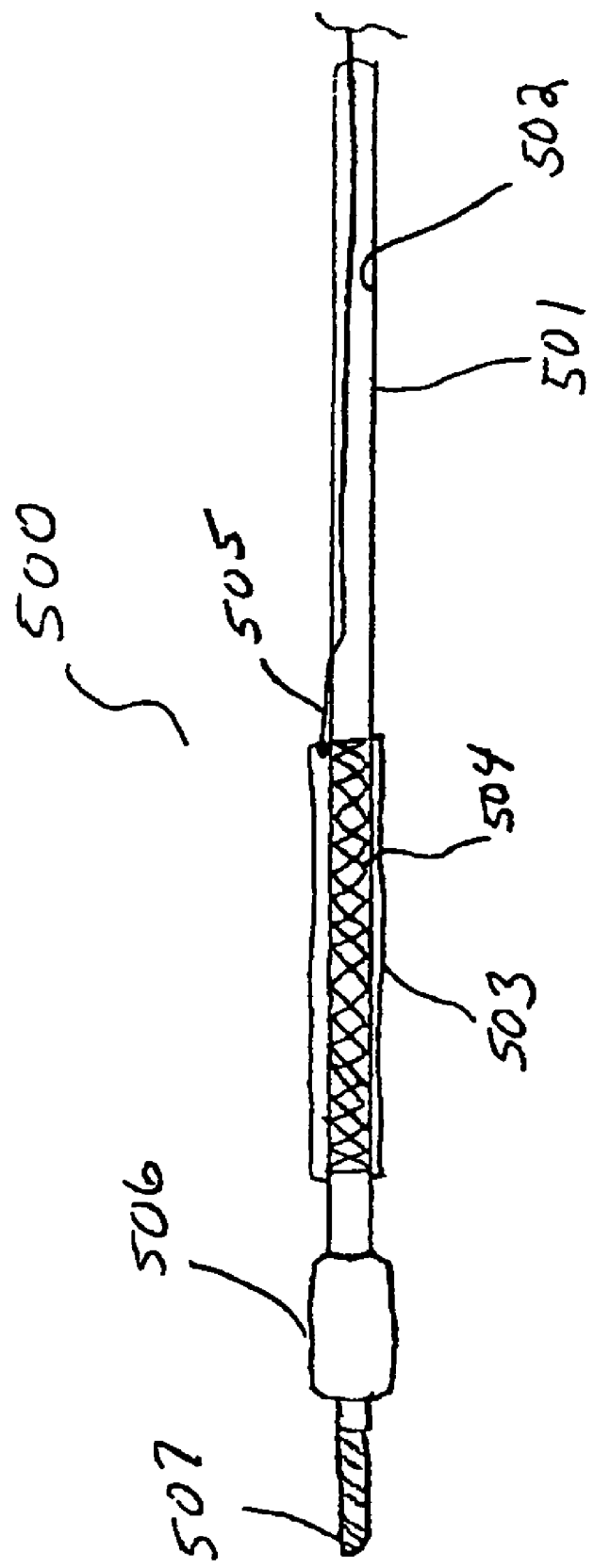
FIG. 24 is a partial cross-section of a wire-based device according to the present invention.

Turning now to FIG. 24 there is shown in schematic cross-section a further aspect of the wire-based device according to the invention. Shown is a balloon-on-a-wire device further including a self-expanding stent located near the distal end thereof. As shown, the device 500 includes wire catheter 501 having a generally centrally located lumen 502 extending from the wire proximal end (or near its proximal end) to near the wire distal end and in communication with the interior of expandable balloon 506. The device also includes atraumatic tip 507 attached to the distal end of the wire catheter 501. Located proximal to expandable balloon 506 is self-expanding stent 504 (although shown located proximal to the expandable balloon 506, the stent 504 could also be located distal to the expandable balloon, or two stents could be provided, one distal to and one proximal to the expandable balloon). Self-expanding stent is held in a compressed state by stent containment member 503. Stent containment member 503 can cover a portion of, or the entire length of, the stent 504. In an aspect of the invention stent containment member 503 comprises a longitudinally extending sheath. Attached to the proximal end of the stent containment member 503 is deployment mechanism 505 (such as a deployment line). Deployment mechanism 505 extends proximally to the proximal end of the device where it can be withdrawn proximally, either by hand or use of a suitable mechanical device. Deployment mechanism 505 can extend along the outer surface of the wire catheter and then, at any desired point along the length of the wire, extend through an opening in the wall of the wire, into the generally central lumen of the wire. The polymer film covering (discussed above) can cover the opening and provide a tight seal between the polymer film and the deployment mechanism 505. In such an embodiment the generally centrally located lumen 502 can then serve a dual function. That is, the lumen 502 can serve as an inflation lumen, being in communication with the interior of the expandable balloon 506, and also serve as a lumen for the deployment line. With judicious selection of polymer film covering and wire catheter material (such as ePTFE and metal hypo-tube, respectively) the film can provide a seal between the catheter wall and the deployment line to prevent balloon inflation fluid from escaping the lumen, but still allowing the deployment line to be retracted proximally along the device.

In a further aspect of the invention the device can comprise at least a second lumen, wherein the first lumen accepts the deployment member 505 in sliding relationship and the second lumen is in communication with the interior space of the expandable balloon 506.

Operation of the device should now be apparent. The device can be advanced to the desired treatment site and expandable balloon 506 (which can be either an occlusion or dilatation balloon) inflated. Deployment mechanism 505 can then be retracted to withdraw stent containment member 503 to allow self-expanding stent 504 to expand. Thereafter, expandable balloon 506 can be deflated and the device withdrawn.

Figure 25:
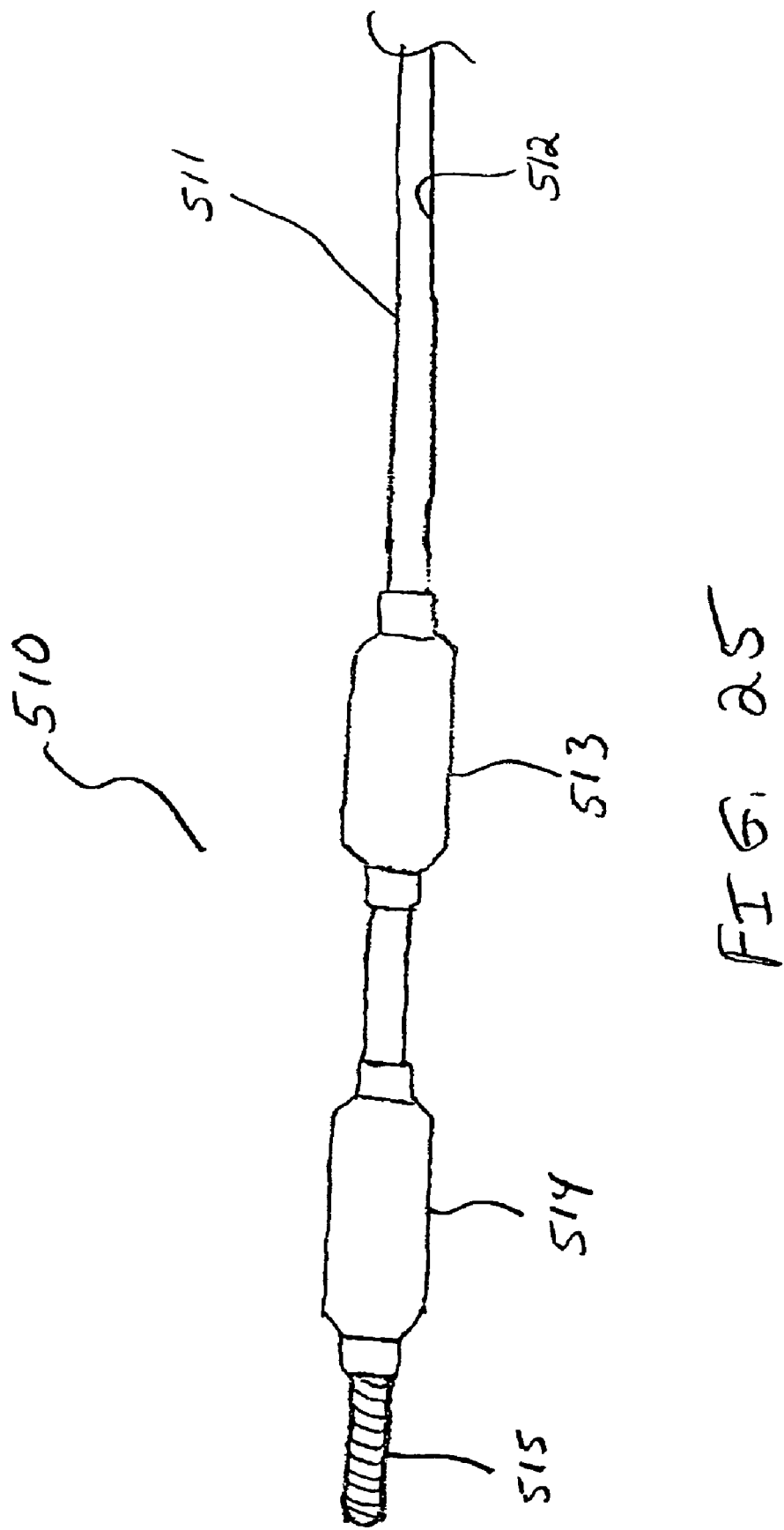
FIG. 25 is a side view of a wire-based device according to the present invention.

Turning now to FIG. 25, still a further embodiment of the balloon-on-a-wire device of the invention is shown. Shown is a balloon-on-a-wire device comprising two balloons located near the distal end of the device in spaced apart relation. The balloon-on-a-wire device 510 comprises wire catheter 511 having at least one cut in its outer surface and a polymer film covering (as discussed above). The wire catheter 511 also includes at least one generally centrally located lumen 511 that extends from a port at the proximal end (or near the proximal end) of the wire catheter 511 to the interior space of first balloon 513, and, optionally, the interior space of second balloon 514. Finally, the device includes atraumatic tip 515. The device can include at least a second lumen that can extend from a port at the proximal end (or near the proximal end) of the wire catheter 511 to the interior space of the second balloon. Although the first and second balloons may be either dilatation balloons or occlusion balloons, in an aspect of the invention the balloons are occlusion balloons. Such a device may be particularly suitable for thrombus removal from a patient's cerebral vasculature.

For example, the device can be sized to be capable of being advanced deep into a patient's cerebral vasculature, with or without the use of a microcatheter or guide sheath to aid the device in being advanced. The most distal balloon can be advanced just distal to the thrombus and the proximal balloon located proximal to the thrombus. The balloons can be inflated (one at a time, or simultaneously) and the thrombus removed by retracting the balloon-on-a-wire device.

Figure 26:
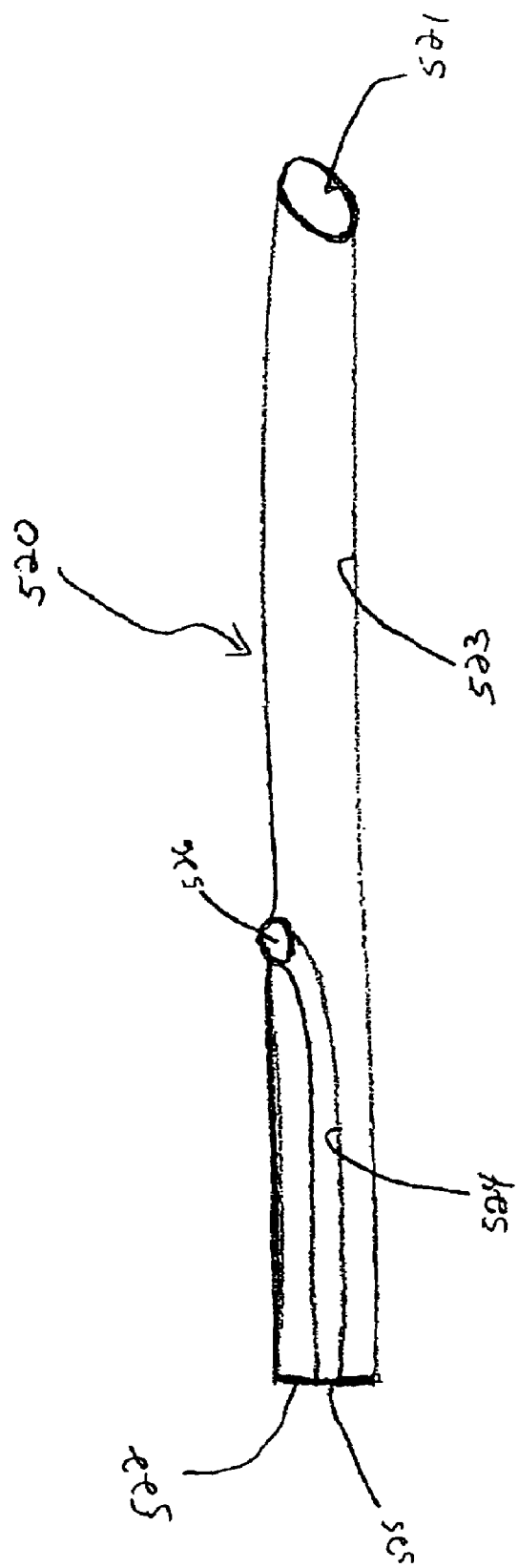
FIG. 26 is a side view of a microcatheter according to the present invention.
Figure 27:
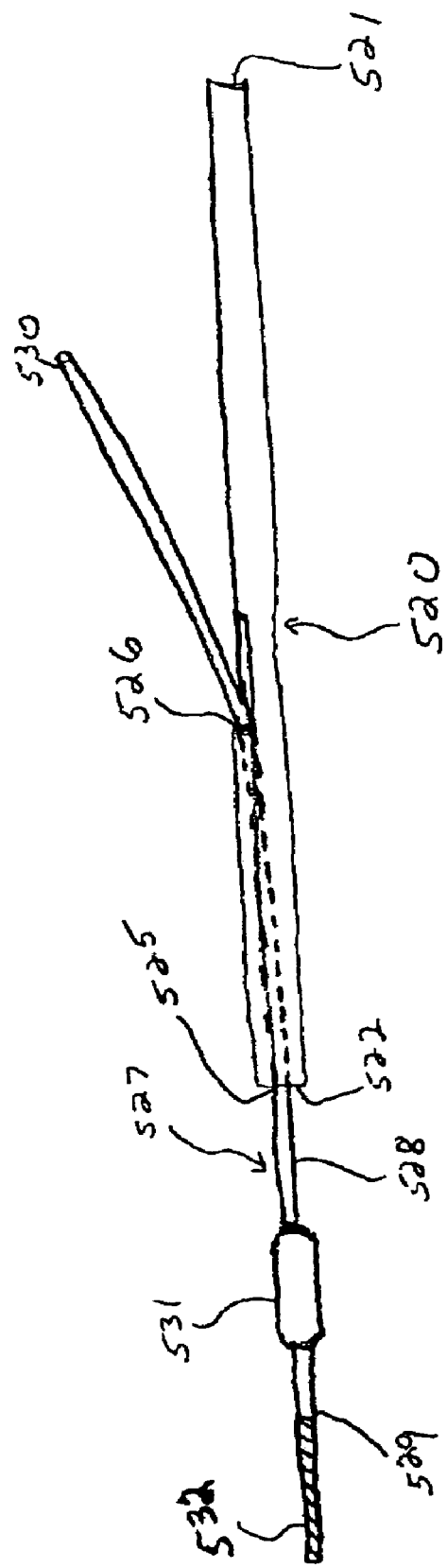
FIG. 27 is a side view of a microcatheter and a wire-based device according to the present invention.

Turning now to FIGS. 26 and 27 there is shown a combination of a wire-based device and a microcatheter. The microcatheter 520 is a rapid exchange type microcatheter construction and comprises a shaft having a length, an outer surface, a proximal end 521, a distal end 522, and a first longitudinally extending catheter lumen 523 and a second longitudinally extending lumen 524. The first longitudinally extending catheter lumen 523 extends from the proximal end 521 to the distal end 522. The second longitudinally extending catheter lumen 524 extends from a first port 525 at the distal end to a second port 526 located proximal to the distal end and distal to the proximal end. A wire-based device 527 according to the invention is slidably locatable within the second longitudinally extending catheter lumen 524, as shown in FIG. 27. The wire-based device 527 comprises a length, an outer surface having at least one cut therein, and polymer film 528 covering at least a portion of the outer surface of the wire shaft. The device further comprises a distal end 529 and a proximal end 530, an inner surface defining a longitudinally extending wire lumen (not shown) extending from the proximal end 530 to a point distal thereto, and an expandable balloon 531 with an interior space located near the wire distal end 529. Further shown is atraumatic tip 532 which can be attached to the wire distal end 529.

In an aspect of the invention, the microcatheter has a length of from about 75 cm to about 150 cm. Moreover, the microcatheter preferably has a crossing profile of from about 3 french to about 6 french. The wire-based device is preferably sized to be capable of being advanced into a patient's cerebral vasculature. For example, a wire-based device of this embodiment can have a length of from about 90 cm to about 180 cm. Moreover, the wire-based device can have a crossing profile equal to standard guidewire devices. The device will be capable of being moved to and fro within the second longitudinally extending lumen 524 of the microcatheter 520. In an aspect of the invention the second port 526 can be located relatively closer to the distal end of the microcatheter and relatively further from the proximal end of the microcatheter. In a further aspect of the invention the second port 526 can be located from about 5 cm to about 30 cm from the distal end 522 of the microcatheter. In a further aspect of the invention the longitudinally extending wire lumen extends from the wire proximal end to a point near the distal end and is in fluid communication with the interior space of the expandable balloon 531.

Figure 28:
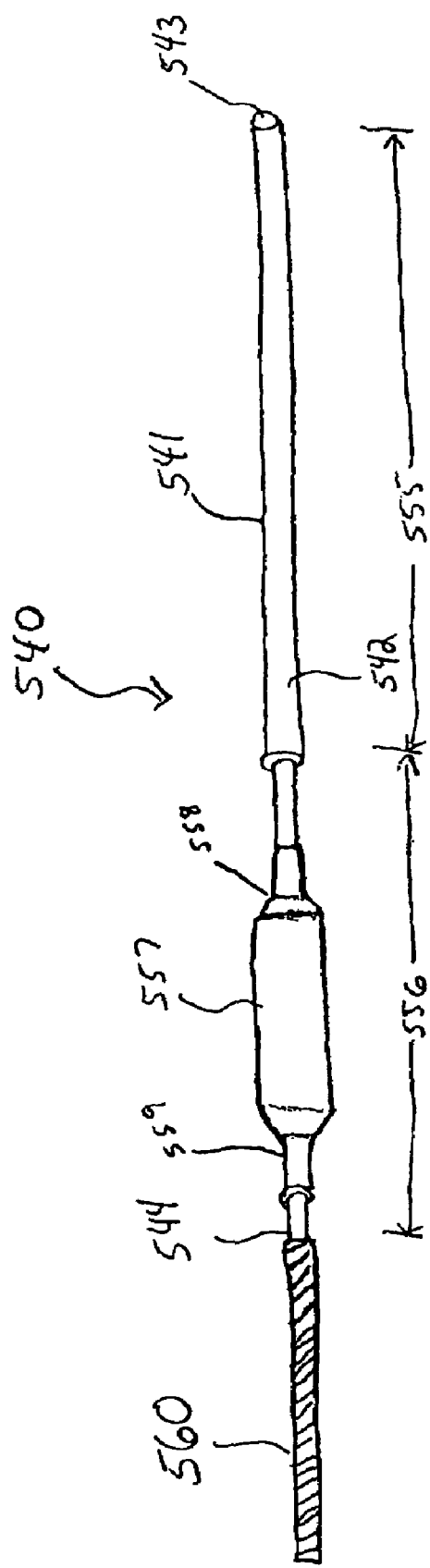
FIG. 28 is a side view of a wire-based device according to the present invention.

A still further embodiment of the wire-based device is shown in FIG. 28. As shown, the device is a balloon-on-a-wire device 540 comprising an elongated wire 541 having a length, an inner surface defining a longitudinally extending lumen (not shown), an outer surface having at least one cut therein, polymer film 542 covering at least a portion of the outer surface, a proximal end 543, a distal end 544, a proximal section 555 having a first outer diameter, and a distal section 556 having a second outer diameter that is less than the first outer diameter. The device further comprises expandable balloon 557 having an interior, a compressed state, an expanded state, a proximal end 558, and a distal end 559, the distal end 559 of the balloon 557 being sealed to the wire device distal section 556. The expandable balloon interior is in fluid communication with the longitudinally extending lumen. In an aspect of the invention the device further comprises atraumatic tip 560 attached to the wire distal end 544. In a further aspect of the invention the balloon proximal end 558 can be sealed to the wire proximal section 555. In a still further aspect of the invention the balloon proximal end 558 can be sealed to the wire distal section 556.

In an aspect of the invention the expandable balloon 557 in its compressed state has an outer diameter substantially equal to or less than the first outer diameter of the wire.

In an aspect of the invention, the device can have a length of from about 75 cm to about 150 cm. Advantages offered by the device include, but are not limited to, crossing profile is substantially the same over the length of the device and can be the same as that of a standard guidewire. Moreover, the device can serve as a guide wire, allowing for a second device to be advanced over it to treat a target region. For example, the device could be advanced to a first target region, the target, such as a stenosis, can be treated (e.g., dilated with a dilatation balloon on the balloon-on-a-wire device), then a catheter can be advanced over the device to treat a region distal to the first target region. Since the crossing profile of the balloon-on-a-wire device is substantially the same over the length of the device, the catheter can be easily passed over the balloon of the balloon-on-a-wire device.

Figure 29:
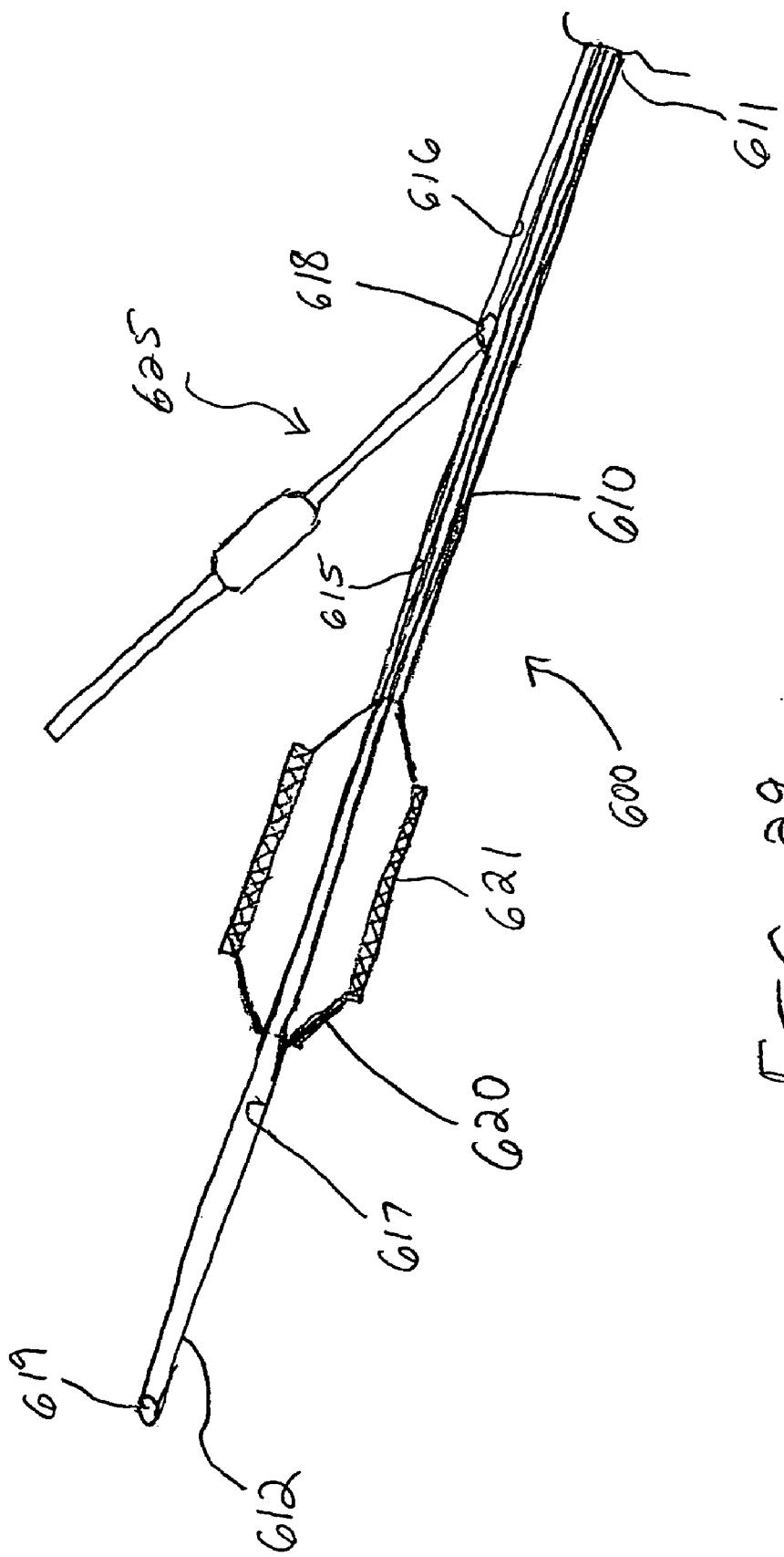
FIG. 29 is a partial cross-section of a wire-based device according to the present invention.

A still further embodiment of the wire-based device is shown in FIG. 29. As shown, the device is a catheter 600 comprising an elongated catheter body 610 having a length, a proximal end 611, and a distal end 612. The device further comprises at least a first lumen 615 and a second lumen 616 which extends distally from the proximal end 611 of the elongated catheter body 610. The second lumen 616 terminates at a port 618 located proximal of expandable balloon 620. The expandable balloon 620 has an interior space and is located near the distal end 612 of the catheter body 610. The interior space of the expandable balloon is in fluid communication with the first lumen 615. Preferably the balloon is a dilatation balloon. In some embodiments, a stent 621 is loaded onto the balloon. The first lumen 615 and/or second lumen 616 can be provided with a first component having a change in stiffness from a first point to a second point. In the first lumen 615 the first component can extend to a point distal to the port 618 of the second lumen 616. In the second lumen 616 the second component can extend essentially from the proximal end to the port 618. This first component may be a hollow tube, a wire, or braiding. Preferably the first component is a hollow tube comprising a metal. In a preferred embodiment, the first component comprises a hypotube.

As further shown in FIG. 29, this embodiment may further comprise a balloon on a wire device 625 slidably located within the second lumen 616 of the catheter body 610. In a preferred embodiment, either the catheter, the balloon on a wire device, or both the catheter and the balloon on wire device further comprise at least one radiopaque material.

The catheter may further comprise a third lumen 617 extending proximally from a port 619 at the distal end 612. In one embodiment, the third lumen 617 extends from the distal port 619 to a port (not shown) at the proximal end. Alternatively, the third lumen 617 may extend from the distal port 619 to a port (not shown) located proximal to the expandable balloon and distal to the proximal end 611 of the catheter.

A further aspect of the invention comprises a method for advancing catheters and/or balloon-on-a-wire devices distally into tortuous arteries. The method includes the use of a balloon-on-a-wire device according to the invention. The balloon-on-a-wire device is used in tandem with a catheter having an expandable balloon on the distal end thereof and a guide-wire receiving lumen extending from the proximal end (or near the proximal end) to a point distal to the expandable balloon, and preferably to the distal end of the catheter.

The method allows for the relatively easy advancement of the balloon-on-a-wire device and a balloon catheter into tortuous vasculature by alternating using each device as an anchor while advancing the other device distally into the vasculature.

The method includes the steps of providing a balloon catheter device having a length, a proximal end, a distal end, an outer surface, a first longitudinally extending catheter lumen extending from the proximal end to near the distal end, and a second longitudinally extending catheter lumen, the second longitudinally extending catheter lumen extending proximally from a distal port at the distal end of the balloon catheter device; and a first expandable balloon having an interior space at the catheter distal end, the balloon interior space being in fluid communication with the first longitudinally extending catheter lumen; providing a balloon-on-a-wire device comprising an elongated wire having a length, a proximal end, a distal end, an outer surface, having at least one cut therein, polymer film covering at least a portion of the outer surface, and an inner surface, the inner surface defining a longitudinally extending wire lumen; and a second expandable balloon having an interior space at the wire distal end, the balloon interior space being in fluid communication with the longitudinally extending wire lumen wherein at least a portion of the balloon-on-a-wire device is slidably located within the second longitudinally extending catheter lumen; advancing the balloon catheter device and the balloon-on-a-wire device into a patient's vasculature, toward a treatment site; and advancing the second expandable balloon to a point distal to the catheter distal port and expanding the second expandable balloon; and while the second expandable balloon is expanded, distally advancing the balloon catheter device. Thereafter, the first expandable balloon can be expanded and the second expandable balloon contracted, and, while the first expandable balloon is expanded, distally advance the balloon-on-a-wire device.

In an aspect of the invention the second longitudinally extending catheter lumen extends proximally from the distal port to a proximal port located proximal to the first expandable balloon. In a further aspect of the invention the proximal port can be located at the balloon catheter proximal end. Moreover, the proximal port can be located distal to the balloon catheter proximal end. In a still further aspect of the invention the proximal port can be located relatively close to the distal port and relatively further from the balloon catheter proximal end.

In a still further aspect of the invention a balloon on a wire device comprises:

a proximal elongated wire having a length, an inner surface defining a longitudinally extending lumen, an outer surface having at least one cut therein, polymer film covering at least a portion of the outer surface, a proximal end, a distal end, and an outer diameter;

an intermediate elongated wire having a length, an inner surface defining a longitudinally extending lumen, an outer surface, a proximal end attached to the distal end of the proximal elongated wire, a distal end, and an outer diameter that is less than the proximal wire outer diameter;

a distal elongated wire having a length, an inner surface defining a longitudinally extending lumen, an outer surface, a proximal end attached to the distal end of the intermediate wire, a distal end, and an outer diameter that is greater than the intermediate wire outer diameter;

an expandable balloon located over the intermediate elongated wire and sealed to the device, the expandable balloon having an interior, an outer surface, a compressed state, an expanded state, a proximal end, and a distal end; and the expandable balloon interior being in fluid communication with at least one of the proximal wire lumen, the intermediate wire lumen, and the distal wire lumen through a port provided in at least one of the proximal, intermediate, and distal wires.

Either or both of the intermediate elongated wire and the distal elongated wire can further comprise at least one cut in the outer surface, the at least one cut can extend through to an inner surface of either or both of the intermediate and distal elongated wires. The at least one cut in the proximal, intermediate, and/or distal elongated wire can be spirally extending for any desired length of each wire and preferably extends through to the inner surface thereof.

Moreover, either or both of the intermediate elongated wire and the distal elongated wire can further comprise polymer film covering at least a portion of the outer surface thereof.

Figure 30:
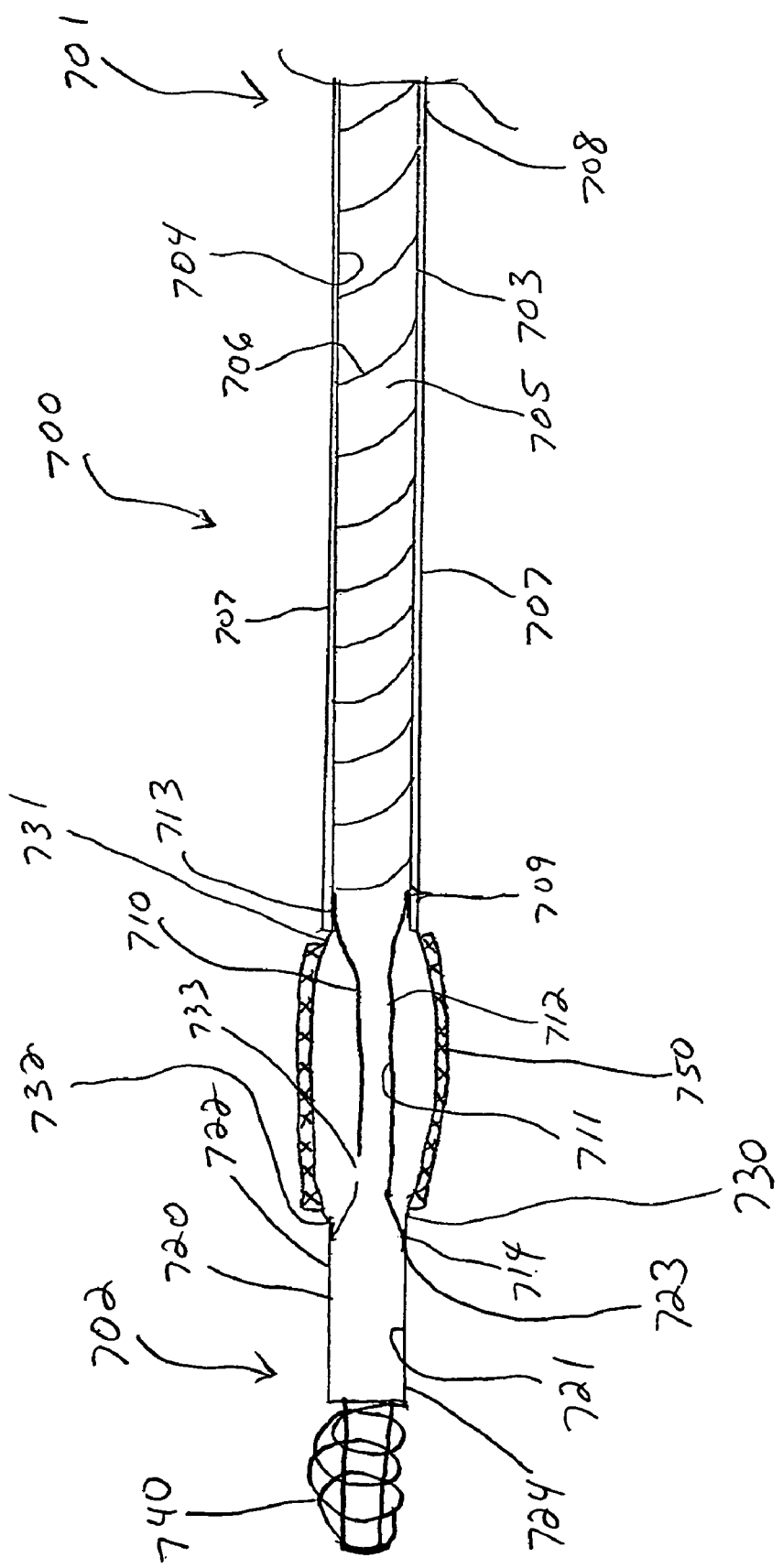
FIG. 30 is a longitudinal cross-section of a wire-based device according to the present invention.

This aspect of the invention may be better understood with reference to FIG. 30 wherein a non-limiting example is shown.

Shown in longitudinal cross section is balloon on a wire device 700. The device 700 has a proximal end 701 and a distal end 702 and further includes proximal elongated wire 703, having a length, an inner surface defining a longitudinally extending lumen 704, an outer surface 705 having at least one cut 706 therein, polymer film 707 covering at least a portion of the outer surface 705 of the wire, a proximal end 708, a distal end 709, and having an outer diameter. The device further includes intermediate elongated wire 710 having a length, an inner surface defining a longitudinally extending lumen 711, an outer surface 712, a proximal end 713 attached to the distal end of the proximal elongated wire, a distal end 714, and an outer diameter that is less than the proximal wire outer diameter. The device still further includes distal elongated wire 720 having a length, an inner surface defining a longitudinally extending lumen 721, an outer surface 722, a proximal end 723 attached to the distal end of the intermediate elongated wire, a distal end 724, and an outer diameter that is greater than the intermediate wire outer diameter. The device also includes expandable balloon 730 having a proximal end 731 sealed to the distal end of the proximal elongated wire and a distal end 732 sealed to the proximal end of the distal elongated wire. The balloon interior is in fluid communication with the lumen 711 of the intermediate wire 710 through port 733. The device can further include atraumatic tip 740 (such as a coil) attached to the distal end 724 of the distal elongated wire 720. Also shown is optional stent 750 loaded over balloon 730. The stent 750 has a length, an inner diameter, an outer diameter, a compressed state and an expanded state. In an aspect of the invention the diameter of the stent in its compressed state is equal to or less than the diameters of the proximal and distal ends of the balloon in its compressed state. Although the balloon 730 is shown with the distal end sealed to the proximal end of the distal elongated wire and the proximal end sealed to the distal end of the proximal elongated wire, the balloon ends can be sealed to any of the proximal elongated wire, the intermediate elongated wire and the distal elongated wire. In an aspect of the invention, the balloon distal end is sealed to the distal end of the intermediate elongated wire and the balloon proximal end is sealed to the proximal end of the intermediate elongated wire.

The invention claimed is:

1. Catheter comprising:
   a first longitudinally extending hollow polymer tube having a proximal end, a distal end, a wall having an inner surface and an outer surface, and a centrally located lumen extending from the proximal end to the distal end;
   a channel located in the wall forming an opening in the outer surface of the wall and extending from the proximal end to the distal end;
   polymer film helically wrapped about the outer surface, covering the channel from the proximal end to the distal end, thus covering the opening in the outer surface and forming a first wall inflation lumen extending from the proximal end to the distal end; and
   an inflatable member located on the distal end the catheter, the inflatable member selected from the group consisting of an occlusion balloon and a dilation balloon and being in fluid communication with the inflation lumen.

2. The catheter of claim 1 further comprising a second longitudinally extending hollow tube having a proximal end and a distal end, a wall having an inner surface and an outer surface, and a centrally located lumen extending from the proximal end to the distal end, wherein the second longitudinally extending hollow tube is located inside the first longitudinally extending hollow tube with the inner surface of the first tube being in contact with the outer surface of the second tube.

3. The catheter of claim 2, wherein the first polymer tube encapsulates a metal braid material.

4. The catheter of claim 3, wherein the first polymer tube comprises polyamide.

5. The catheter of claim 2, wherein the second tube comprises polytetrafluoroethylene.

6. The catheter of claim 5, wherein the polytetrafluoroethylene is extruded polytetrafluoroethylene.

7. The catheter of claim 2, wherein the catheter is sized to be capable of being advanced into a patient's cerebral vasculature.

8. The catheter of claim 1, wherein the polymer film comprises a material selected from the group consisting of ultra-high molecular weight polyethylene, polypropylene, polyamide, polyethylene terephthalate, fluorinated ethylene propylene, perfluoro alkoxy resin, polyurethane, polyester, and polyimide.

9. The catheter of claim 1, wherein the polymer film comprises polytetrafluoroethylene.

10. The catheter of claim 9, wherein the polymer film comprises expanded polytetrafluoroethylene.

11. The catheter of claim 10, wherein the expanded polytetrafluoroethylene is provided with a thermoplastic coating.

12. The catheter of claim 11, wherein the thermoplastic coating is a non-porous coating.

13. The catheter of claim 12, wherein the thermoplastic coating comprises fluorinated ethylene propylene.

14. The catheter of claim 10, wherein the expanded polytetrafluoroethylene is imbibed with at least one filler material.

15. The catheter of claim 14, wherein the at least one filler material comprises a radiopaque material.

16. The catheter of claim 1, wherein the channel is formed by a laser.

17. The catheter of claim 1, wherein the polymer film is helically wrapper about the outer surface of the first longitudinally extending hollow tube.

18. The catheter of claim 1, wherein the channel is a longitudinally extending channel.

19. The catheter of claim 1, wherein a guidewire is in sliding relationship with the centrally located lumen of the first longitudinally extending hollow tube.

20. The catheter of claim 1, wherein the catheter is sized to be capable of being advanced into a patient's cerebral vasculature.

21. The catheter of claim 1, wherein the inflatable member is an occlusion balloon.

22. The catheter of claim 1, wherein the inflatabled member is a dilatation balloon.

23. The catheter of claim 1, wherein a stent is mounted on the dilatation balloon.

24. The catheter of claim 1, further comprising at least a second channel located in the wall forming at least a second opening in the outer surface of the wall.

25. The catheter of claim 24, wherein the second channel extends from the proximal end to the distal end of the catheter.

26. The catheter of claim 24, wherein the polymer film covers the at least second opening in the outer surface of the wall, forming at least a second wall lumen.

27. The catheter of claim 26, wherein the second wall lumen extends from the proximal end to the distal end of the catheter.

28. The catheter of claim 24, wherein the at least second channel is a longitudinally extending channel.

29. The catheter of claim 1, wherein the polymer film is provided with an adhesive material to at least a portion of at least one side of the polymer film.

30. The catheter of claim 29, wherein the adhesive comprises a UV-curable adhesive.

31. Catheter comprising:
a first longitudinally extending hollow polymer tube having a proximal end, a distal end, a wall having an inner surface and an outer surface, and a centrally located lumen extending from the proximal end to the distal end;
a channel located in the wall forming an opening in the outer surface of the wall and extending from the proximal end to near the distal end;
polymer film helically wrapped about the outer surface, covering the channel from the proximal end to near the distal end, thus covering the opening in the outer surface and forming a first wall inflation lumen extending from the proximal end to near the distal end; and
an inflatable member located on the distal end of the catheter, the inflatable member selected from the group consisting of an occlusion balloon and a dilation balloon and being in fluid communication with the inflation lumen.

32. The catheter of claim 31, further comprising a second longitudinally extending hollow tube having a proximal end and a distal end, a wall having an inner surface and an outer surface, and a centrally located lumen extending from the proximal end to the distal end, wherein the second longitudinally extending hollow tube is located inside the first longitudinally extending hollow tube with the inner surface of the first tube being in contact with the outer surface of the second tube.

33. The catheter of claim 32, wherein the first polymer tube encapsulates a metal braid material.

34. The catheter of claim 33, wherein the first polymer tube comprises polyamide.

35. The catheter of claim 32, wherein the second tube comprises polytetrafluoroethylene.

36. The catheter of claim 35, wherein the polytetrafluoroethylene is extruded polytetrafluoroethylene.

37. The catheter of claim 32, wherein the catheter is sized to be capable of being advanced into a patients cerebral vasculature.

38. The catheter of claim 31, wherein the polymer film comprises a material selected from the group consisting of ultra-high molecular weight polyethylene, polypropylene, polyamide, polyethylene terephthalate, fluorinated ethylene propylene, perfluoro alkoxy resin, polyurethane, polyester, and polyimide.

39. The catheter of claim 31, wherein the polymer film comprises polytetrafluoroethylene.

40. The catheter of claim 39, wherein the polymer film comprises expanded polytetrafluoroethylene.

41. The catheter of claim 40, wherein the expanded polytetrafluoroethylene is provided with a thermoplastic coating.

42. The catheter of claim 41, wherein the thermoplastic coating is a non-porous coating.

43. The catheter of claim 42, wherein the thermoplastic coating comprises fluorinated ethylene propylene.

44. The catheter of claim 40, wherein the expanded polytetrafluoroethylene is imbibed with at least one filler material.

45. The catheter of claim 44, wherein the at least one filler material comprises a radiopaque material.

46. The catheter of claim 31, wherein the channel is a formed by a laser.

47. The catheter of claim 31, wherein the polymer film is helically wrapped about the outer surface of the first longitudinally extending hollow tube.

48. The catheter of claim 31, wherein the channel is a longitudinally extending channel.

49. The catheter of claim 31, wherein a guidewire is in sliding relationship with the centrally located lumen of the first longitudinally extending hollow tube.

50. The catheter of claim 31, wherein the catheter is sized to be capable of being advanced into a patient's cerebral vasculature.

51. The catheter of claim 31, wherein the inflatable member is an occlusion balloon.

52. The catheter of claim 31, wherein the inflatable member is a dilatation balloon.

53. The catheter of claim 31, wherein a stent is mounted on the dilatation balloon.

54. The catheter of claim 31, further comprising at least a second channel located in the wall forming at least a second opening in the outer surface of the wall.

55. The catheter of claim 54, wherein the second channel extends from the proximal end to the distal end of the catheter.

56. The catheter of claim 54, wherein the polymer film covers the at least second opening in the outer surface of the wall, forming at least a second wall lumen.

57. The catheter of claim 56, wherein the second wall lumen extends from the proximal end to the distal end of the catheter.

58. The catheter of claim 54, wherein the at least second channel is a longitudinally extending channel.

59. The catheter of claim 31, wherein the polymer film is provided with an adhesive material to at least a portion of at least one side of the polymer film.

60. The catheter of claim 59, wherein the adhesive comprises a UV-curable adhesive.

* * * * *